(12) United States Patent
Worboys et al.

(10) Patent No.: US 9,295,805 B2
(45) Date of Patent: Mar. 29, 2016

(54) ANTI-ASPHYXIA VALVE ASSEMBLY FOR RESPIRATOR MASK

(75) Inventors: David John Worboys, Belrose (AU); Alison Oldenburg, Crows Nest (AU); Philip Thomas Stallard, Denistone East (AU); James William Charles Vandyke, Belrose (AU); Susan Robyn Lynch, Bella Vista (AU); Steven John Lubke, Stanmore (AU); Scott Alexander Howard, Harbord (AU); Robin Garth Hitchcock, Normanhurst (AU)

(73) Assignee: ResMed Limited, Bella Vista (AU)

( * ) Notice: Subject to any disclaimer, the term of this patent is extended or adjusted under 35 U.S.C. 154(b) by 1988 days.

(21) Appl. No.: 12/083,349

(22) PCT Filed: Jan. 12, 2006

(86) PCT No.: PCT/AU2006/000031
§ 371 (c)(1),
(2), (4) Date: Apr. 10, 2008

(87) PCT Pub. No.: WO2007/045008
PCT Pub. Date: Apr. 26, 2007

(65) Prior Publication Data
US 2009/0065729 A1     Mar. 12, 2009

Related U.S. Application Data

(60) Provisional application No. 60/726,699, filed on Oct. 17, 2005.

(51) Int. Cl.
*A61M 16/20* (2006.01)
*A61M 16/06* (2006.01)
*A61M 16/08* (2006.01)

(52) U.S. Cl.
CPC ............. *A61M 16/208* (2013.01); *A61M 16/06* (2013.01); *A61M 16/08* (2013.01); *A61M 16/0816* (2013.01); *A61M 2205/42* (2013.01)

(58) Field of Classification Search
CPC .......... A61M 16/208; F16K 1/16; F16K 1/18; F16K 15/031
USPC .............. 128/202.27, 204.18, 205.24, 207.16
See application file for complete search history.

(56) References Cited

U.S. PATENT DOCUMENTS 3,796,216 A    3/1974  Schwarz
5,438,981 A    8/1995  Starr et al.
(Continued)

FOREIGN PATENT DOCUMENTS

EP              1525895         4/2005
WO       PCT/AU97/00849         12/1997
(Continued)

OTHER PUBLICATIONS

International Search Report for PCT/AU2006/000031, dated Mar. 23, 2006.
(Continued)

*Primary Examiner* — Justine Yu
*Assistant Examiner* — LaToya M Louis
(74) *Attorney, Agent, or Firm* — Nixon & Vanderhye P.C.

(57) ABSTRACT

An elbow assembly for a mask assembly includes an anti-asphyxia valve (AAV) assembly that may take the form of a box-like frame work, a drop-in arrangement, or a slot-in arrangement. In each case, the AAV assembly may include a flap element which is movable so as to either direct ambient gas/air to the elbow assembly and thus the patient using the mask assembly, or to allow the passage of pressurized gas to the patient.

41 Claims, 89 Drawing Sheets

(56) References Cited

U.S. PATENT DOCUMENTS

| | | | |
|---|---|---|---|
| 5,465,712 A * | 11/1995 | Malis et al. ............... 128/205.25 |
| 5,647,355 A | 7/1997 | Starr et al. |
| 6,983,556 B2 * | 1/2006 | McMullin ..................... 36/67 R |
| 8,136,524 B2 | 3/2012 | Ging et al. |
| 2002/0153012 A1 | 10/2002 | Gunaratnam et al. |
| 2002/0174867 A1 * | 11/2002 | Gunaratnam et al. ... 128/204.18 |
| 2003/0005931 A1 | 1/2003 | Jaffre |
| 2003/0196656 A1 | 10/2003 | Moore et al. |
| 2003/0196657 A1 | 10/2003 | Ging |
| 2004/0112385 A1 | 6/2004 | Drew |
| 2004/0255948 A1 | 12/2004 | Smith et al. |
| 2010/0236549 A1 | 9/2010 | Selvarajan et al. |
| 2013/0008439 A1 | 1/2013 | Selvarajan et al. |

FOREIGN PATENT DOCUMENTS

| | | |
|---|---|---|
| WO | WO 00/38772 | 7/2000 |
| WO | WO 02/051486 | 7/2002 |
| WO | WO 02/096342 A2 | 12/2002 |
| WO | WO 2005/063326 | 7/2005 |
| WO | WO 2005/063328 A1 | 7/2005 |
| WO | WO 2006/122369 | 11/2006 |
| WO | WO 2006/130903 A1 | 12/2006 |
| WO | WO 2007/045008 A1 | 4/2007 |

OTHER PUBLICATIONS

Office Action Mailed Mar. 28, 2011 in European Application No. 06 704 169.9 (5 pages).

Third Party Observations Mailed Mar. 25, 2011 in European Application No. 06 704 169.9 (2 pages).

European Search Report issued in Ep Appln. No. 06704169.9, mailed Mar. 4, 2010, 7 pgs.

Communication issued Mar. 7, 2013 in European Application No. 06 704 169.9 (4 pages).

* cited by examiner

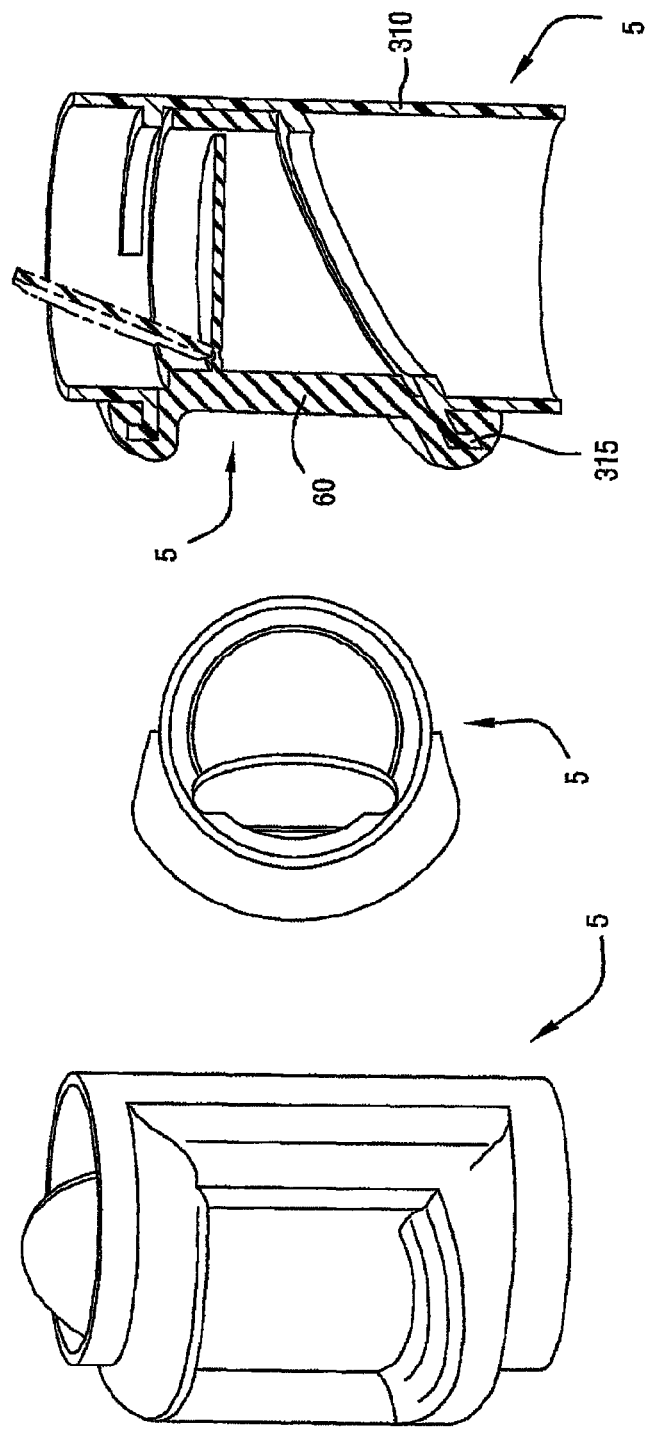

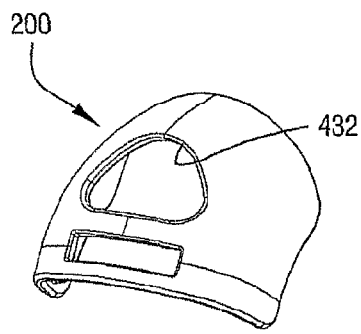
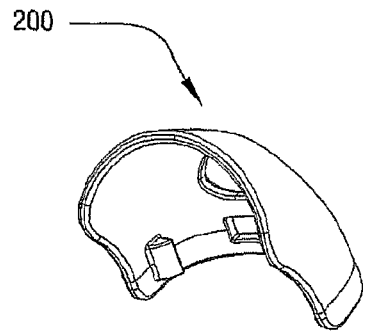
Fig. 105
Fig. 106
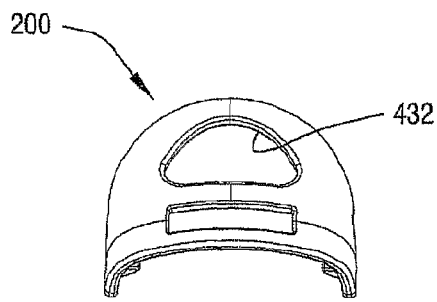
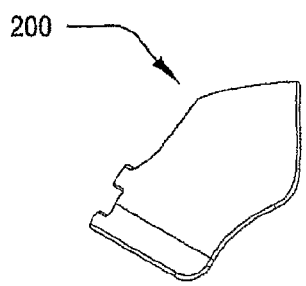
Fig. 107
Fig. 108
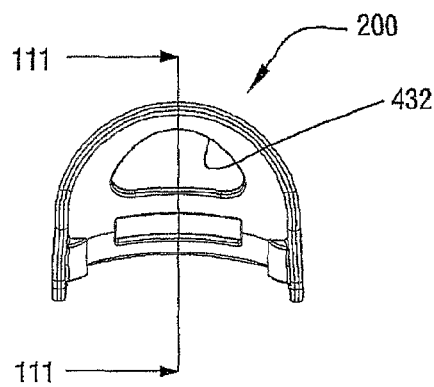
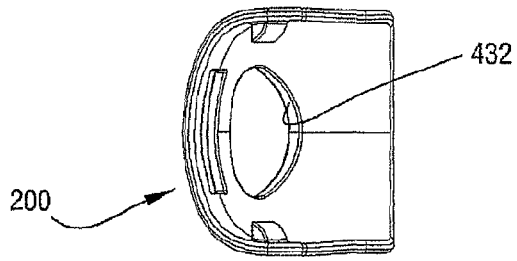
Fig. 109
Fig. 110
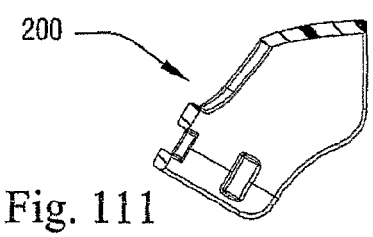
Fig. 111

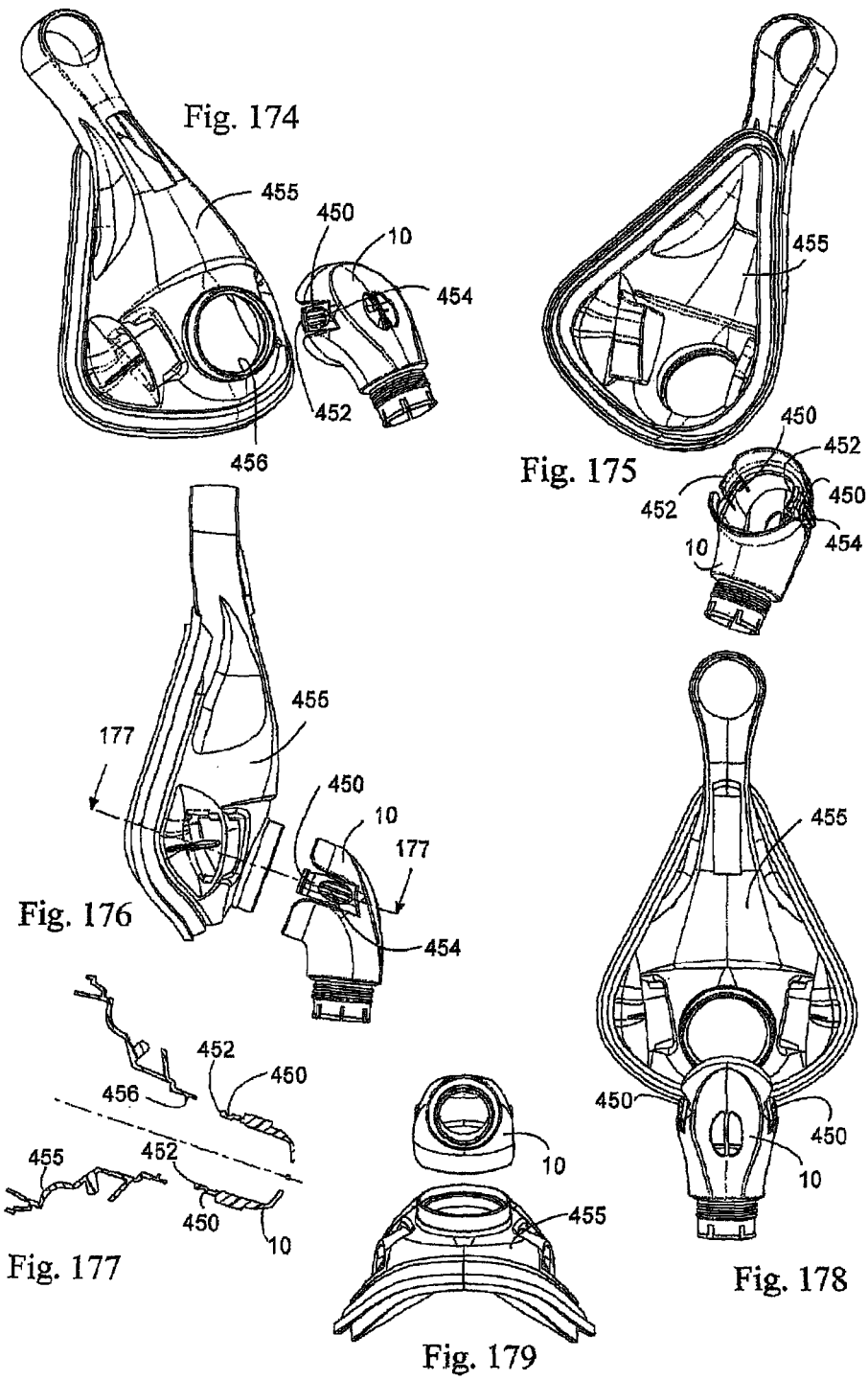

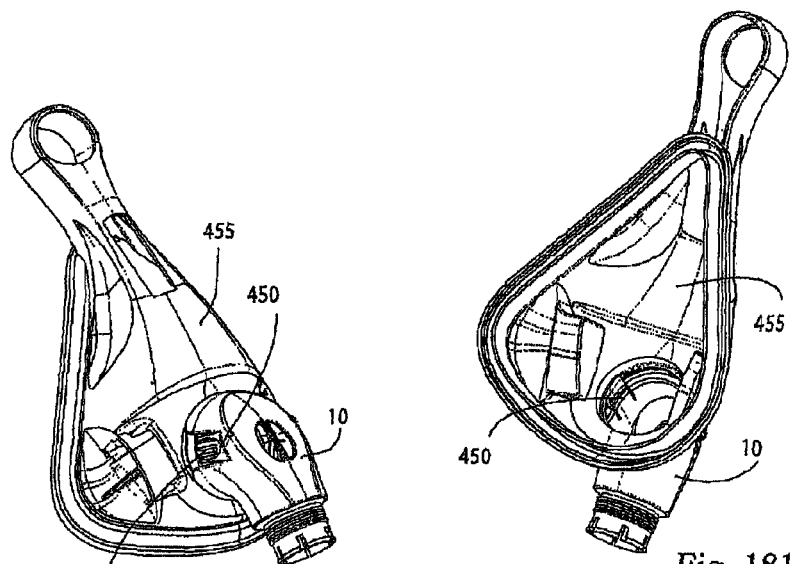
Fig. 180   Fig. 181
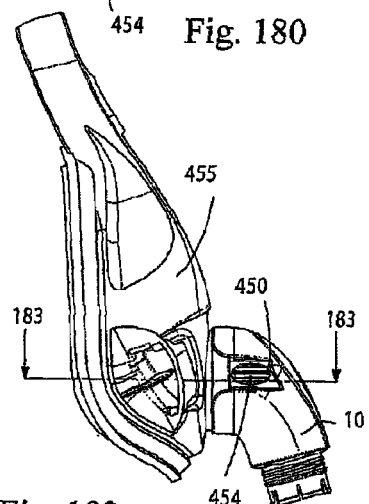 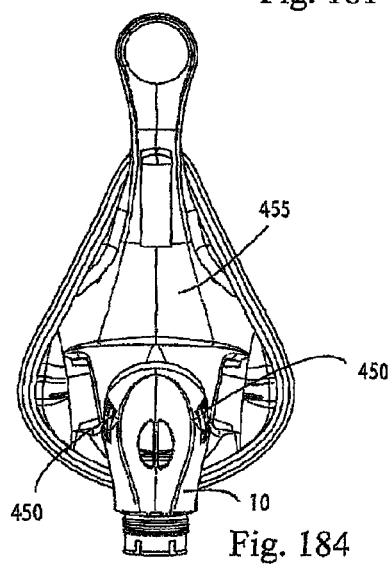
Fig. 182   Fig. 184
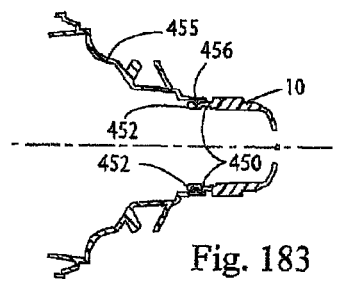 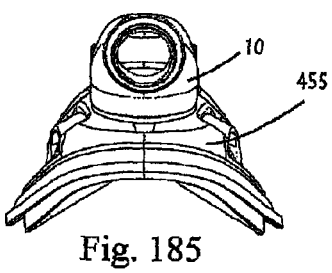
Fig. 183   Fig. 185

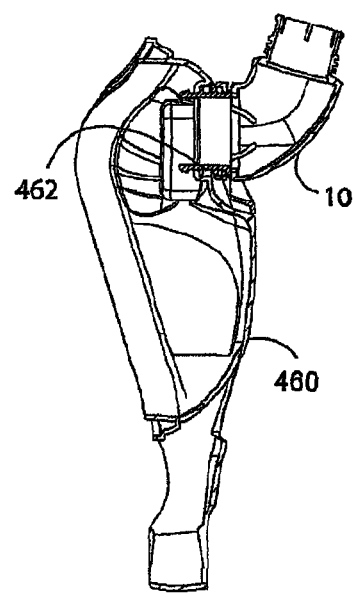
Fig. 201
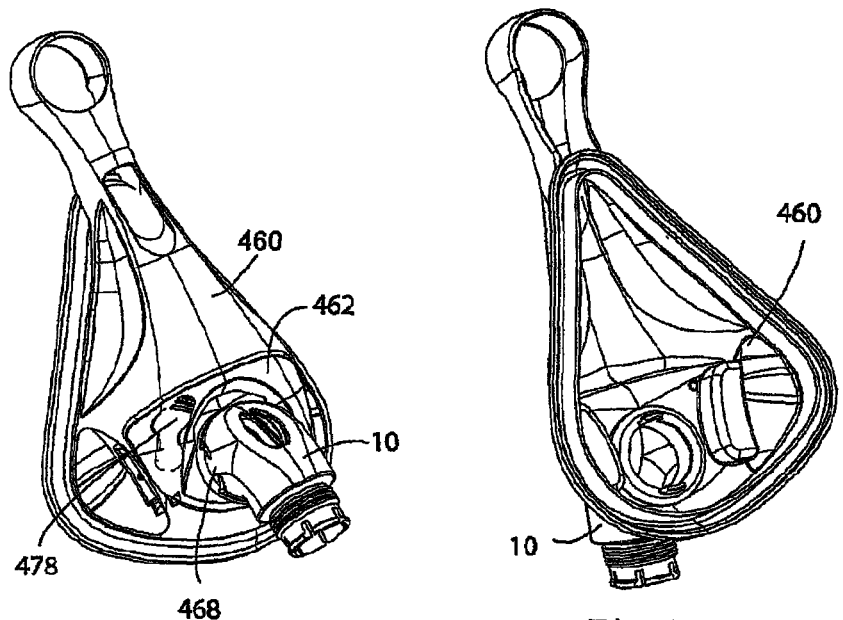
Fig. 202
Fig. 203

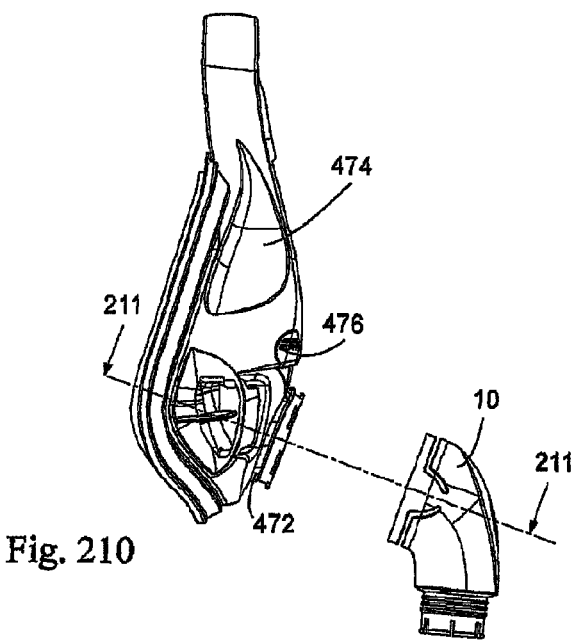
Fig. 210
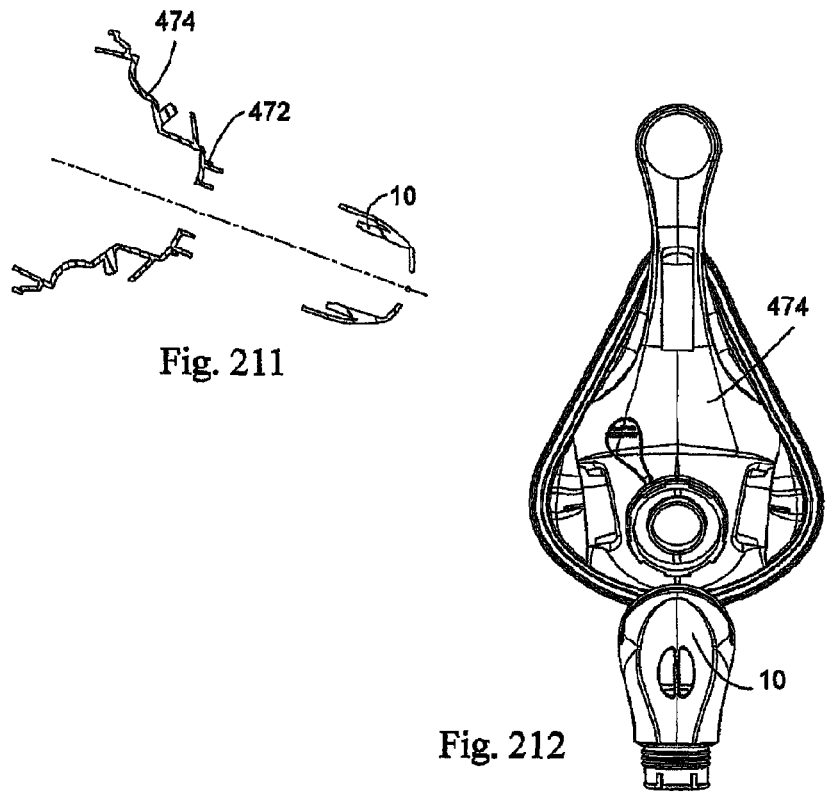
Fig. 211
Fig. 212

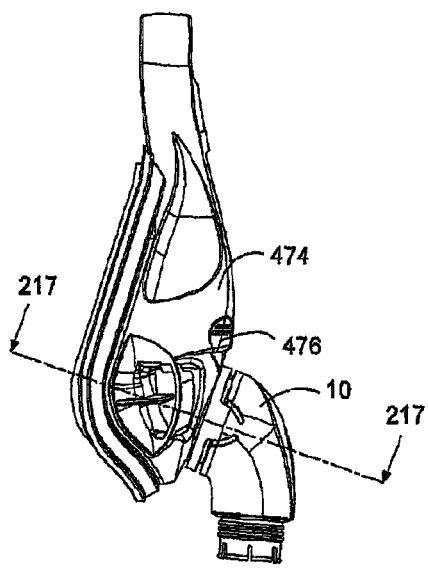
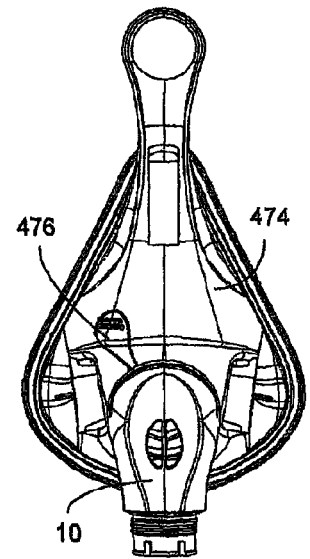
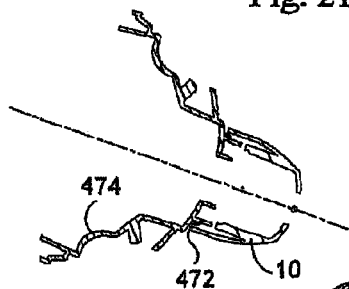
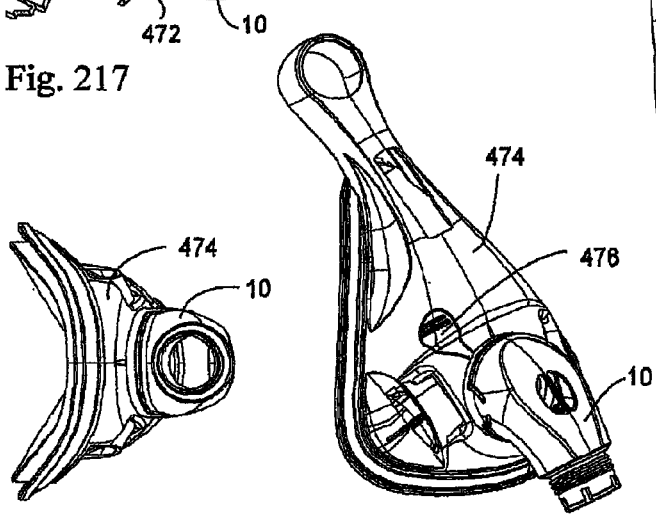
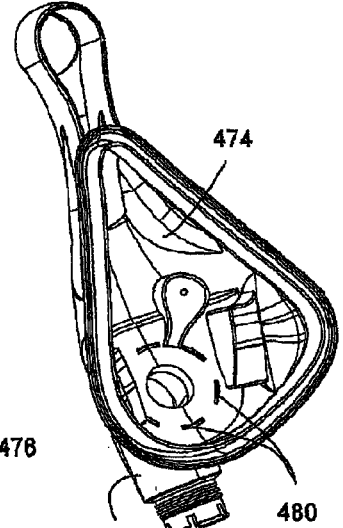
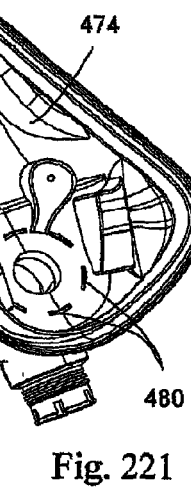
Fig. 216
Fig. 218
Fig. 217
Fig. 219
Fig. 220
Fig. 221

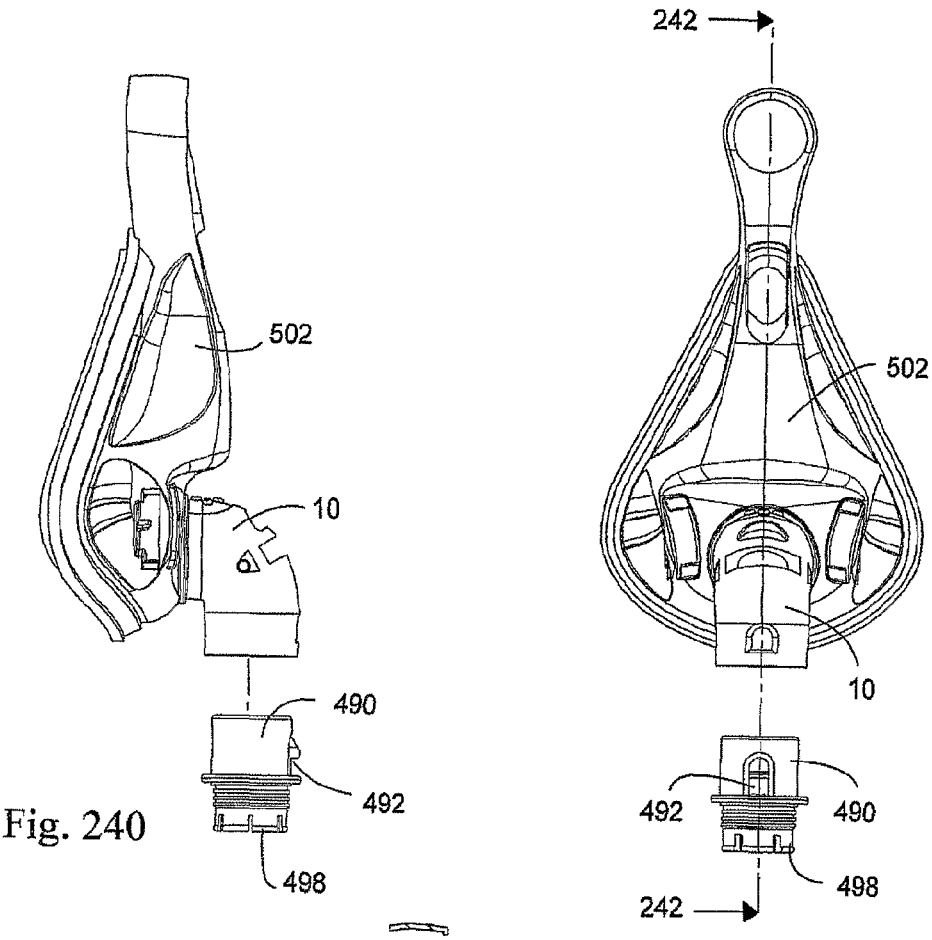
Fig. 240
Fig. 241
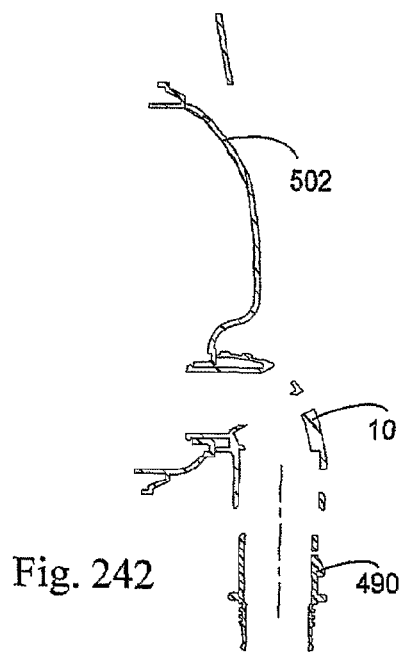
Fig. 242

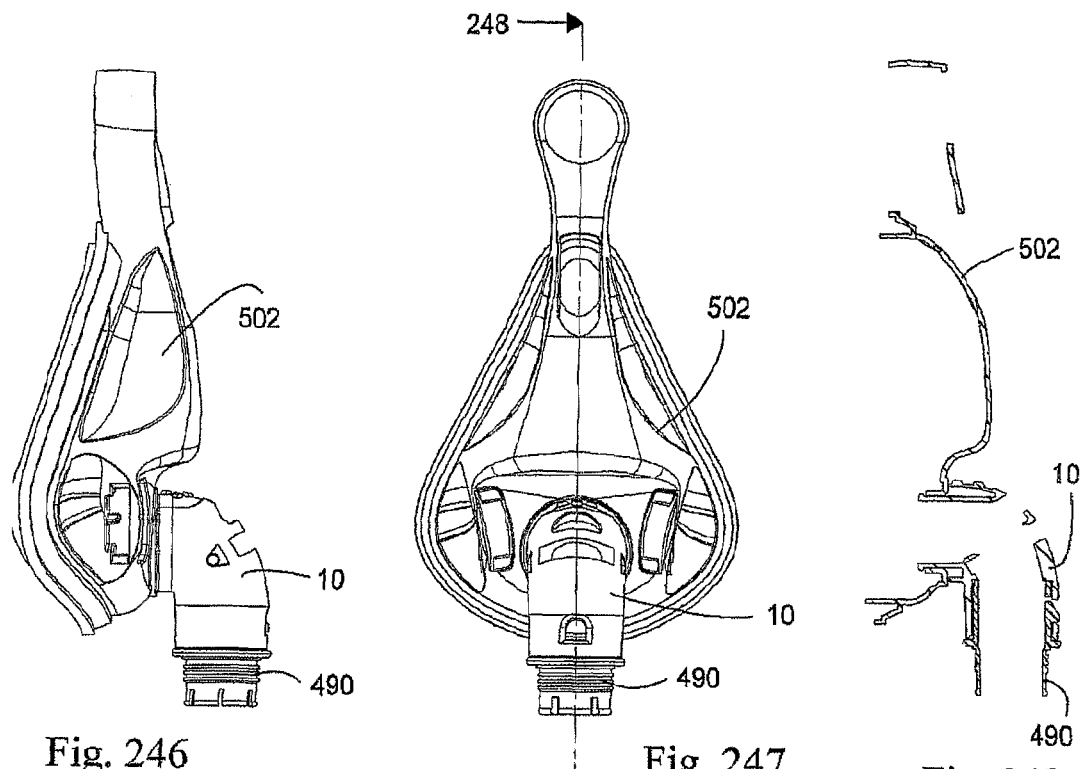
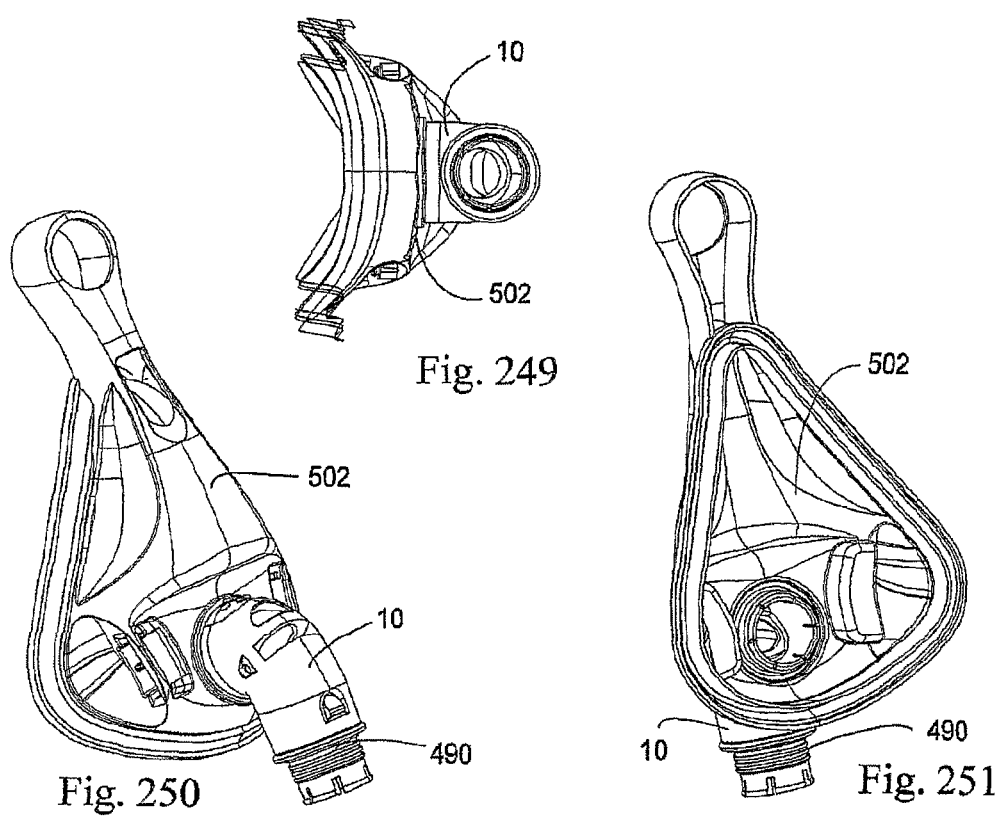

ANTI-ASPHYXIA VALVE ASSEMBLY FOR RESPIRATOR MASK

CROSS REFERENCE TO PRIORITY APPLICATIONS

This application is the U.S. national phase of International Application No. PCT/AU2006/000031, filed Jan. 12, 2006, which designated the U.S. and claims the benefit of U.S. Provisional Application No. 60/726,699, filed Oct. 17, 2005, each of which is incorporated herein by reference in its entirety.

FIELD OF THE INVENTION

The present invention relates to an elbow for use with a mask assembly used for treatment, e.g., of Sleep Disordered Breathing (SDB) with Continuous Positive Airway Pressure (CPAP) or Non-Invasive Positive Pressure Ventilation (NPPV).

BACKGROUND OF THE INVENTION

A mask assembly typically includes a relatively rigid shell, e.g., a frame, and a patient interface, e.g., a pair of nozzles (which may be in the form of nasal pillows, nasal prongs, cannulae, or nasal puffs) or a cushion (nasal or full-face), that is supported by the rigid shell and structured to deliver pressurized gas to the patient or user in a comfortable, sealed manner. The mask assembly is usually held in place using a headgear assembly.

In some applications, there may be a clinical requirement to provide the mask assembly with one or more safety devices, such as means for $CO_2$ washout, vents, anti-asphyxia valves and the like. In some cases, these additional components are assembled between the gas delivery conduit and the mask assembly. Problems with prior art assemblies may include:

(a) inadvertent assembly without one or more of the safety devices;

(b) incorrect assembly/alignment; and/or (c) incorrect re-assembly following inadvertent dis-assembly during the course of treatment.

Flow generators typically deliver pressurized breathable gas (air) to a patient wearing the mask assembly. In CPAP treatment, gas is delivered to the patient's airways at about 2-30 cm $H_2O$ above atmospheric pressure. The flow generator is generally connected to flexible tubing (air delivery tube) that is secured to the mask assembly worn by the patient. If the flow generator's operation is interrupted as a result of power outage or other mechanical/electrical failure, there may be a significant build up of carbon dioxide in the mask as the patient's exhaled air is not washed out of outlet vents that are usually provided to the mask assembly. This may present a health risk to the patient.

Several patents have addressed this risk, e.g., by use of a safety valve for gas or air delivery mask assemblies. See, e.g., U.S. Pat. No. 3,796,216 to Schwarz, and U.S. Pat. No. 5,438,981 to Starr et al., as well as PCT international application no. PCT/AU97/00849.

BRIEF SUMMARY OF THE INVENTION

According to one aspect of the invention, there is provided an elbow assembly comprising an elbow; an anti-asphyxia valve (AAV) assembly provided to the elbow; and a clip member or portion to secure the AAV assembly to the elbow According to yet another aspect of the invention, there is provided an elbow assembly for a mask, comprising: an elbow having a first portion structured to engage with a mask frame and a second portion structured to receive pressurized gas; a first gas path defined between the first and the second portions; a port in communication with atmosphere and in selective communication with the first portion of the elbow; a second gas path defined between the first portion and the port; and an anti-asphyxia valve (AAV) assembly, said AAV assembly including a flap portion and a frame assembly integrally supporting the flap portion, the flap portion being movable to selectively open and close the port, wherein said flap portion assumes a closed position when pressurized gas less than or equal to a predetermined threshold is delivered to the second portion of the elbow, in which case the port can communicate with the first portion via the second gas path, and said flap assumes an open position when pressurized gas above the predetermined threshold is delivered to the second portion, in which case the flap portion seals the port and the first portion is in communication with the second portion via the first gas path.

According to still another aspect of the present invention, there is provided a mask assembly comprising a frame; an elbow provided to the frame; and an anti-asphyxia valve (AAV) assembly secured within the elbow upon assembly of the elbow to the frame.

According to yet another embodiment of the present invention, there is provided an elbow assembly comprising an elbow, the elbow having a first portion adapted to be secured to a mask and a second portion adapted to receive pressurized gas, the first and the second portions having connection structure allowing selective connection and disconnection between the first and second portions, the connection structure including a pair of resilient arms provided on one of the first and second portions and a flange provided on the other of the first and second portions, each of the arms including a claw to lock with the flange; and an anti-asphyxia valve (AAV) assembly provided within the elbow and sandwiched between the first and second portions.

Another aspect of the present invention relates to a mask assembly including a frame, an elbow provided to the frame, and an elbow to frame assembly mechanism to releasably assemble the elbow to the frame. The elbow to frame assembly mechanism includes an elbow to frame adaptor that attaches to the frame and provides a flanged collar member onto which the elbow can be releasably assembled.

Another aspect of the present invention relates to a mask assembly including a frame, an elbow having one end provided to the frame and an opposite end provided to a swivel, and an elbow-to-swivel adaptor to connect the elbow to the swivel. The elbow-to-swivel adaptor includes a snap-fit tab to connect the elbow-to-swivel adaptor to the elbow with a snap-fit.

Another aspect of the present invention relates to a mask assembly including a frame, an elbow provided to the frame, and an integrated elbow seal and port cap assembly provided between the elbow and the frame. The elbow seal and port cap assembly includes an elbow seal to provide a seal between the elbow and the frame and a port cap to releasably connect to a port provided to the frame.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 59 is perspective view of a portion of an elbow assembly on a conduit having an AAV assembly according to an embodiment of the present invention;

FIG. 60 is a top view thereof;

FIG. 61 is cross-sectional view thereof;

FIGS. 90-111 show various views of an elbow assembly according to another embodiment of the present invention;

FIGS. 174-185 illustrate an elbow to frame assembly mechanism according to an embodiment of the present invention;

FIGS. 186-203 illustrate an elbow to frame assembly mechanism according to another embodiment of the present invention;

FIGS. 204-221 illustrate an elbow to frame assembly mechanism according to another embodiment of the present invention;

FIGS. 234-251 illustrate an elbow to frame assembly mechanism according to another embodiment of the present invention;

DETAILED DESCRIPTION OF ILLUSTRATED EMBODIMENTS

The following description is provided in relation to several embodiments which may share common characteristics and features. It is understood that one or more features of any one embodiment may be combinable with one or more features of the other embodiments.

1.0 "Letter Box" AAV Assembly

1.1 First Embodiment

Figure 1:
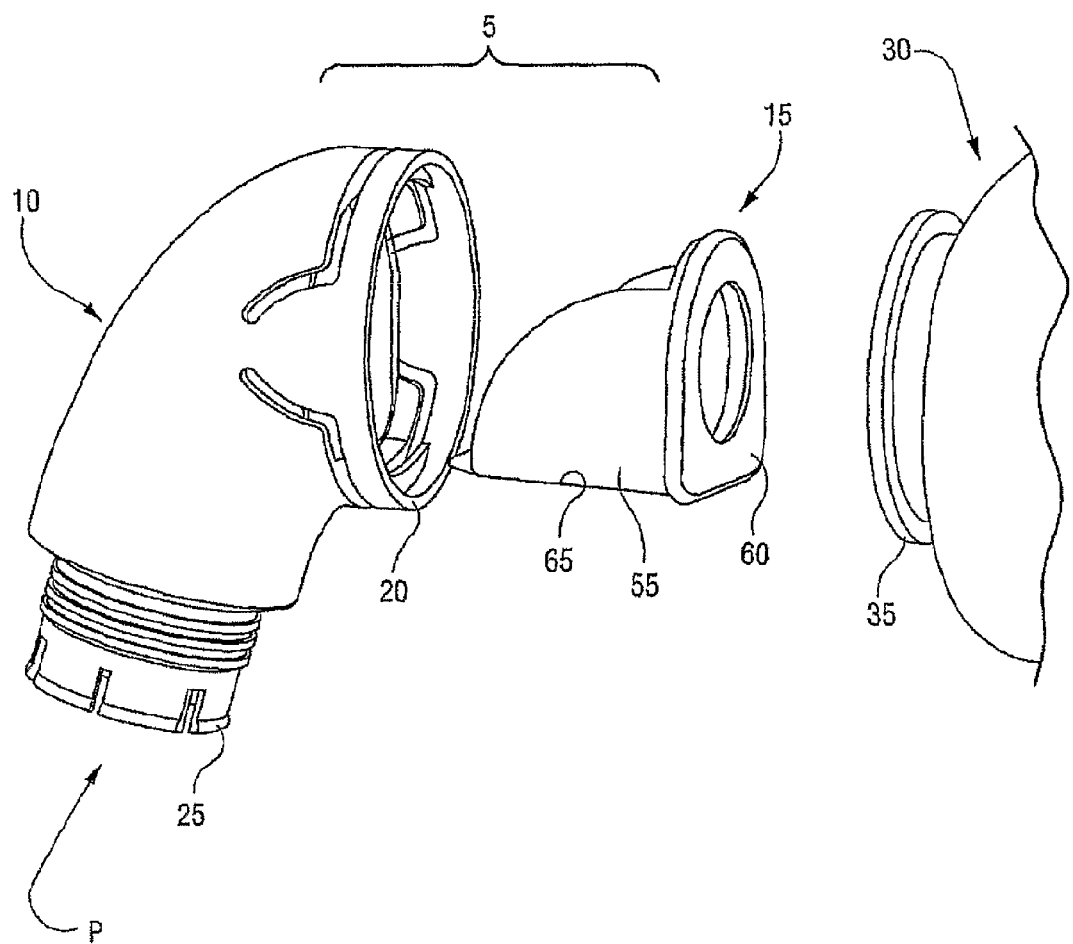
FIG. 1 is an exploded, perspective view of an elbow assembly according to one embodiment of the present invention.

FIGS. 1-9 illustrate an elbow assembly 5 according to a first embodiment of the invention. As shown in FIG. 1, the elbow assembly 5 generally comprises an elbow 10 and an anti-asphyxia valve 15 (AAV) assembly.

The elbow has a first portion 20 and a second portion 25. The first portion 20 is connected or otherwise provided to a mask frame 30 of a mask assembly (not shown in FIG. 1), e.g., in a snap-fit manner, as is known from U.S. patent application publication no. 2003/0196656 incorporated herein by reference. Only a portion of the frame of the mask assembly is shown in FIG. 1. The frame includes a flanged collar member 35 onto which the first portion 20 of the elbow 10 can be releasably connected.

The second portion 25 is intended to receive pressurized gas from a source of pressurized gas (e.g., air from a CPAP machine or other ventilation device). The second portion 25 typically will be provided with a swivel joint which in turn is connected to an air delivery tube in communication with a flow generator. However, the second portion 25 may have other connections, e.g., tapered joint to allow attachment to a short tube. The elbow 10 can be made from a relatively rigid material, such as polycarbonate or other plastic.

Figure 2:
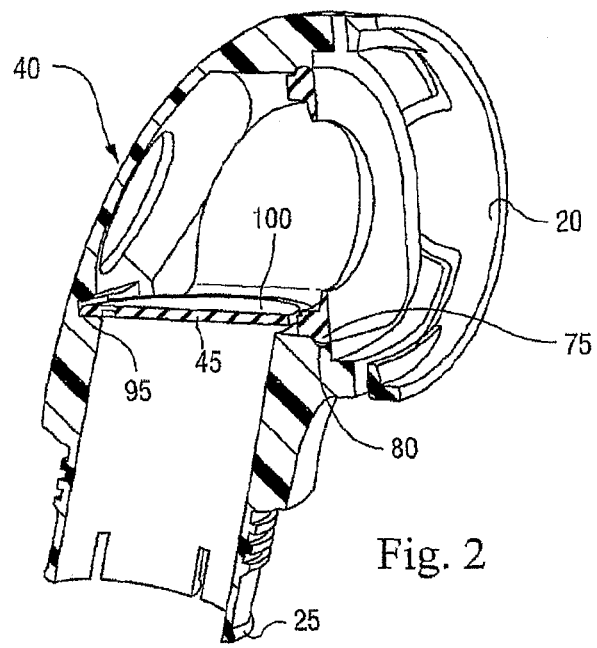
FIG. 2 is a cross-sectional view of the elbow assembly of FIG. 1 in the assembled condition.
Figure 3:
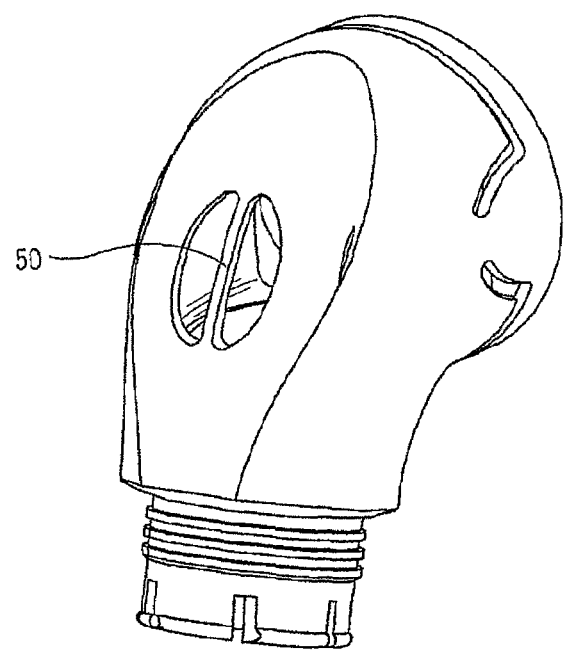
FIG. 3 is a rear view of the elbow assembly of FIG. 1.

The cross-section of FIG. 2 shows the assembled condition of the AAV assembly 15 and the elbow 10. The elbow 10 includes a port 40 that may be selectively closed by a flap portion 45 of the AAV assembly. If the pressurized gas provided to the second portion 25 of the elbow 10 is of sufficient magnitude, the flap portion 45 will raise to the block off the port 40. In this case, pressurized gas will be guided from the second portion 25 toward the first portion 20, for delivery to the mask and the patient's airways. If pressurized gas is not delivered due to a power outage and/or mechanical/electrical failure, the flap portion 45 will remain in the "rest" position shown in FIG. 2, so that the patient can breathe in ambient air and exhale through the port 40. FIG. 3 shows that the port includes a cross member 50 provided as part of the elbow.

The AAV assembly can be inserted from the direction of the frame 30 to elbow 10 (right to left in FIG. 1). Accordingly, the AAV assembly is sandwiched in place when the elbow assembly (elbow and AAV assembly) are connected to the frame. This helps avoid inadvertent disassembly.

The elbow 10 includes internal structure to hold the AAV assembly 15 in position. More specifically, the AAV assembly 15 includes a frame assembly 55 which in this embodiment generally resembles a "letter box" or "mail box", including an main wall member 60, side wall members 65 and a base portion 70 that supports the flap portion 45. The side wall members 65 are tapered so as to generally match the interior contour of the elbow 10.

The main wall member 60 includes an outer rim 75 including a protruding bead that is intended to be received in a corresponding groove 80 in the elbow 10. The AAV assembly is easily disassembled once the elbow is removed from the frame. The AAV assembly is a relatively large, three dimensional component, which reduces the chance that it will become lost. Its size and shape also facilitates finding, holding and assembling the AAV assembly. Moreover, the AAV assembly can only be assembled in one manner. The cross member 50 is provided on the elbow to prevent the flap portion from being over-pressurized. The cross member 50 also prevents inadvertent AAV assembly, e.g., pushing through the atmospheric hole, and blocking the atmospheric hole which could cause inadvertent deactivation.

The main wall member 60 also includes an aperture 85 defined by a circumferential seal lip 90 that is intended to sealingly engage a portion of the mask frame upon assembly (see FIG. 17, discussed more below). The AAV assembly therefore combines the typical function of an AAV assembly with that of sealing the elbow to frame connection. Sealing in this manner may provide one or more of the following advantages: prevent/reduce elbow/frame rattling; provide high quality feel; prevent/reduce overly free rotation; dampen vibration; prevent/reduce squeak; reduce inadvertent (and often variable) leak; and/or reduce tolerance requirements for the "hard" components (e.g., frame, elbow, etc.).

The elbow also includes an internal shoulder 95 that supports the AAV assembly. In this embodiment, the shoulder supports the base portion 70 of the AAV assembly. The flap portion 45 is movably provided, e.g., hingedly connected, to the base portion in an orientation such that the flap portion pivots at a point just below the port 40. This pivoting occurs at a position which is opposite to the main wall member 60. The free end 100 of the flap portion is also supported by the shoulder of the elbow, as shown in FIG. 2.

Figure 4:
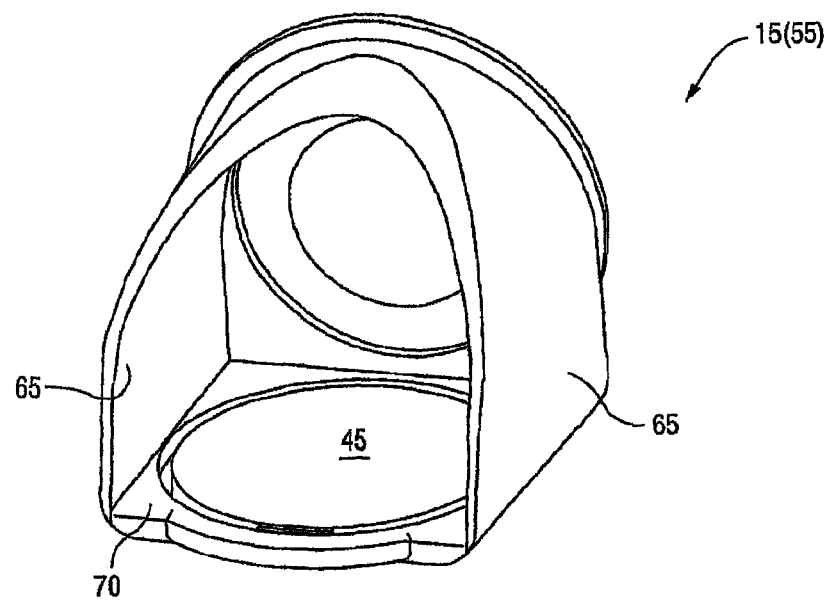
FIG. 4 is a front perspective view of the AAV assembly of FIG. 1.
Figure 5:
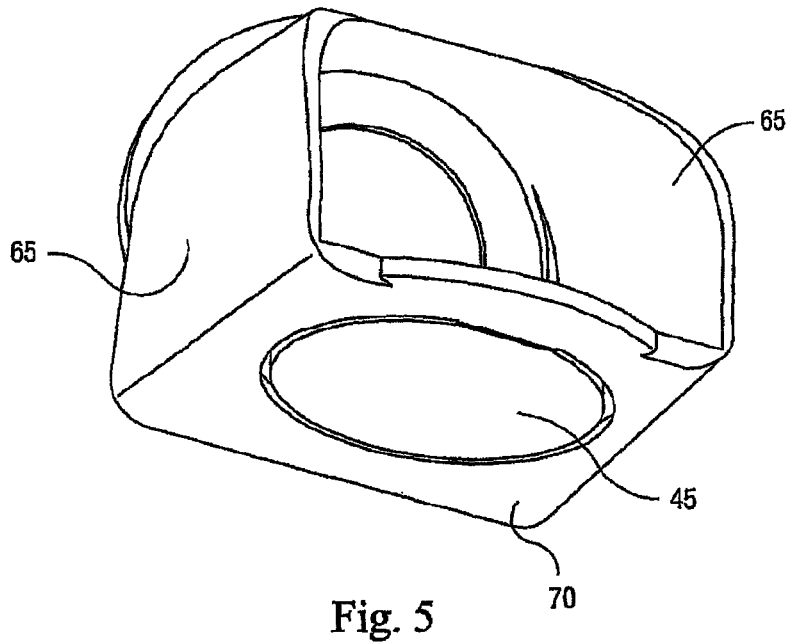
FIG. 5 is a reverse perspective view thereof.
Figure 6:
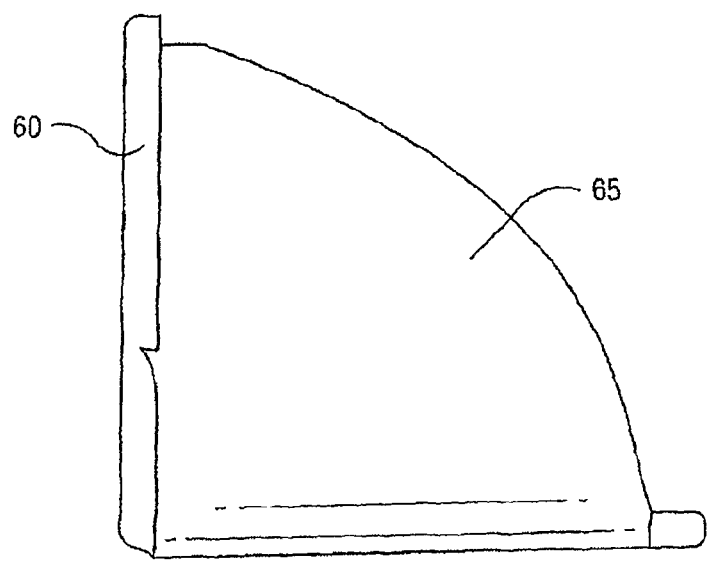
FIG. 6 is a side elevation view thereof.
Figure 7:
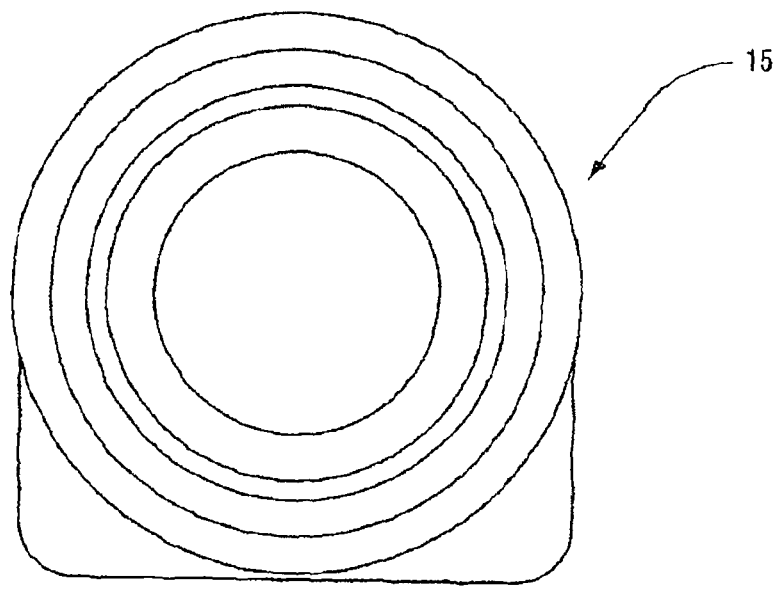
FIG. 7 is a front view thereof.
Figure 8:
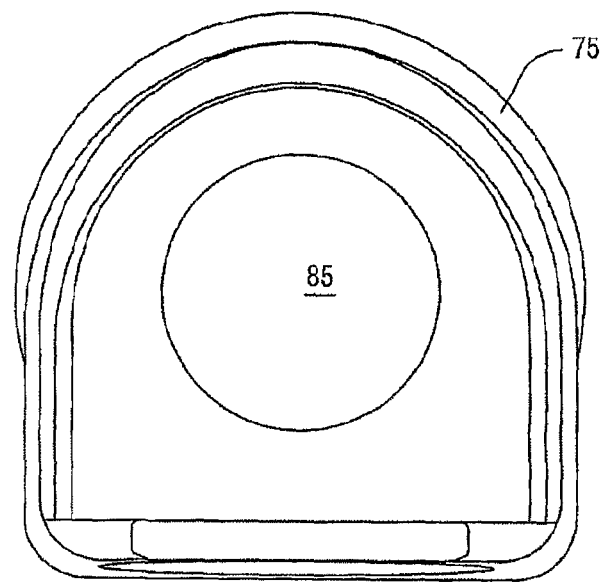
FIG. 8 is a rear view thereof.
Figure 9:
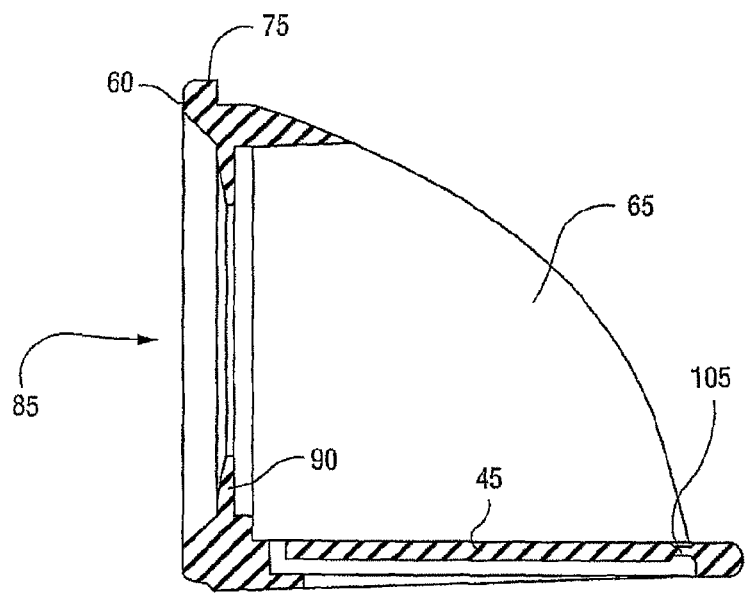
FIG. 9 is a cross-sectional view thereof.
Figure 10:
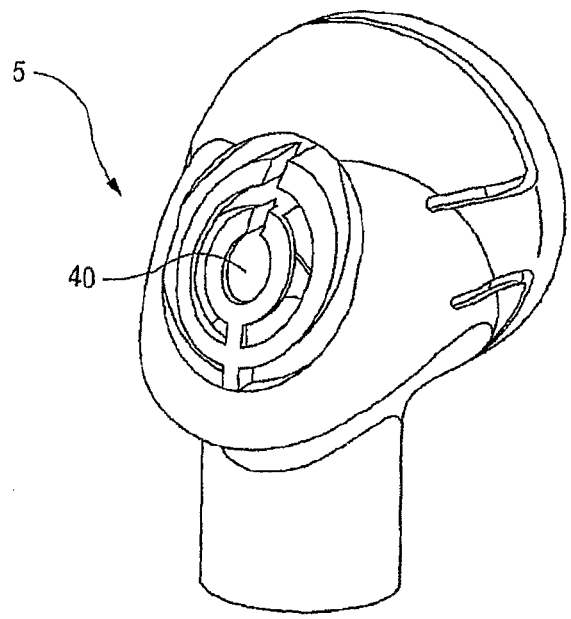
FIG. 10 is a perspective view of an elbow assembly according to another embodiment of the present invention.
Figure 11:
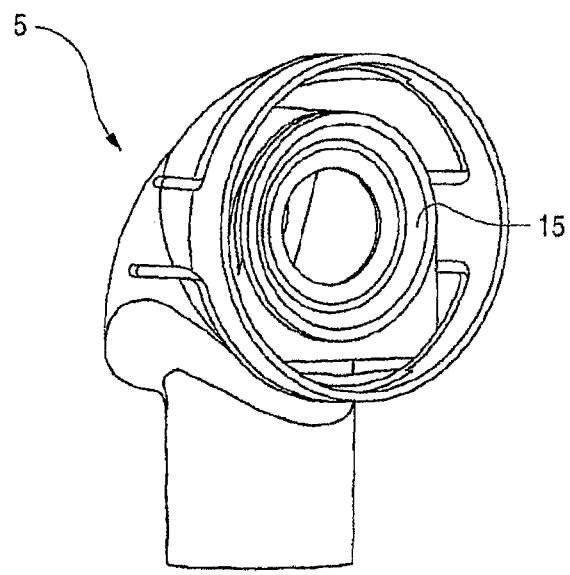
FIG. 11 is a reverse perspective view thereof.
Figure 12:
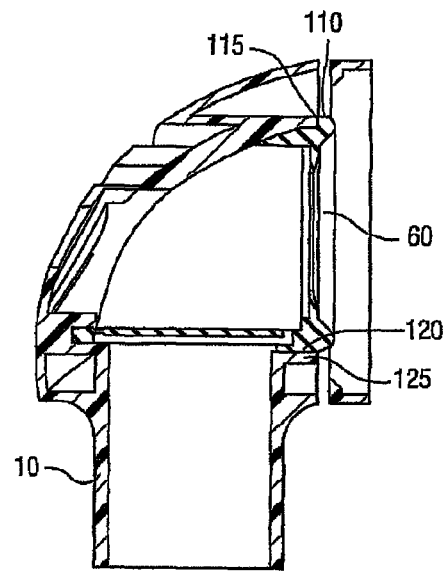
FIG. 12 is a cross-sectional view thereof.
Figure 13:
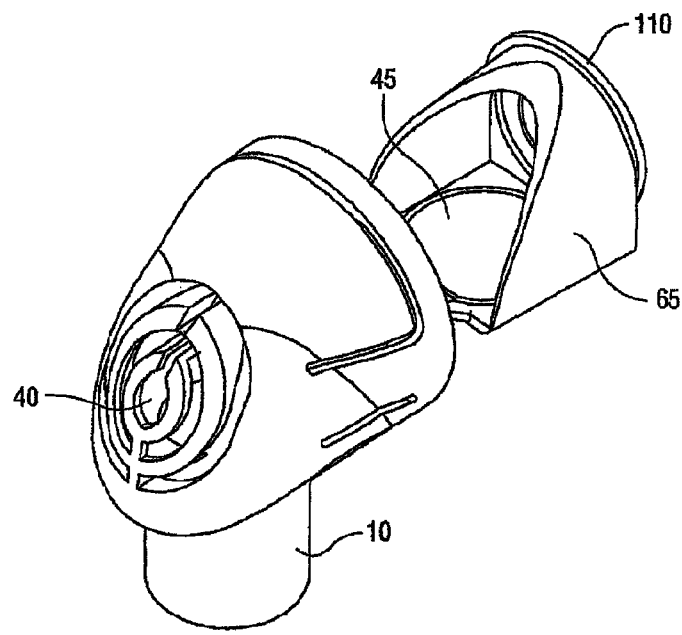
FIGS. 13 and 14 are exploded, perspective views thereof.
Figure 14:
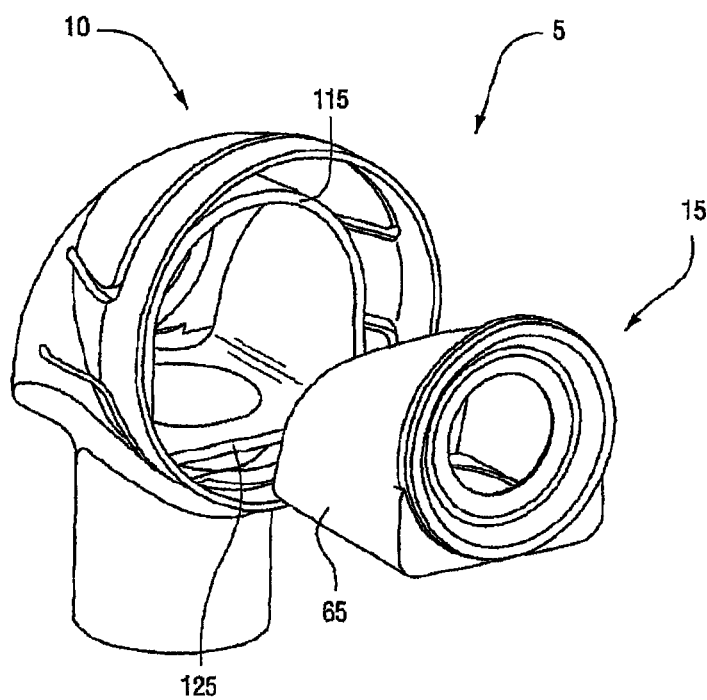

FIGS. 4-9 are enlarged views of the AAV assembly and show further details of the frame assembly, flap portion, base portion, main wall member and side wall members. As seen in FIGS. 4-6, the AAV assembly includes a slightly curved portion which is intended to match the shape of the cylindrical portion of the elbow where the AAV assembly is supported. Further, FIG. 6 shows the tapered side view which is intended to match the shape of the upper portion of the elbow. FIG. 9 shows in more detail the seal lip 90 as well as the connection 105 (e.g., an integral or living hinge) between the flap portion and the base portion. In the illustrated embodiment, the connection 105 is thinner than the flap portion 45, e.g., approximately 0.5 mm. Generally, the AAV assembly forms part of the internal geometry of the elbow. Furthermore, the AAV assembly can perform the functions of an anti-asphyxia valve, elbow-to-frame seal and oxygen diverter valve.

All components of the AAV assembly are formed of a single piece of material in this embodiment. The AAV assembly is preferably formed from a silicone based material, such as molded liquid silicone rubber (LSR). This design suits an open and shut tool with one single core, form which the AAV assembly can be de-molded. However, the AAV assembly may be formed by more than one part of silicone and/or rigid material, e.g., over-molding, mechanical interlock.

1.2 Second Embodiment

FIGS. 10-14 illustrate an elbow assembly 5 according to another embodiment of the invention. This embodiment is similar to the first embodiment, but includes a few changes. The following will provide a description of the main differences between the embodiments, although other differences may be apparent to the skilled artisan. For example, the port 40 shown in FIG. 10 has a slightly different configuration.

The AAV assembly has a very similar manner of operation and structure. However, the AAV assembly is secured in the elbow in a slightly different manner. In particular, while the AAV assembly in the first embodiment is secured (in part) using a bead that protrudes from an outer circumference 75 of the AAV assembly into a groove 80 in the elbow, the AAV assembly in FIG. 12 includes a shoulder 110 that engages with an edge 115 of the elbow 10. The lower end 120 of the main wall member 60 is supported by a surface 125 of the elbow.

1.3 Third Embodiment

Figure 15:
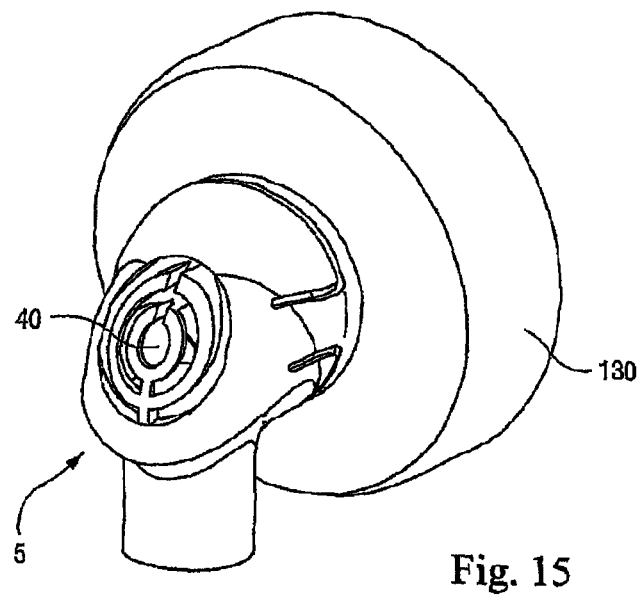
FIG. 15 is a perspective view of a mask assembly according to yet another embodiment of the present invention.
Figure 16:
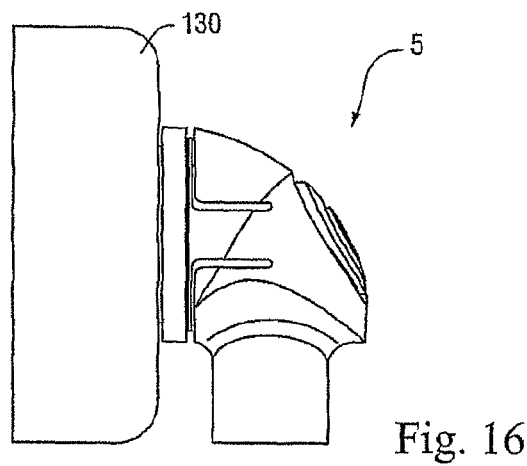
FIG. 16 is a side view thereof.
Figure 17:
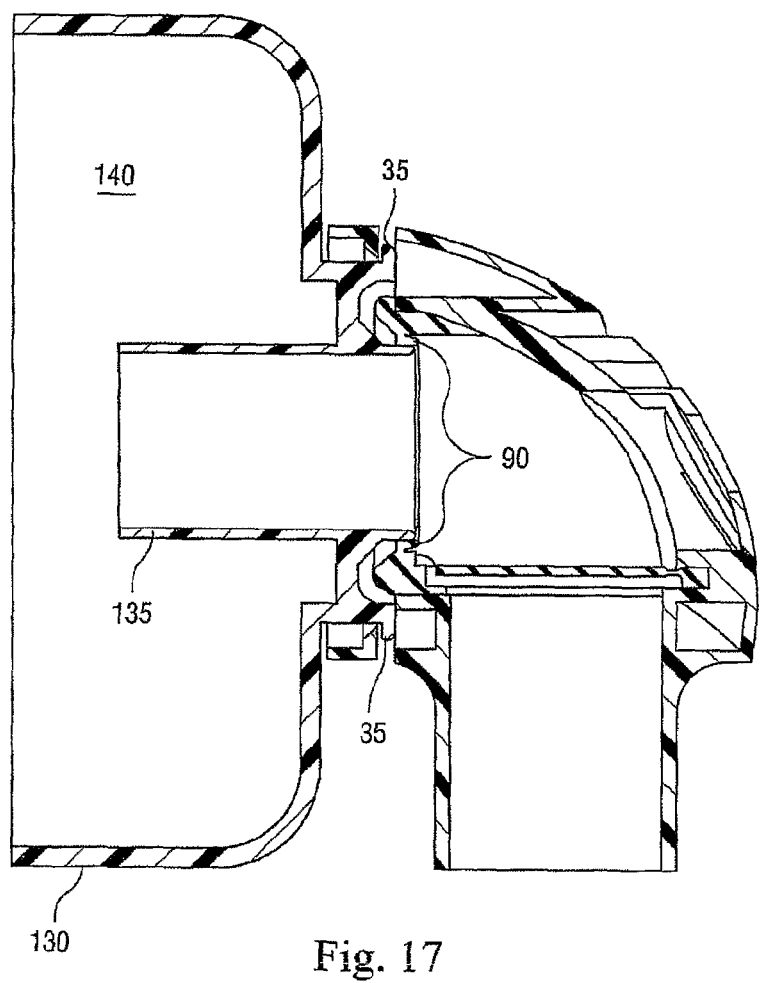
FIG. 17 is a cross-sectional view thereof.
Figure 18:
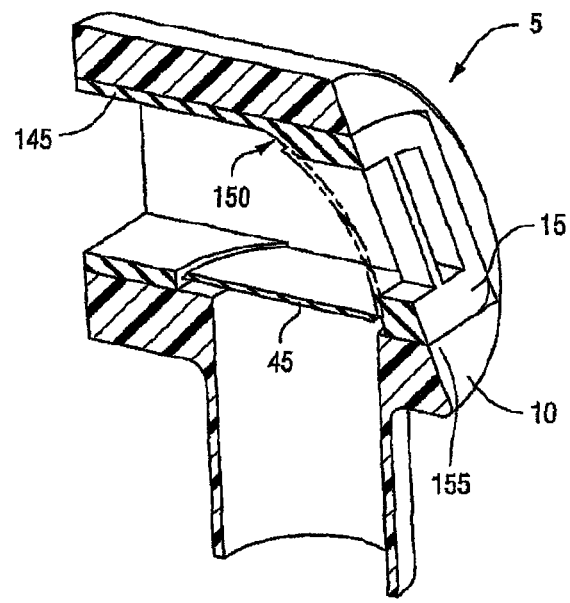
FIG. 18 is a cross-sectional view of an elbow assembly according to still another embodiment of the present invention.

FIGS. 15-17 illustrate an mask assembly according to yet another embodiment of the present invention. In this embodiment, elbow assembly 5 is similar to those described above, but FIGS. 15-17 show the elbow assembly connected to a sample mask frame 130. FIG. 17 is a cross-sectional view showing the interconnection between the frame and the elbow. The flanged collar 35 of the frame 130 is shown in its locked orientation relative to the elbow assembly. Further, the frame 130 includes a baffle portion 135 having an exterior surface that is sealingly engaged by the seal member 90, upon assembly. The baffle portion 135 may extend into the breathing chamber 140 of the mask assembly.

1.4 Fourth Embodiment

Figure 19:
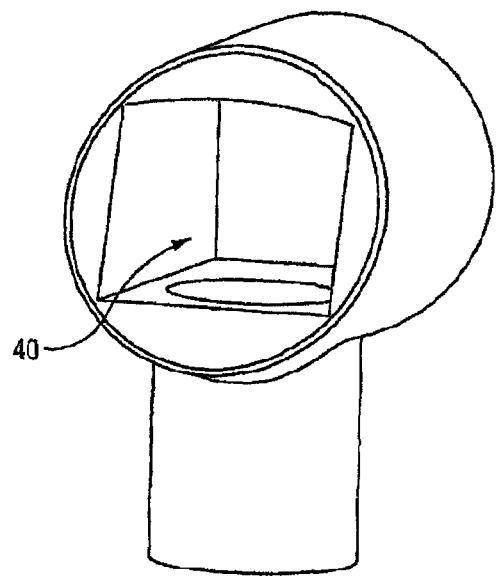
FIG. 19 is a perspective view of the elbow without the AAV assembly.

FIGS. 18-22 illustrate an elbow assembly 5 according to yet another embodiment of the present invention. The elbow as shown in FIG. 19 includes a port 40 that is generally rectangular in shape. Accordingly, the AAV assembly 15 also has a frame assembly having a generally rectangular box-like shape. The frame assembly includes, in addition to an main wall portion 60, side wall portions 65, a flap portion 45 and a base portion 70, a top wall portion 145. The top wall portion 145 includes a stop member 150 limiting the upward maximum amount of movement of the flap portion 45. Main wall portion 60 includes one or more cross members 50.

AAV assembly in this embodiment can be assembled from either the port side or the first portion of the elbow closest to the frame. AAV assembly can be held in place relative to the elbow using friction, and the assembly may also include additional mechanical locking structure and/or glue. The main wall portion 60 is positioned within the port and is generally flush with the exterior surface 155 of the elbow.

Figure 22:
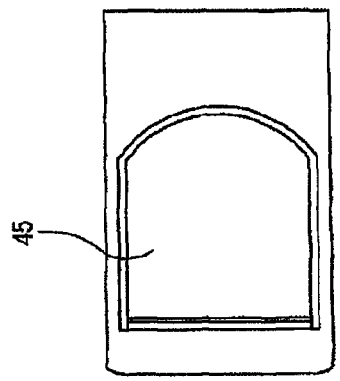
FIG. 22 is a bottom view thereof.
Figure 21:
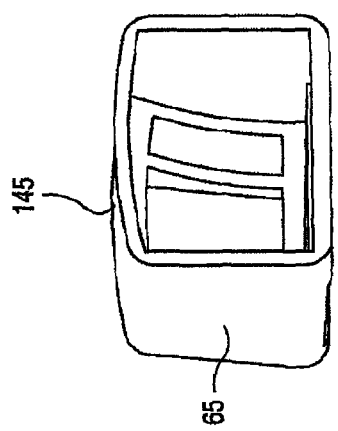
FIG. 21 is another perspective view of the AAV assembly shown in FIG. 18.
Figure 20:
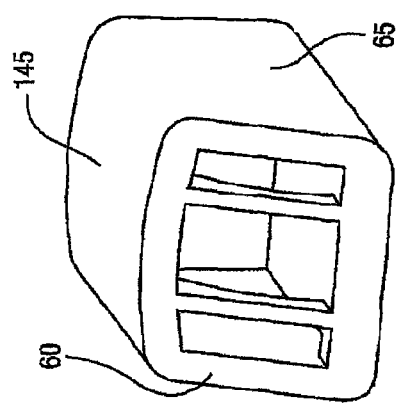
FIG. 20 is a perspective view of the AAV assembly shown in FIG. 18.

FIGS. 20-22 show the AAV assembly in isolation where additional detail can be seen.

1.5 Fifth Embodiment

Figure 25:
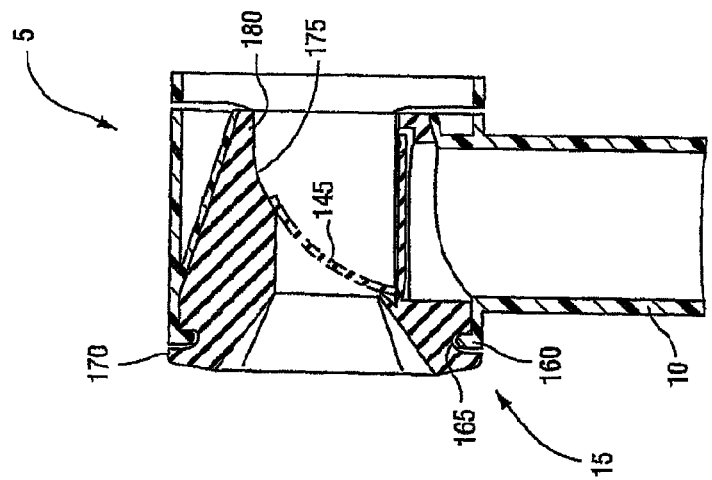
FIG. 25 is a cross-sectional view thereof.
Figure 24:
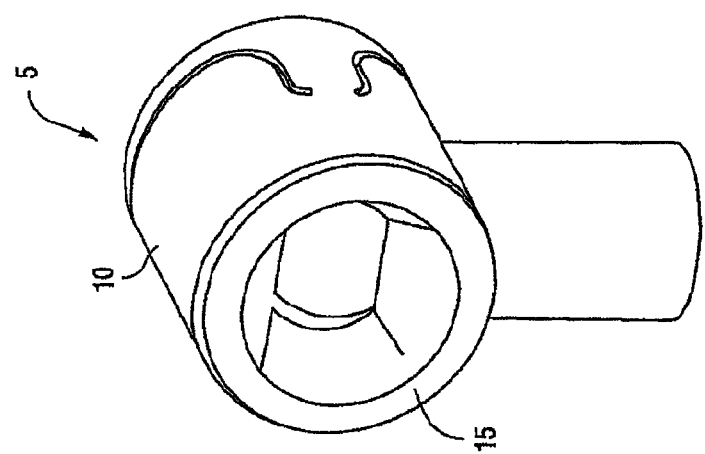
FIG. 24 is a reverse perspective view thereof.
Figure 23:
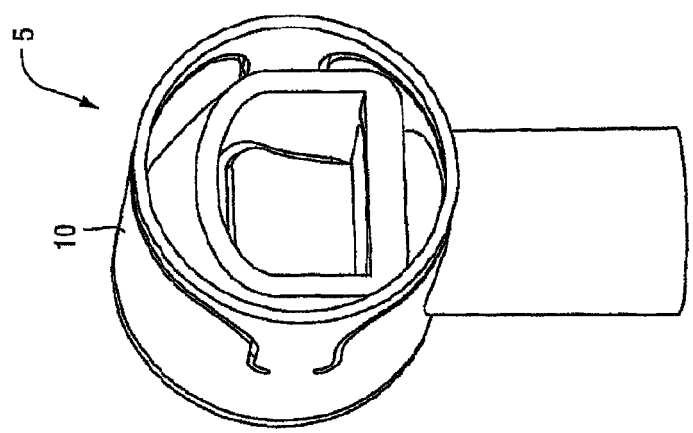
FIG. 23 is a perspective view of an elbow assembly according to another embodiment of the present invention.

FIGS. 23-25 illustrate an elbow assembly 5 according to another embodiment of the present invention. The AAV assembly 15 and the elbow 10 are connected using a tongue and groove arrangement. In this example, the elbow 10 includes a tongue 160 and the AAV assembly includes a groove 165. Once engaged, a portion 170 of the AAV assembly extends beyond the rear end of the elbow 10. The portion 170 is generally cylindrical and matches the shape of the cylindrical portion of the elbow.

The AAV assembly 15 is assembled from the port side toward the first portion of the frame. The AAV assembly includes a top portion that is generally contoured to match the tapered top portion if the interior of the elbow. The top portion includes a stop portion 175 to limit the maximum travel of the flap portion 45. The AAV assembly has a forward portion 180 oriented towards the frame that may sealingly engage a portion of the frame upon connection.

1.6 Sixth Embodiment

FIGS. 26-33 illustrate an elbow assembly according to a further embodiment of the invention. This embodiment may not technically fall under the heading of "'Letter Box' AAV assembly", but is being grouped herewith since there are similarities with the previous embodiment.

Figure 26:
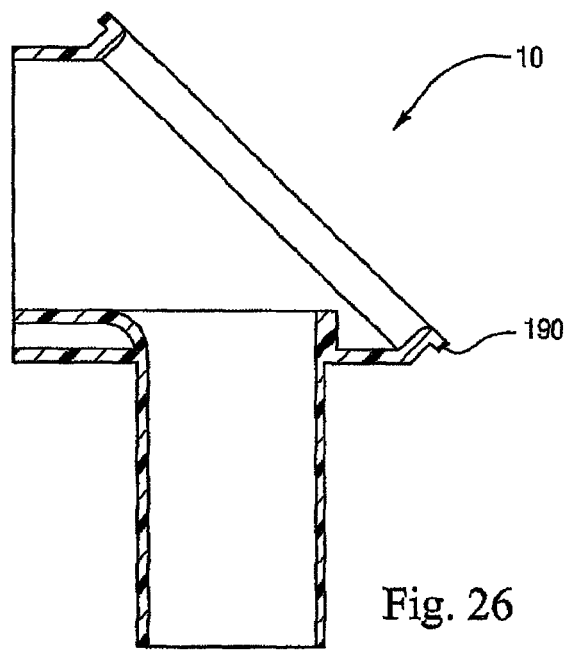
FIG. 26 is a cross-sectional view of an elbow according to another embodiment of the present invention.
Figure 27:
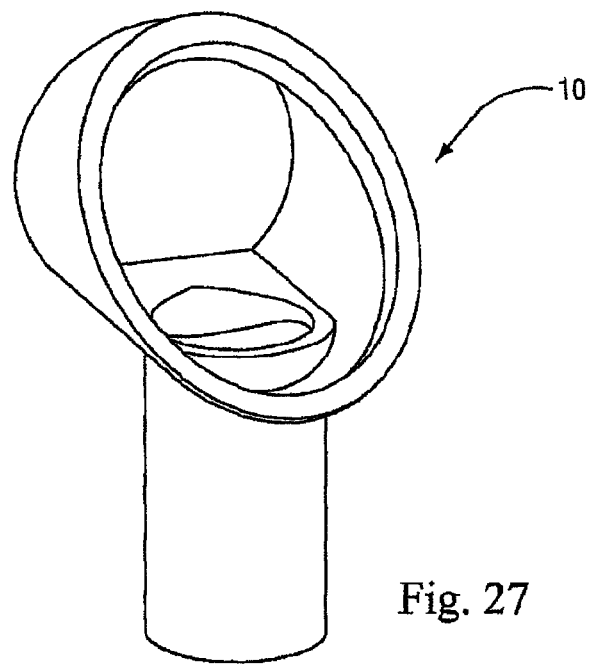
FIG. 27 is a perspective view thereof.
Figure 28:
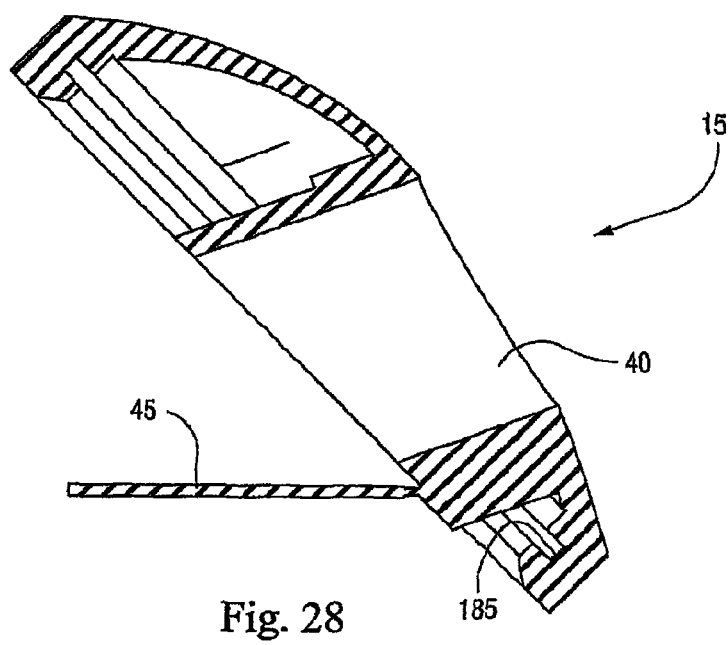
FIG. 28 is a cross-sectional view of an AAV assembly for use with the elbow shown in FIGS. 27 and 28.
Figure 29:
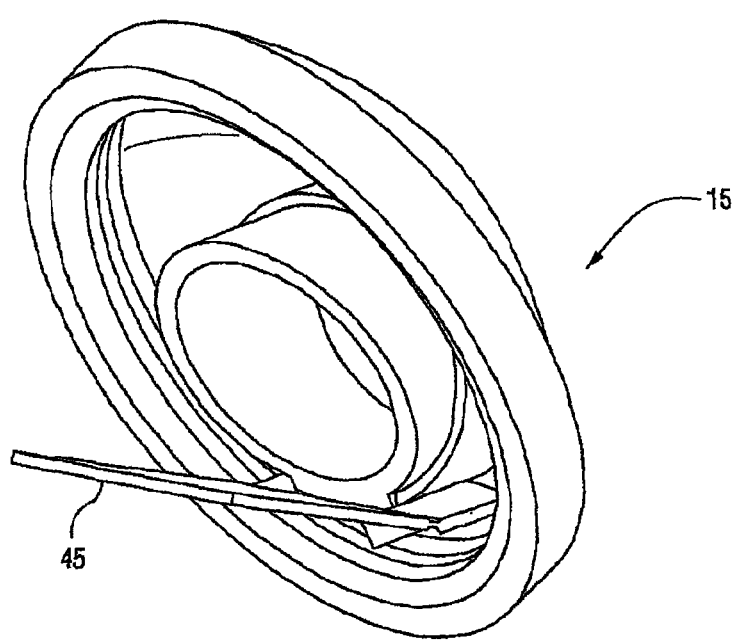
FIG. 29 is a perspective view thereof.
Figure 30:
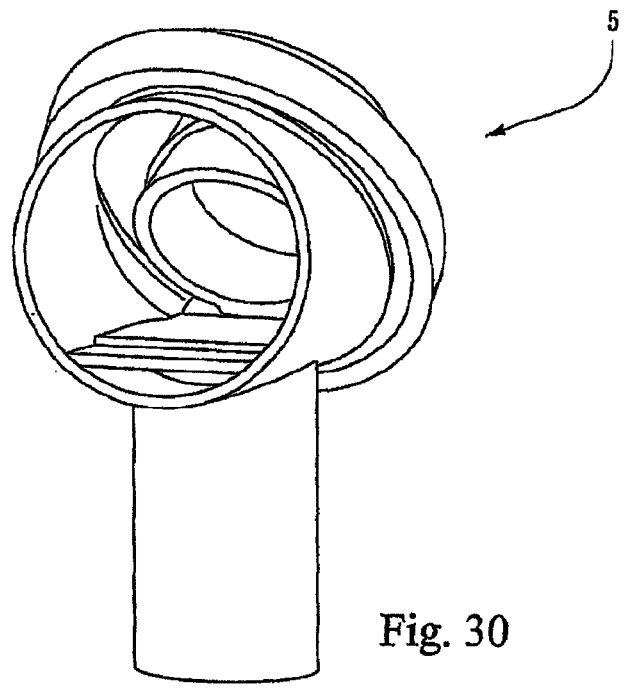
FIG. 30 is a perspective view of the elbow assembly.
Figure 31:
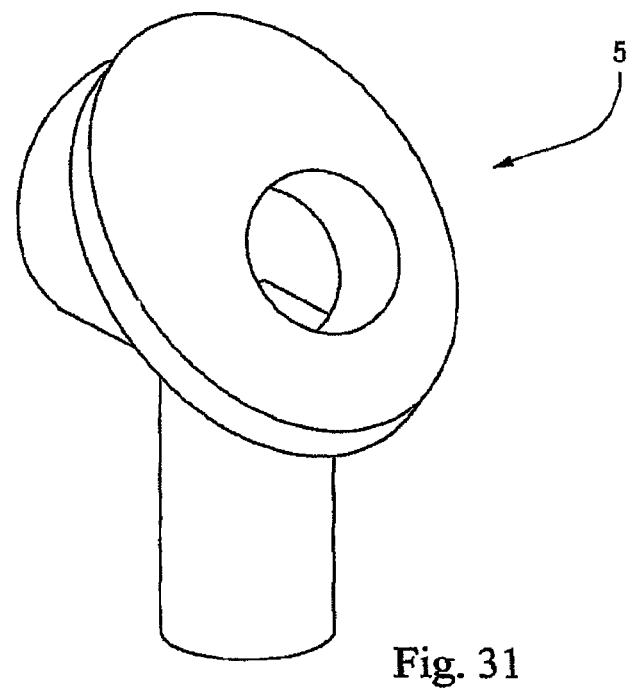
FIG. 31 is a reverse perspective view thereof.
Figure 32:
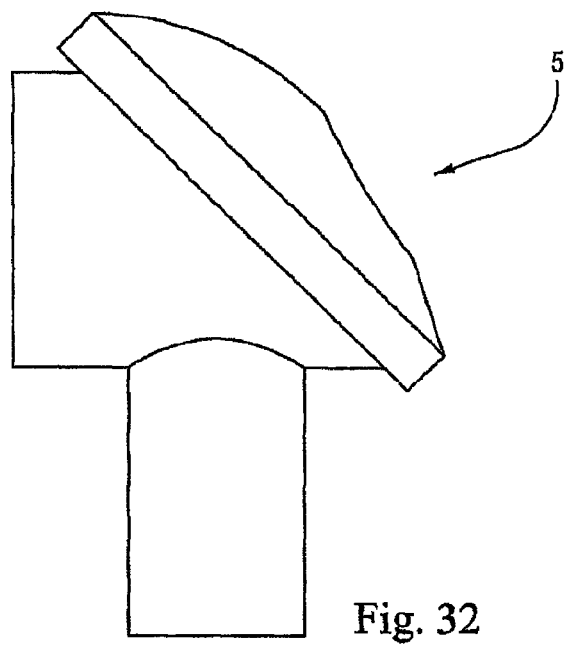
FIG. 32 is a side elevation view thereof.
Figure 33:
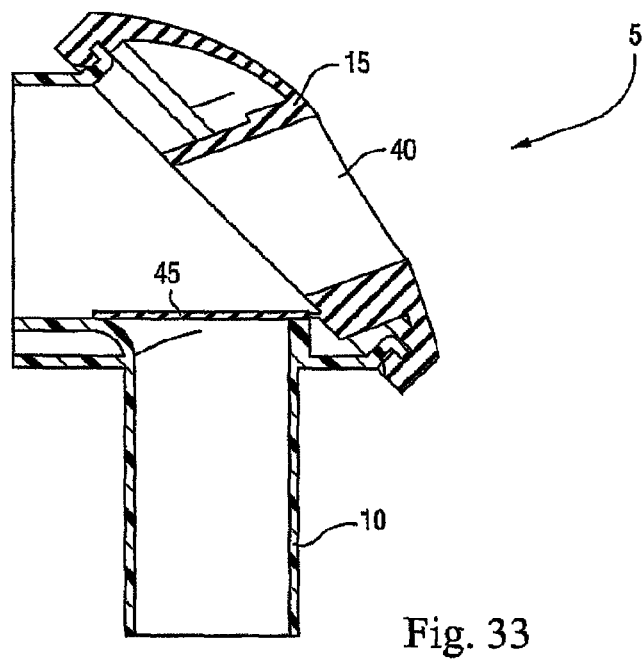
FIG. 33 is a cross-sectional view thereof.
Figure 34:
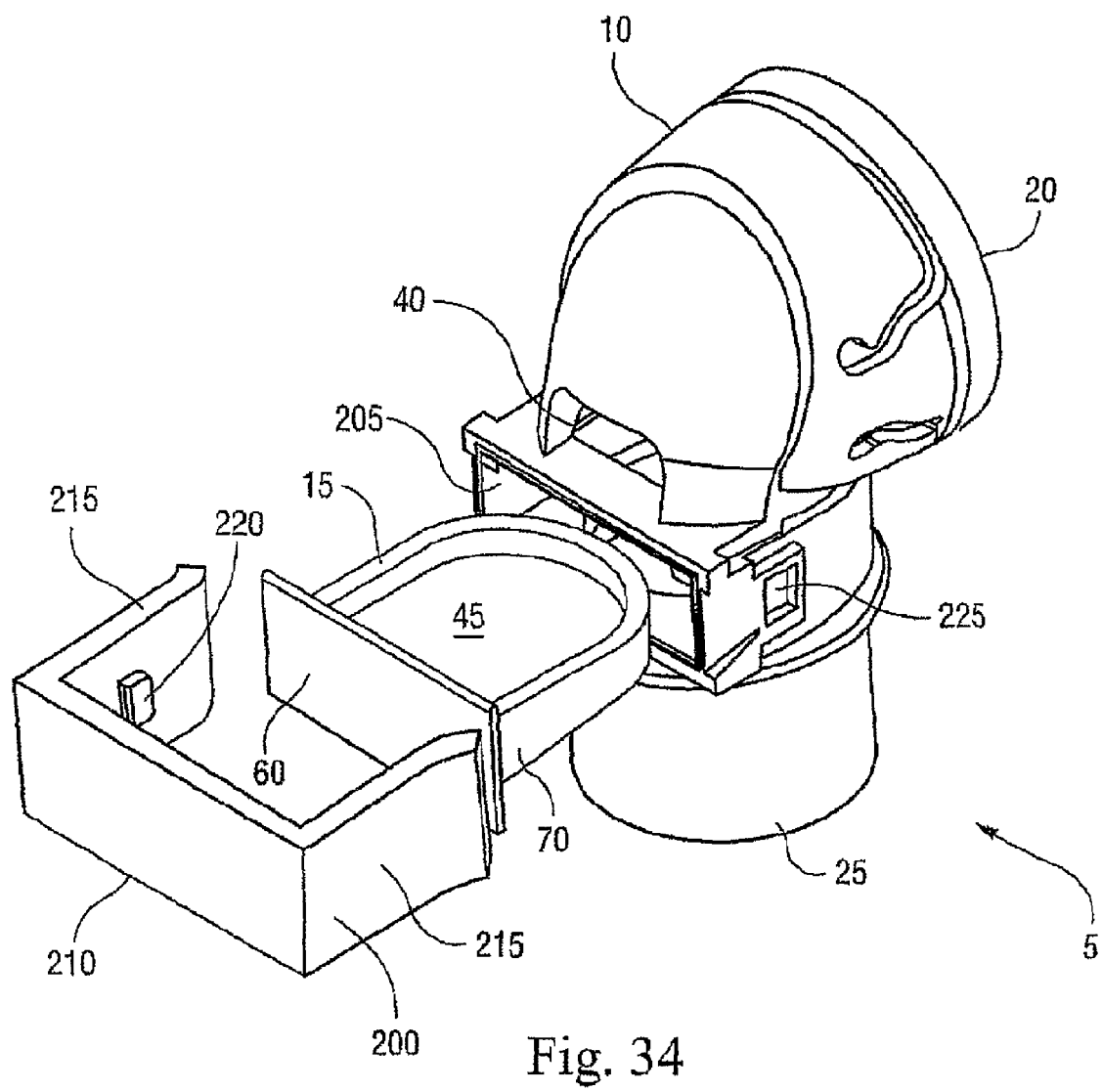
FIG. 34 is an exploded perspective view of an elbow assembly according to another embodiment of the present invention.

FIGS. 26-27 show the elbow 10, FIGS. 28-29 show the AAV assembly 15, and FIGS. 30-33 show the elbow/AAV assembly 5. The AAV assembly 15 and elbow 10 are connected using a tongue and groove 185 arrangement, where the AAV assembly includes a groove that receives a tongue or flange 190 of the elbow. As shown in FIG. 28, the AAV assembly includes a flap portion 45 and defines the port 40. The flap portion 45 rests on interior features of the elbow, as shown in FIG. 33.

2.0 Slot-In AAV Assembly

2.1 First Embodiment

FIGS. 34-47 are directed towards an elbow assembly 5 according to another embodiment of the present invention. Elbow assembly includes an elbow 10, an AAV assembly 15 and a clip member or portion 200 to secure the AAV assembly 15 to the elbow 10.

Elbow 10 includes a first portion 20 and a second portion 25, as described above. Elbow also includes a slot 205, just below the port 40, that is structured to receive the AAV assembly 15.

Figure 36:
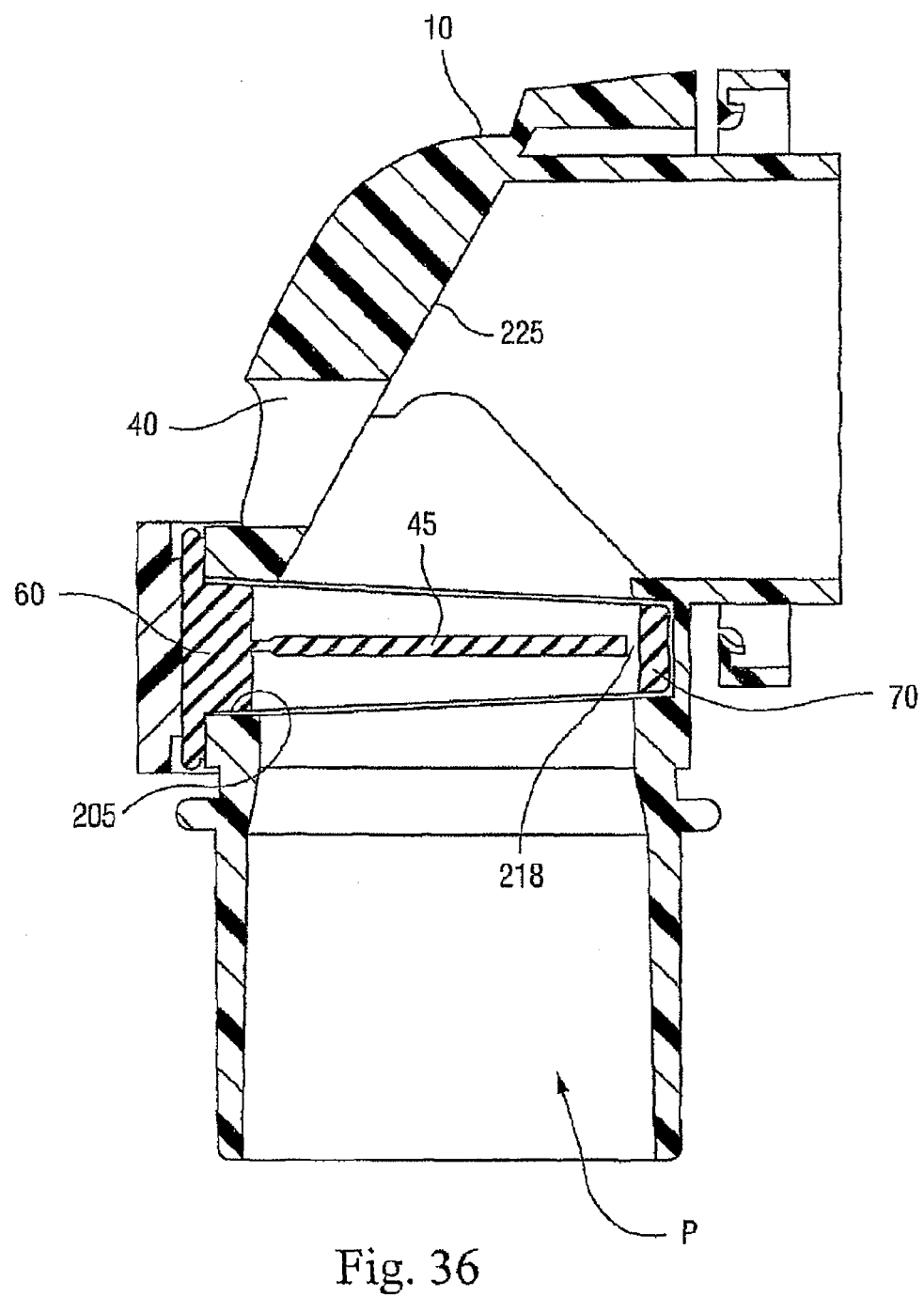
FIG. 36 is a cross-sectional view thereof.

As best shown in FIG. 36, the slot 205 is formed by a ledge. The ledge supports the AAV assembly 15 during use, guides assembly and disassembly, and prevents misassembly (i.e., back to front). That is, the upper ridge and lower surface in the elbow form a housing which acts as a lead-in for the AAV assembly 15 and supports the outer edge of the AAV assembly 15 in use.

AAV assembly 15 is preferably molded LSR. AAV assembly includes an main wall member 60 and a base portion 70 that extends away from the main wall member 60. A flap portion 45 is hingedly connected to the main wall member (FIG. 36). AAV assembly is generally D-shaped in profile (FIG. 39), and generally trapezoidal from the side (FIG. 36). This helps to prevent assembly in the wrong way and ensures assembly in the correct manner.

Figure 35:
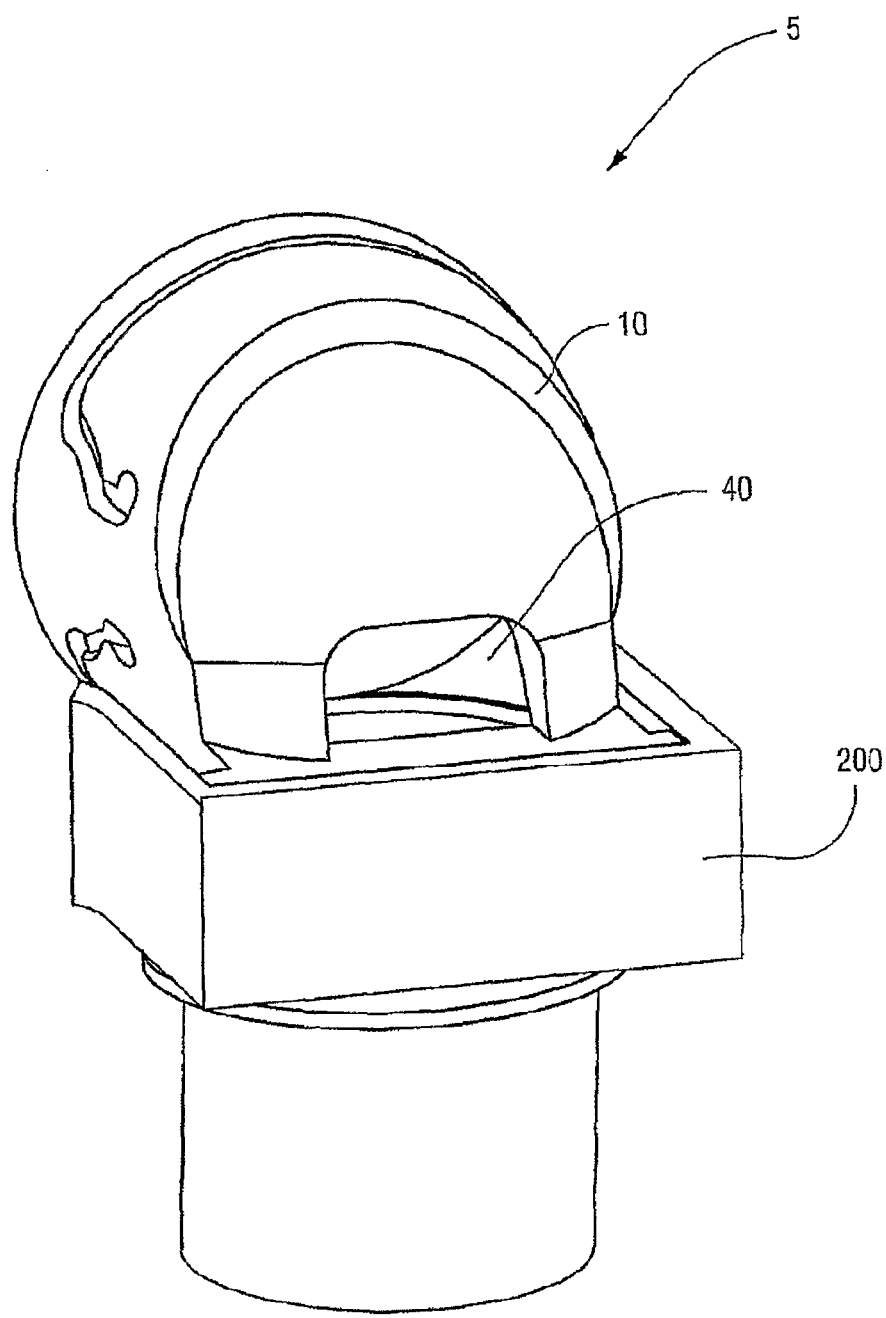
FIG. 35 is an assembled view thereof, from a different perspective.

The clip member 200 has a generally U-shape. Clip member 200 has a central wall 210 and two arms 215. Each arm 215 includes a protrusion 220 to lockingly engage with a corresponding recess 225 formed in the sides of the elbow 10. The assembled condition of the elbow/AAV assembly is shown in FIGS. 35 and 36. In FIG. 36, it can be seen that the flap portion 45 can move to selectively cover the port 40, depending on the presence of pressurized gas p.

Both the clip member 200 and AAV assembly 15 have symmetrical shapes which allows both of them to be properly assembled in either vertical orientation, i.e., the clip member can be turned upside down without affecting operation. If the flap portion 45 gets caught upon assembly, the clip member will not slot-in, which provides for fail safe assembly. When the clip member 200 is fully located with in slot 205 with the arms 215 locked in place, an audible and/or tactile 'click' is observed, confirming full assembly—to act as feedback for the user.

The outer part (or base portion 70) of the flap portion 45 may be solid (e.g., part of overmold). The gap 218 between the outer part 70 and the moving flap portion 45 should be relatively small, e.g., about 0.5-1 mm or about 0.75 nm, to prevent oxygen or other gases from being delivered to the patient from the flow generator, and/or to prevent rebreathed $CO_2$ accumulating in the tube, when the flap portion 45 is not activated.

The interior surface 225 of the elbow 10 that engages the flap portion 45 is preferably flat to provide an improved sealing mechanism by preventing inadvertent disassembly through pressure on the reverse side. The flat surface also assists in reducing inadvertent deactivation or flutter, and helps the flap portion to activate at a lower pressure. The flap portion moves through an angle of about 20-90 degrees, 50-70 degrees, or about 60 degrees, by engaging the flat surface at that angle. This angle helps entry impedance of the air to the mask and also improves the compactness of the design. The flat surface also promotes smooth flow entering the mask and reduces noise and turbulence.

In the example shown in FIG. 36, the elbow assembly is dimensioned as follows:

Surface area of the flap portion: about 250 $mm^2$—area promotes activation at lower pressures Area of port (or atmospheric hole): about 100 $mm^2$—maximize size of hole to accommodate the flap portion and allow area for sealing (may also be suitably sized to activate at lower pressures)

Angle of port: greater than 45 degrees; about 60 degrees

Overlap of flap portion over port: about 1.4-2.9 mm (varies with position)

Height of flap portion: about 1 mm

Hinge height: 0.1-0.9 mm, preferably about 0.4-0.6 or about 0.5 mm

Hinge length: about 5-20 mm, preferably about 15-17 mm

It should again be noted that these dimensions are examples only, and the dimensions could be modified depending on application. For example, the dimensions could vary up to ±20% of the values provided.

Figure 37:
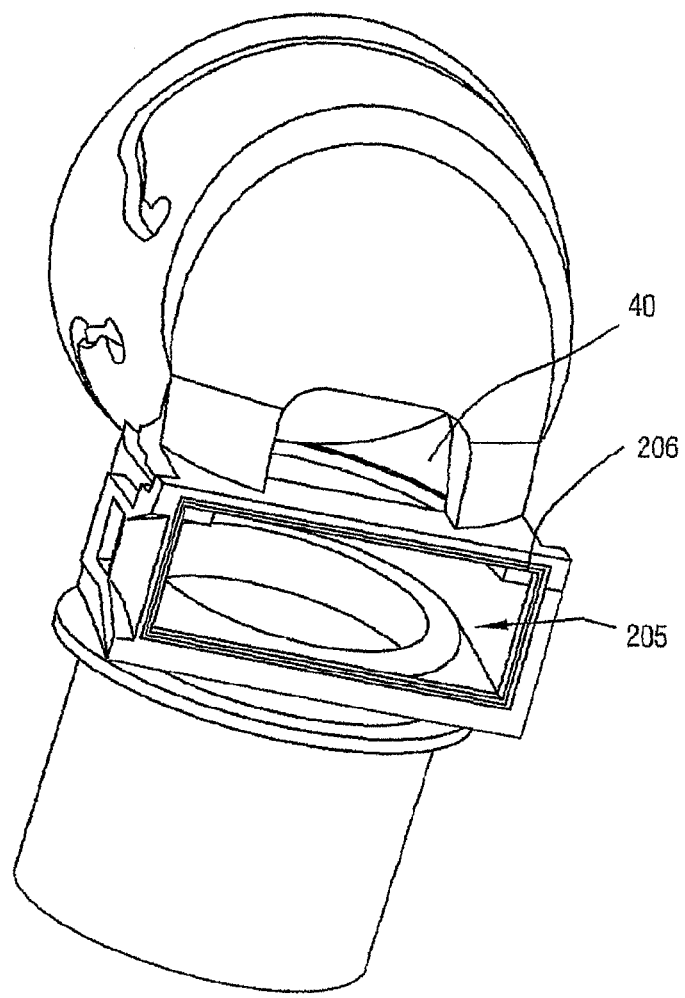
FIG. 37 is a perspective view of the elbow without the AAV assembly.
Figure 38:
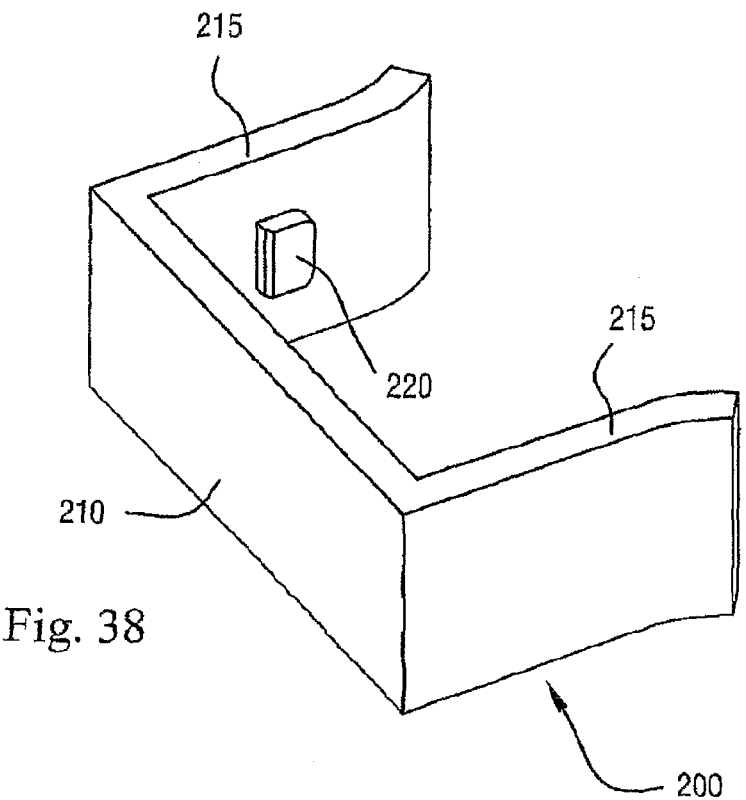
FIG. 38 is a perspective view of the clip member shown in FIGS. 34-36.
Figure 39:
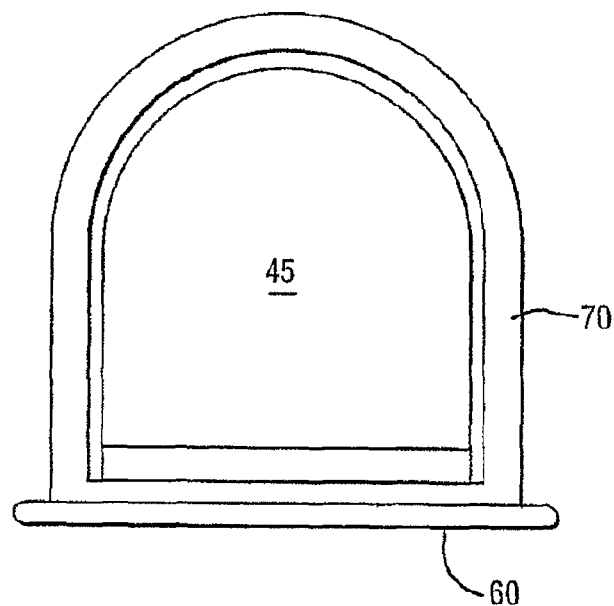
FIG. 39 is a plan view of the AAV assembly in isolation.

FIG. 37 shows the elbow in isolation, in which the slot 205 is clearly visible. As illustrated, a bead feature 206 is provided outside the slot 205. The bead feature 206 provides a sealing feature between the elbow and the wall member 60 of the AAV assembly 15. FIG. 38 shows the clip member 200 in isolation, while FIG. 39 shows the AAV assembly 15 in isolation.

The AAV assembly 15 and the clip member 200 may be made separately and assembled as described above or the clip member and AAV assembly may be initially combined into a sub-assembly and then inserted into the slot of the elbow. Combining of the AAV assembly and the clip member can be achieved using various expedients, such as over-molding, gluing, mechanical lock, etc. The clip member may be an overclip member or a push fit clip, e.g., one that clips to internal structure of the elbow.

Figure 40:
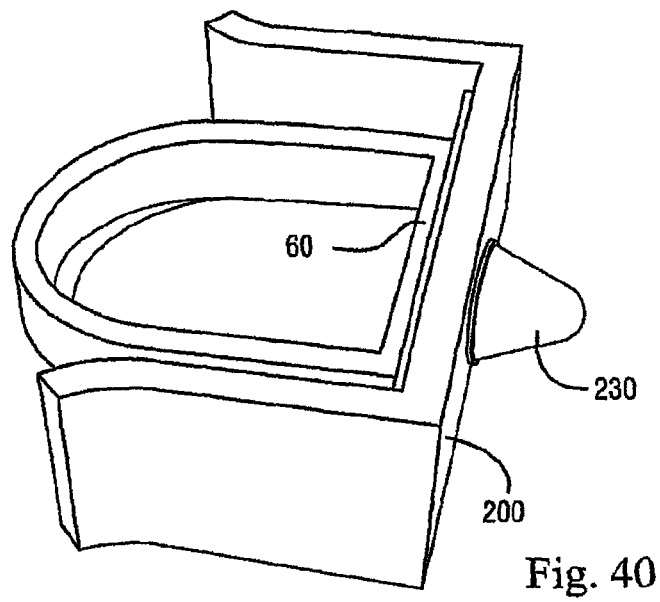
FIG. 40 is a perspective view of a clip/AAV assembly.
Figure 41:
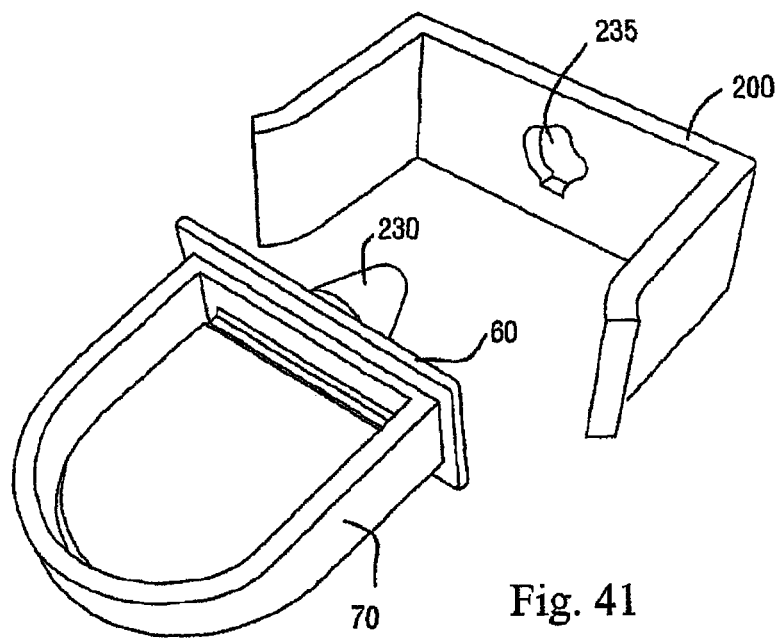
FIG. 41 is an exploded perspective view thereof.
Figure 43:
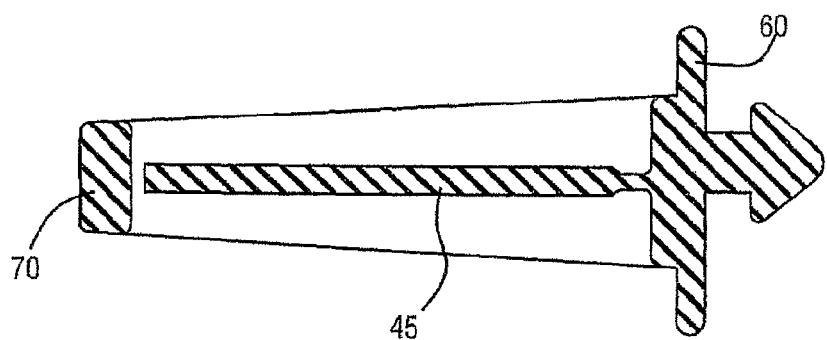
FIG. 43 is a cross-sectional view of the AAV assembly shown in FIG. 41.

One example of a mechanical lock method is shown in FIGS. 40-41. In this embodiment, the main wall member 60 of the AAV assembly includes a locking leg 230 integrally molded with the AAV assembly. The AAV assembly, including the locking leg, is preferably made from LSR. The locking leg includes an enlarged head portion that protrudes through a hole 235 in the central wall of the clip. The head portion expands once through the hole to lock the AAV assembly to the clip. FIG. 43 shows a cross section of the clip member with the locking leg.

Figure 42:
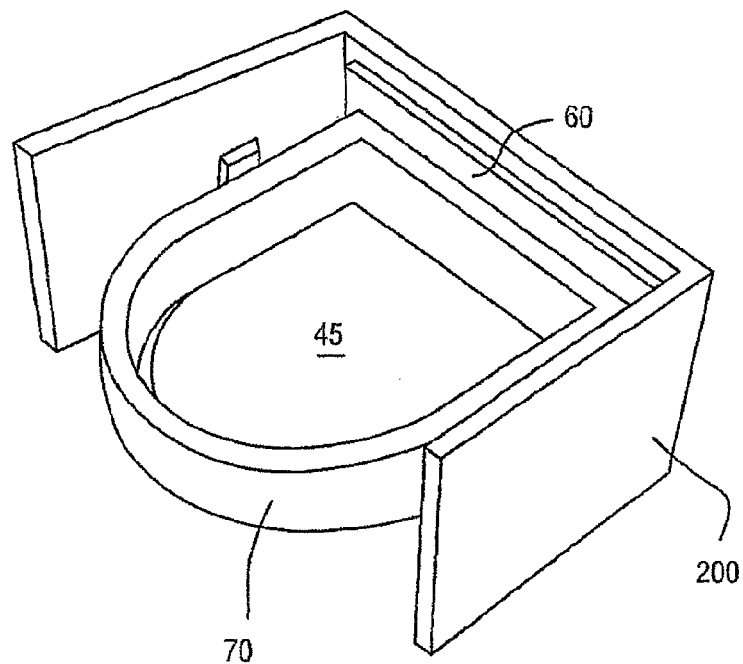
FIG. 42 is a perspective view of an over-molded clip/AAV assembly according to an embodiment of the present invention.

FIG. 42 shows an example of an over-molded clip/AAV assembly. This is a relatively permanent connection method, unlike the mechanical connection described in relation to FIGS. 40-41.

Figure 44:
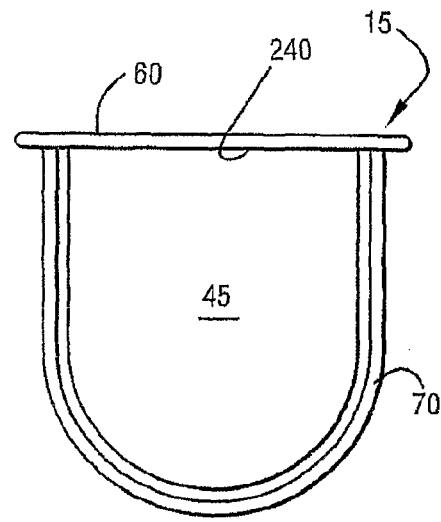
FIGS. 44-47 illustrate several different embodiments of AAV assemblies having different hinge arrangements.
Figure 45:
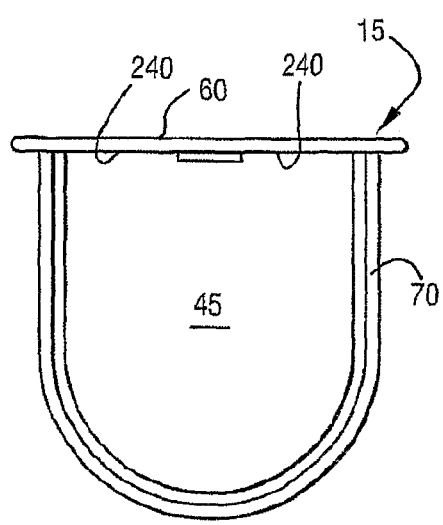
Figure 46:
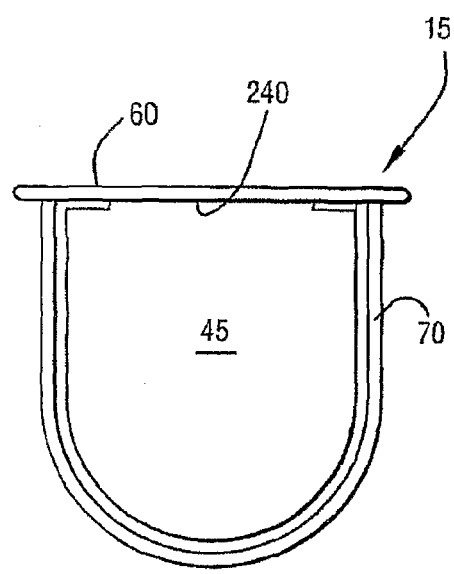
Figure 47:
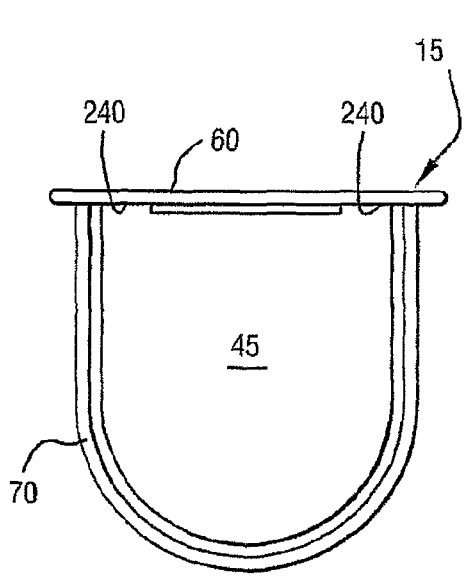

FIGS. 44-47 show various embodiments in which there is a variation on the hinge 240. The length of the hinge 240 modifies the activation/deactivation pressure. The hinge could be straight across, with gaps at the ends, or a gap in the middle. While none of these embodiments use a locking leg, it is to be understood that each could be formed with such. FIG. 44 is the case where the hinge between the flap portion and the main wall member extends over substantially the entire length of the flap portion. FIG. 45 includes a small gap near the central portion of the flap portion. FIG. 46 includes a large central hinged portion, while the end portions include gaps. FIG. 47 is the opposite arrangement where the hinges are only formed along the end portions. It is to be understood that "hingedly connected" also encompasses the situation where the flap portion merely bends relative to its support. Moreover, the flap portion could be arranged to move in a more linear fashion, and is thus not limited to bending or pivoting movement.

2.2 Second Embodiment

Figure 48:
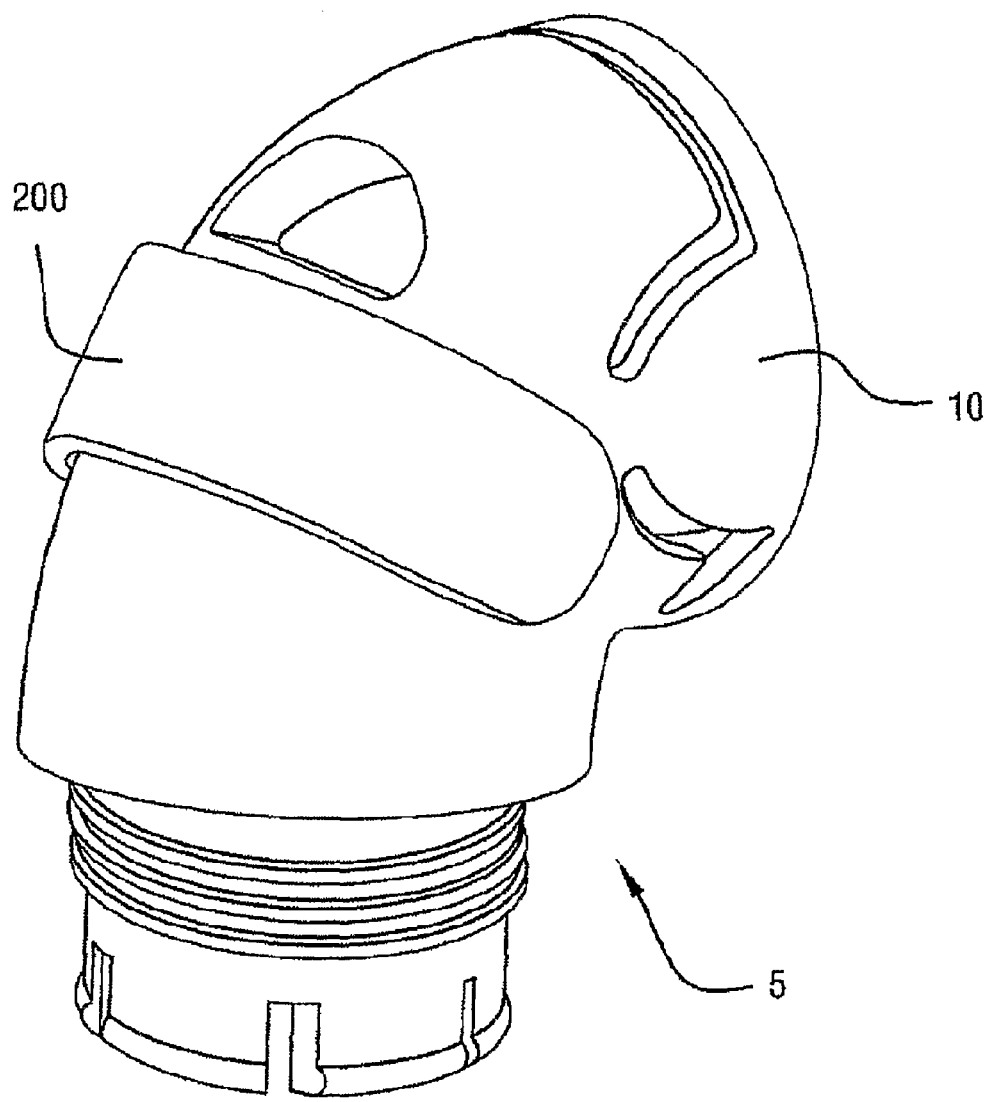
FIG. 48 is a perspective view of an elbow assembly according to another embodiment of the present invention.
Figure 49:
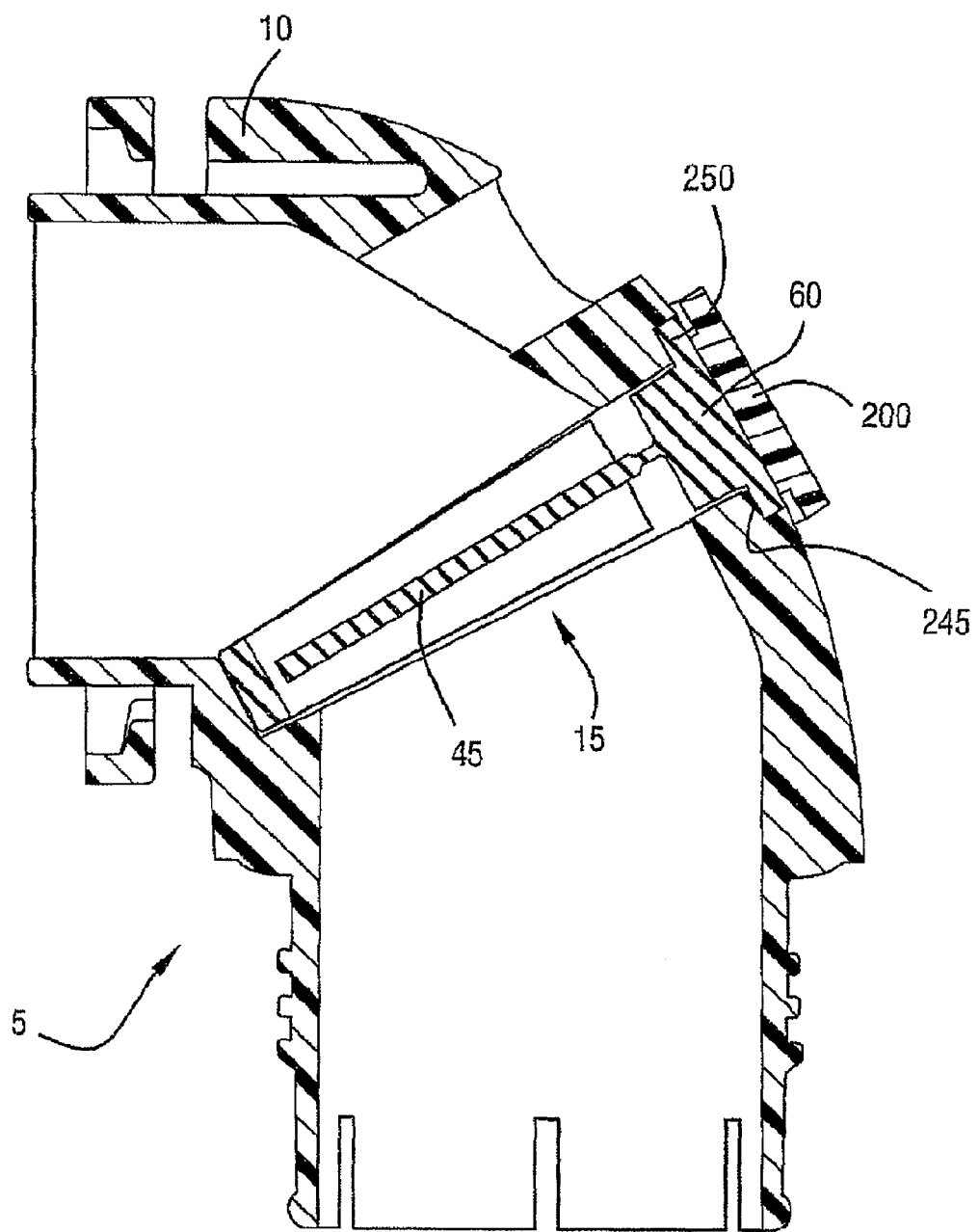
FIG. 49 is cross-sectional view thereof.

FIGS. 48-49 show an elbow assembly 5 according to an alternative embodiment of the present invention. In particular, cross-sectional FIG. 49 illustrates how the AAV assembly 15 is seated relative to the elbow 10. The elbow 10 includes a shoulder 245 that supports the flanged portion 250 of main wall member 60 such that the flanged portion is flush with the outer surface of the elbow. The clip member 200 is positioned over the AAV assembly to hold it in place relative to the elbow. The clip member and AAV assembly may be connected via a tongue and groove arrangement or a snapping arrangement. The clip member may "snap" in place to provide confirmation of correct assembly to the user.

2.3 Third Embodiment

Figure 50:
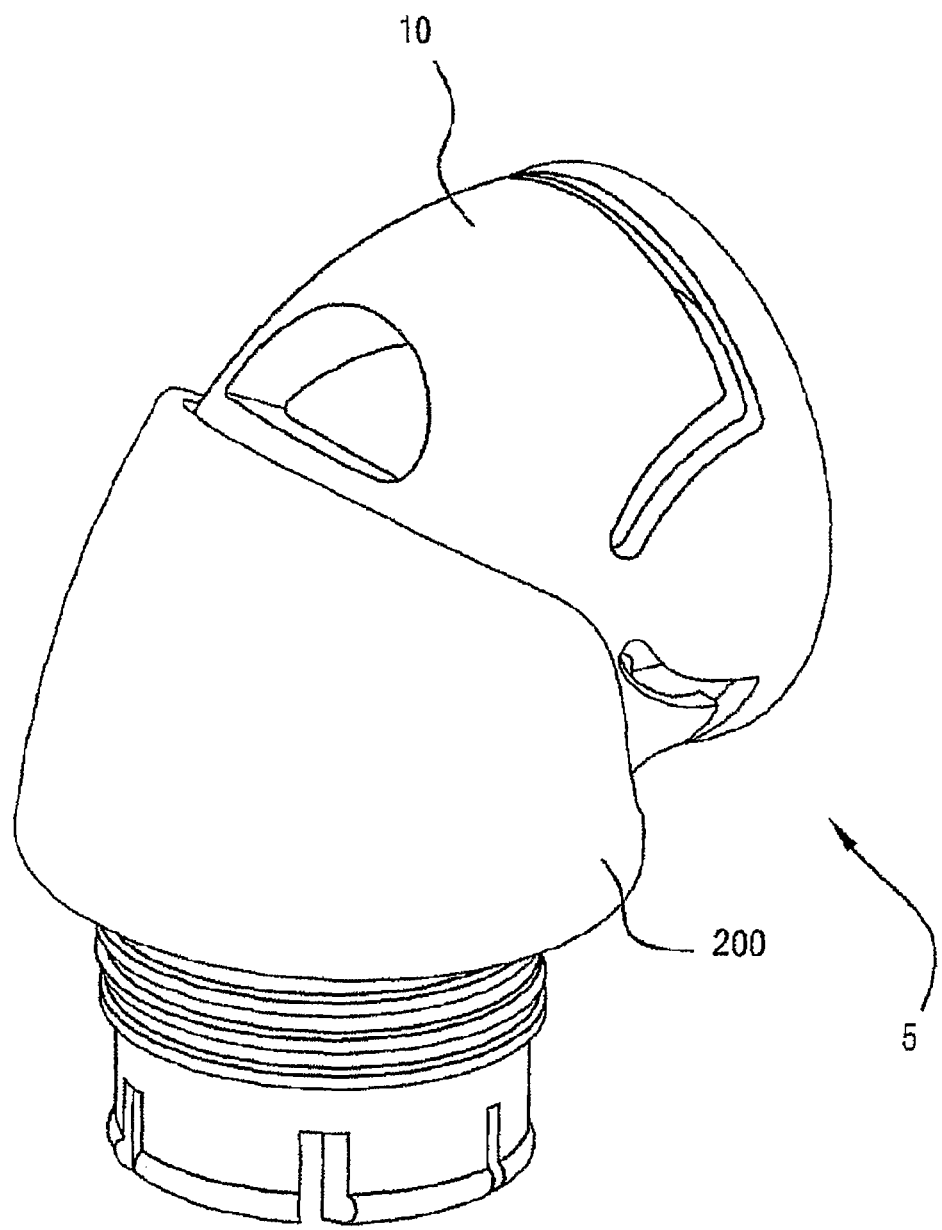
FIG. 50 is a perspective view of an elbow assembly according to another embodiment of the present invention.
Figure 51:
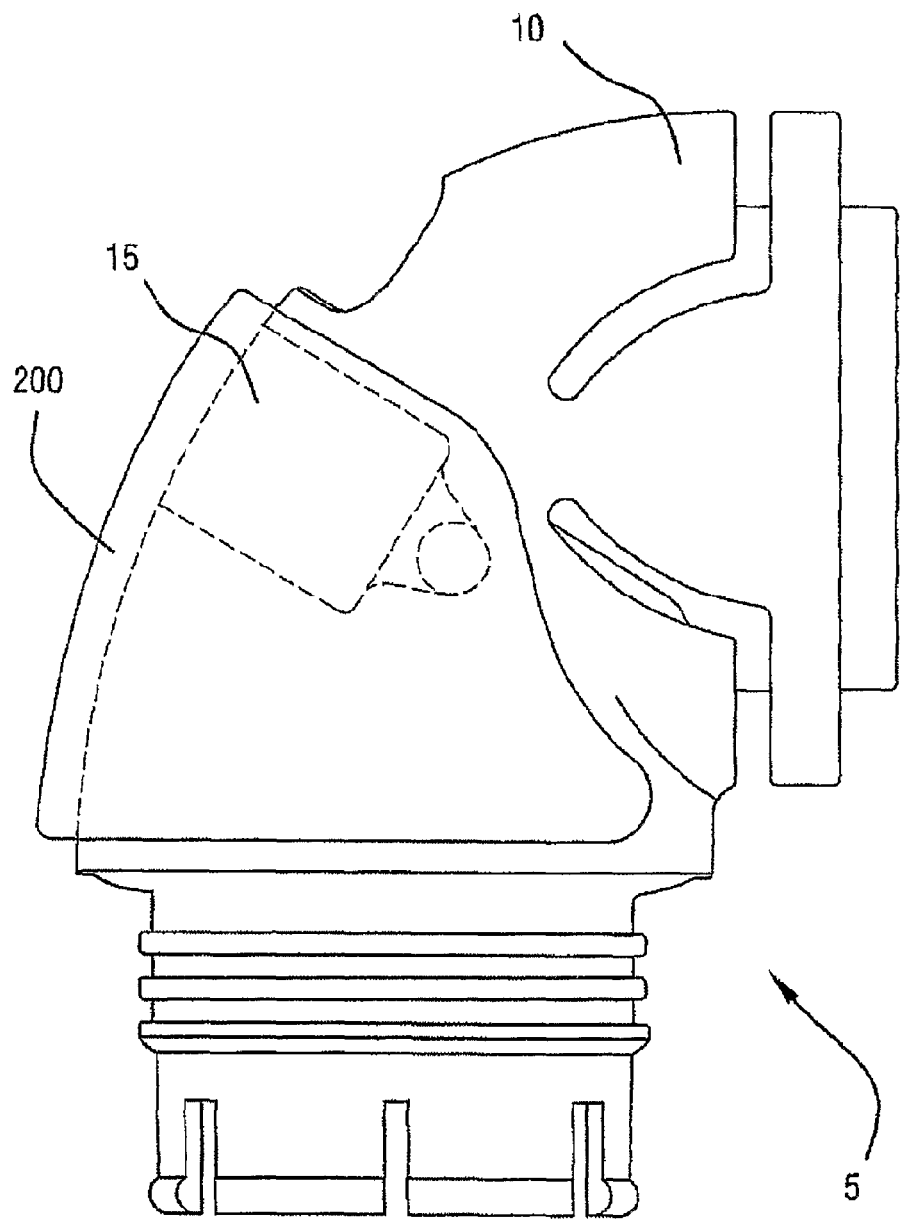
FIG. 51 is a side view thereof.
Figure 52:
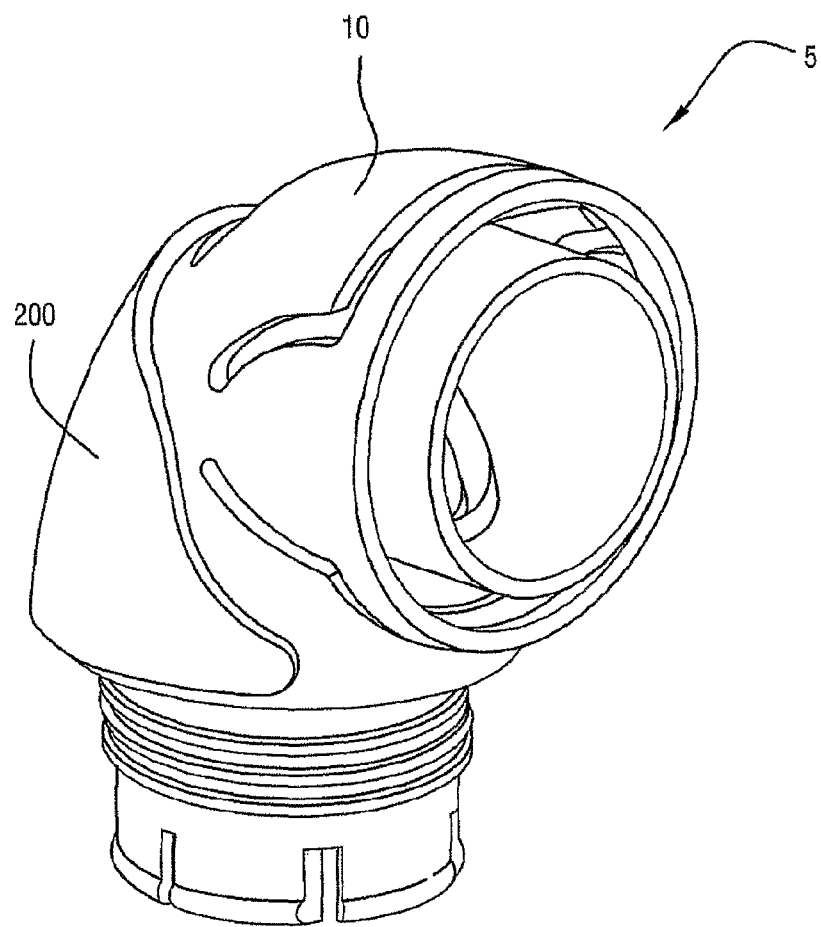
FIG. 52 is a reverse perspective view thereof.

FIGS. 50-52 show an elbow assembly according to yet another embodiment of the present invention. This embodiment is similar to the above embodiment but includes a shroud-like clip 200.

2.4 Fourth Embodiment

Figure 53:
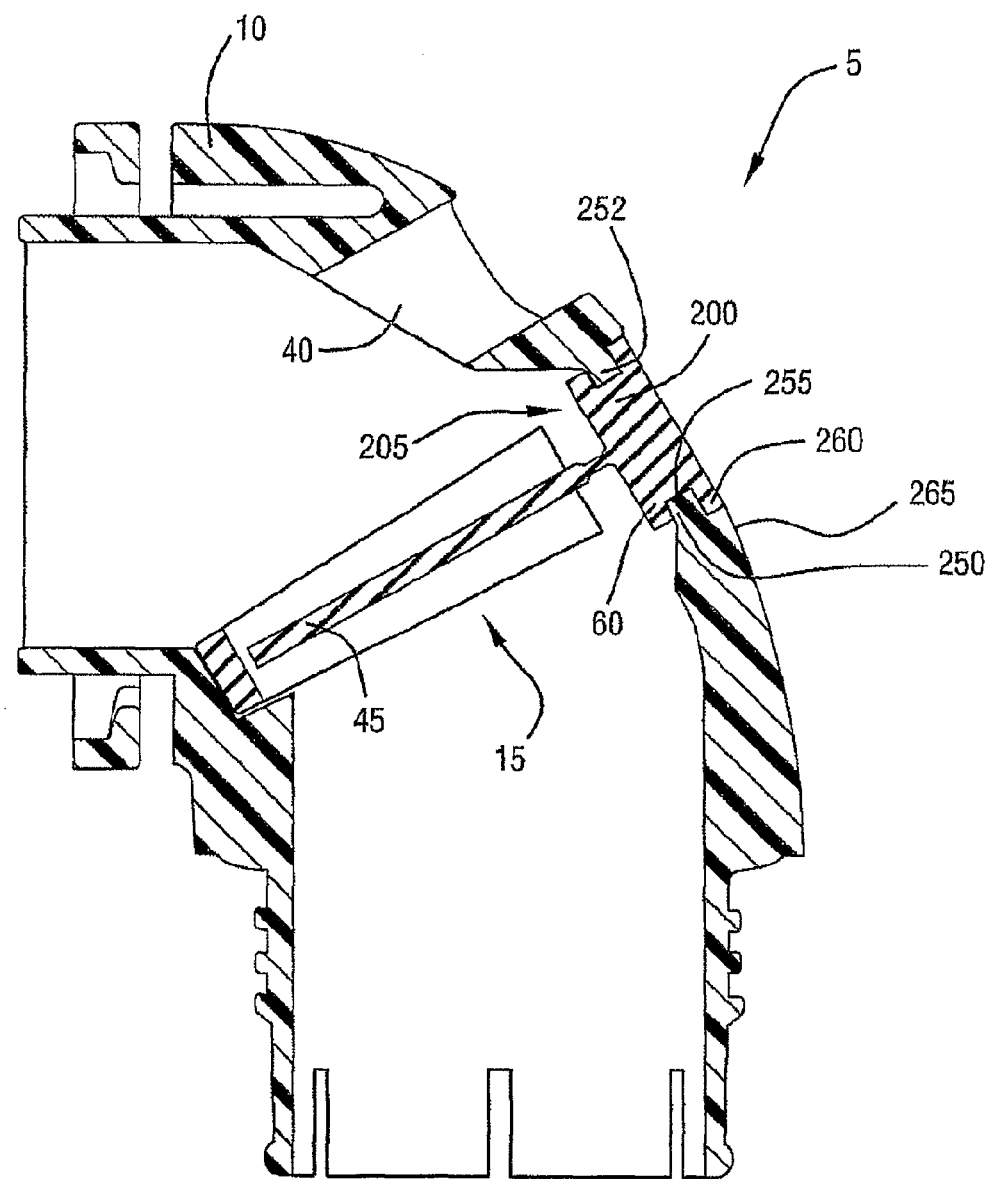
FIG. 53 is a cross-sectional view of an elbow assembly according to another embodiment of the present invention.
Figure 54:
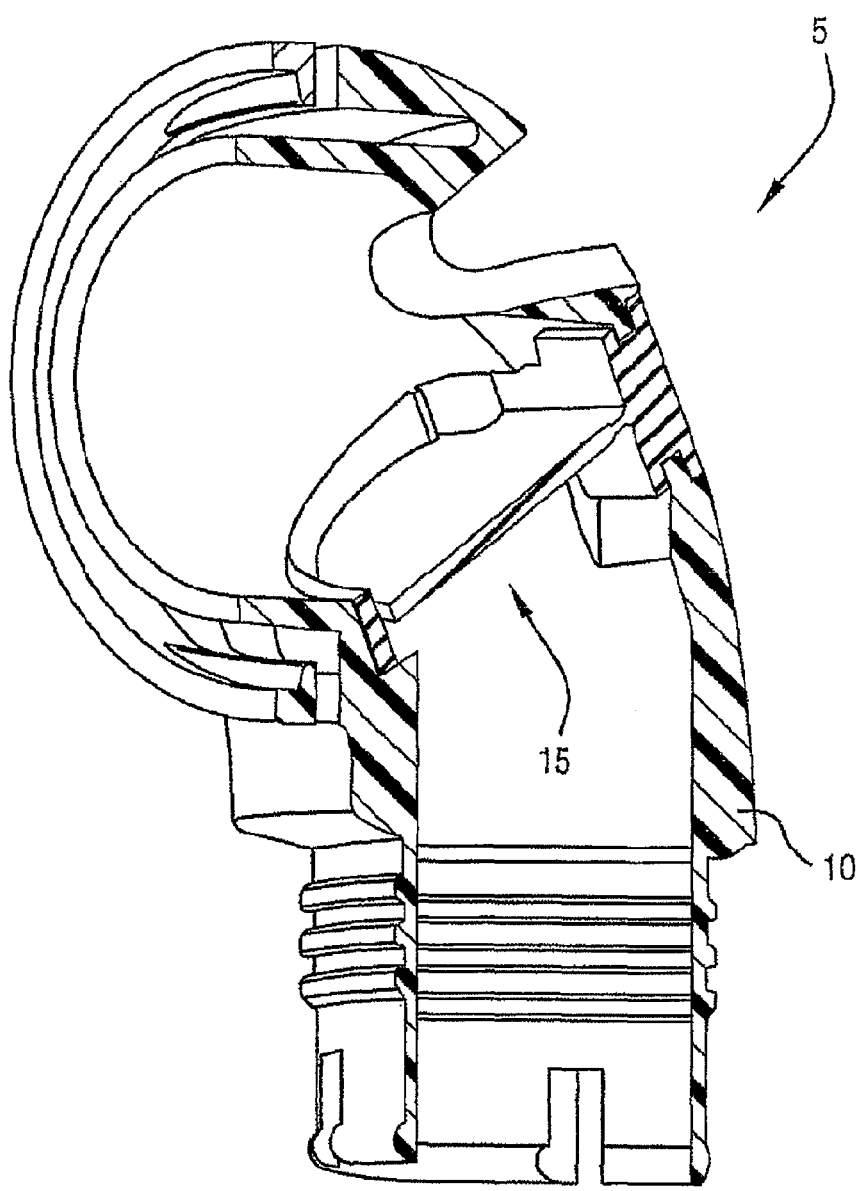
FIG. 54 is a cross-sectional view thereof from a different perspective.
Figure 55:
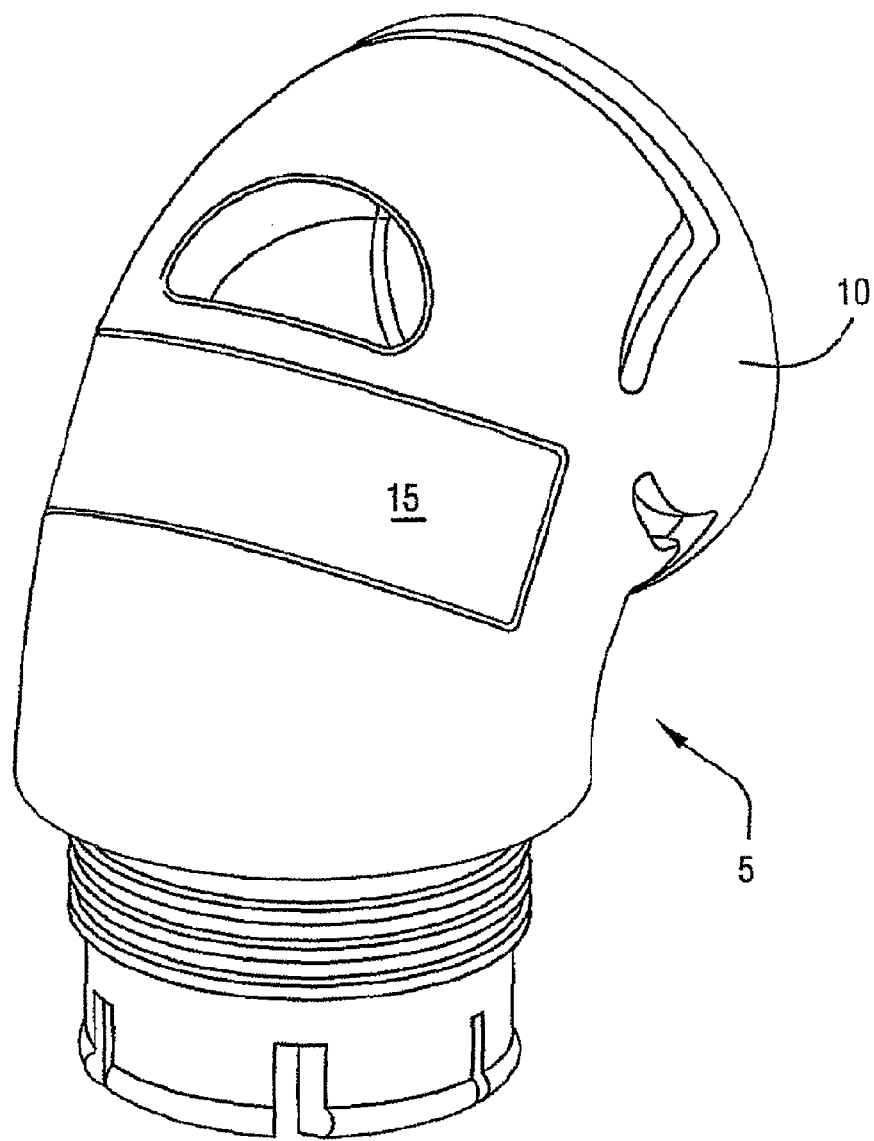
FIG. 55 is rear perspective view thereof.

FIGS. 53-55 illustrate an elbow assembly according to still another embodiment of the present invention. In this embodiment, the clip member or portion 200 is formed as part of the AAV assembly 15, thus eliminating a part. The main wall member 60 includes a clip portion 200 that is directly connected to the elbow 10 by inserting a rim 252 of the elbow surrounding the slot 205 into a correspondingly shaped groove 255 formed in the edge of the main wall member. The AAV assembly is made of LSR which allows it to be compressed into the slot formed in the elbow. The resiliency of the AAV assembly returns it to its original shape whereby it will flex into locking relationship with the slot. The outer surface 260 of the main wall member is substantially flush with the outer surface 265 of the elbow, as seen in FIGS. 53-55.

2.5 Fifth Embodiment

Figure 58:
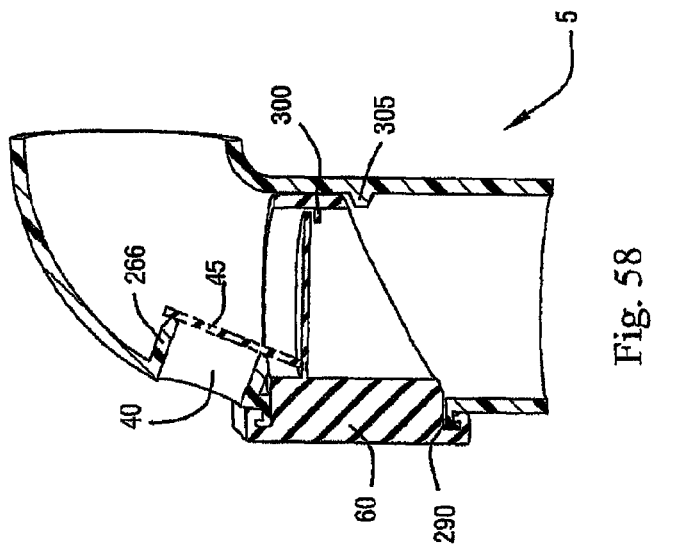
FIG. 58 is cross-sectional view thereof.
Figure 57:
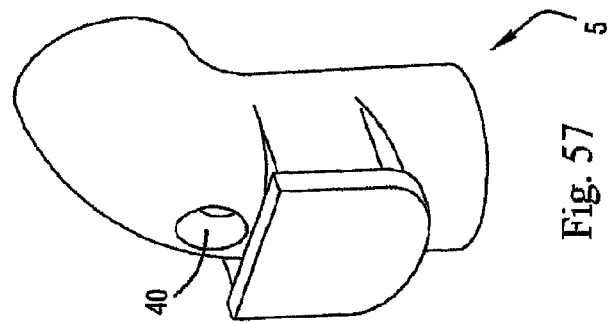
FIG. 57 is a perspective view thereof in an assembled condition.
Figure 56:
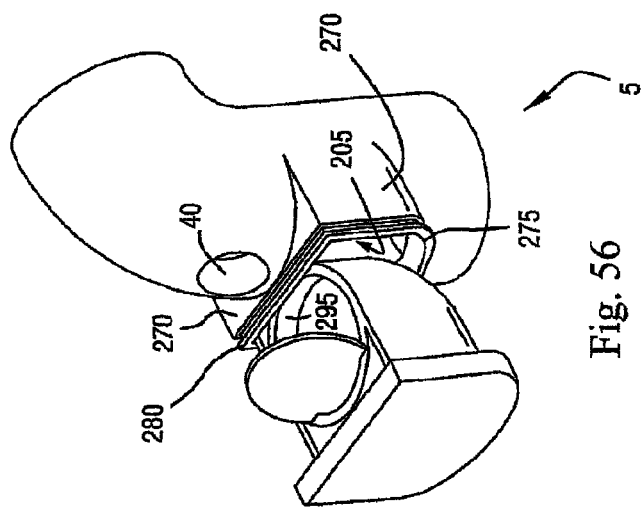
FIG. 56 is an exploded perspective view of an elbow assembly according to yet another embodiment of the present invention.

FIGS. 56-58 show an elbow assembly 5 according to another embodiment of the present invention. The elbow assembly 5 includes an elbow and an AAV assembly. The elbow includes a port 40 that includes a cylindrical conduit 266 leading to the interior of the elbow. The conduit forms an end portion intended to form a generally flat engagement portion with flap portion 45, when activated. The elbow includes molded extension members 270, just below the port, that form an attachment interface 275 for engagement with the AAV assembly. The attachment interface 275 includes a flanged portion 280 that extends about the periphery of the slot. The flanged portion engages with a groove 290 formed in the main wall member 60.

The AAV assembly is generally wedge shaped and slides in drawer-like fashion into the slot 205 of the elbow. The surrounding portion 295 of the AAV assembly is generally hoop shaped and may include an internal ledge 300 to support the flap portion in the rest position. The inside surface of the elbow may include a shoulder 305 or ledge to support the lower portion of the hoop shaped portion.

2.6 Sixth Embodiment

FIGS. 59-61 show a portion of an elbow assembly 5 according to another embodiment of the present invention. This embodiment is similar to the prior embodiment, but the cylindrical portion 310 of the elbow does not include extension members that present a generally flat attachment portion for the AAV assembly 15. Instead, the main wall member has a curved profile so that it can be locked with the flanged portion 315 formed on the cylindrical portion 310 of the elbow. The main wall member 60 can be preformed in a curved manner, or it can simply bend upon engagement with the elbow.

2.7 Seventh Embodiment

FIGS. 62-67 illustrate three alternative embodiments of an AAV assembly 15 and clip member 200 for insertion into the slot of an elbow. In each of the embodiments, the AAV assembly 15 and clip member 200 may be independent parts, permanently joined (e.g., glued, overmolded), or semi-permanently joined (e.g., mechanical interlock). Also, the shape of the AAV assembly 15 and clip member 200 may be modified in other suitable manners. In addition, some combination of features of the three alternative embodiments may be used.

Figure 62:
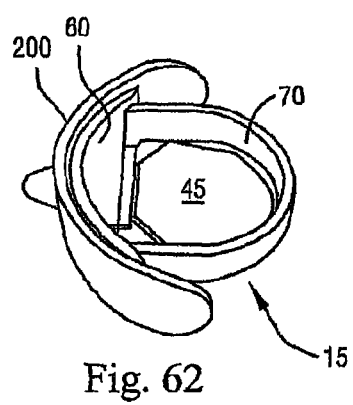
FIGS. 62-67 illustrate alternative embodiments of an AAV assembly and clip member.
Figure 63:
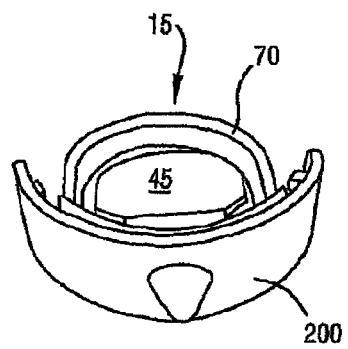

FIGS. 62 and 63 illustrate an embodiment that provides a clip member 200 that is relatively rigid. This arrangement provides additional protection of the AAV assembly 15 and limits incorrect assembly modes. Also, the relatively rigid support provides a more robust appearance.

Figure 65:
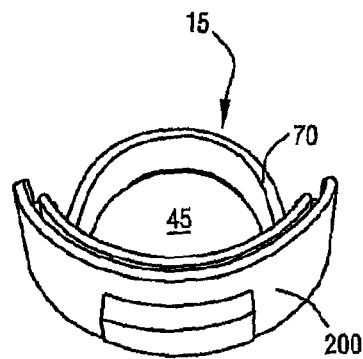
Figure 64:
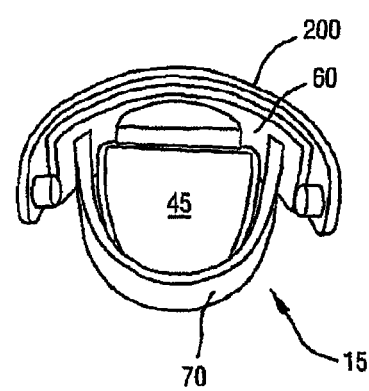

FIGS. 64 and 65 illustrate an embodiment that provides a clip member 200 with a relatively flexible base member 70. This arrangement is relatively easier to assemble into clip than the rigid support, and is relatively larger to provide a perception of robustness. In addition, there is less chance of damaging the hinge supporting the flat portion 45 (compared to the rigid support).

Figure 66:
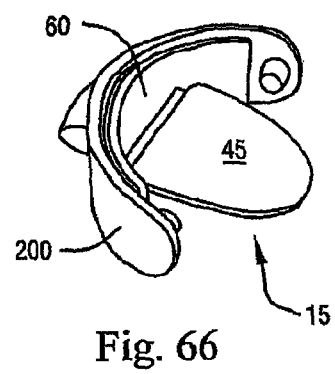
Figure 67:
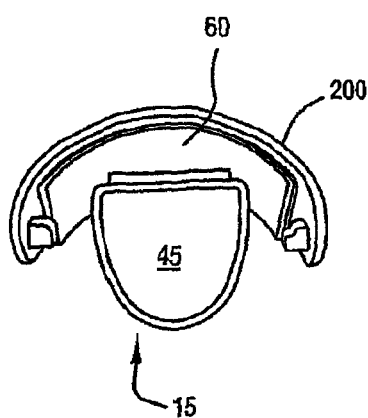

FIGS. 66 and 67 illustrate an embodiment that provides an AAV assembly 15 with an open flap portion 45. This arrangement is relatively easier to assemble than rigid and flexible supports, and limits incorrect assembly modes. Also, this arrangement allows a more streamlined elbow design.

2.8 Eighth Embodiment

FIGS. 68-89 illustrate an elbow assembly 5 according to another embodiment of the present invention. As illustrated, the elbow assembly 5 includes an elbow 10, an AAV assembly 15, and a clip member 200 to secure the AAV assembly 15 to the elbow 10.

The elbow 10 includes a first portion 404 provided to the mask frame and a second portion 406 provided to a swivel joint connected to an air delivery tube. The first portion 404 includes snap-fit tabs 408, e.g., six tabs, to connect the first portion 404 to the mask frame with a snap-fit. However, more or less snap-fit tabs may be used, e.g., 2-10 tabs. A unique mold/tool configuration may be used to produce the snap-fit tabs 408 which are less prone to molding stress build-up and therefore less likely to break off the elbow. Localized stress during the molding process may be reduced by the incorporation of radii on internal edges. Two of the snap-fit tabs 408, e.g., upper and lower tabs, are more elongated and extend into the mask frame when connected. These elongated tabs 408 may be squeezed to release the elbow 10 from the mask frame.

The second portion 406 includes snap-fit tabs 410, e.g., six tabs, to connect the second portion 406 to the swivel joint. A unique mold/tool configuration may be used to produce the snap-fit tabs 410 which are less prone to molding stress build-up and therefore less likely to break off the elbow. Localized stress during the molding process may be reduced by the incorporation of radii on internal edges. The snap-fit diameter at the second portion 406 is smaller than the snap-fit diameter at the first portion 404 to prevent incorrect assembly. Also, the retention force of the snap-fit at the second portion 406 is smaller than the retention force of the snap-fit at the first portion 404. This arrangement provides a quick-release safety and convenience feature.

Annular rings 412, e.g., three rings, are provided on the second portion 406 for improved seal with the swivel joint and improved manufacturability.

The elbow 10 also includes a slot 414 to receive the AAV assembly 15, a port 416 that is selectively closed by the flap portion 45 of the AAV assembly 15, and two recesses 418 for attaching the clip member 200 with a snap-fit. The slot 414 has a thin bead around its opening which forms a line contact sealing region to prevent air leak.

The AAV assembly 15 interlocks with the clip member 200 to provide a sub-assembly that is removably attached to the elbow 10 with a snap-fit. Specifically, the AAV assembly 15, e.g., constructed of flexible silicone, includes a protrusion 420 that removably interlocks with a slot 422 provided on the clip member 200, e.g., constructed of rigid plastic. The clip member 200 includes two tabs 424 that interlock with respective recesses 418 provided to the elbow 10.

Figure 68:
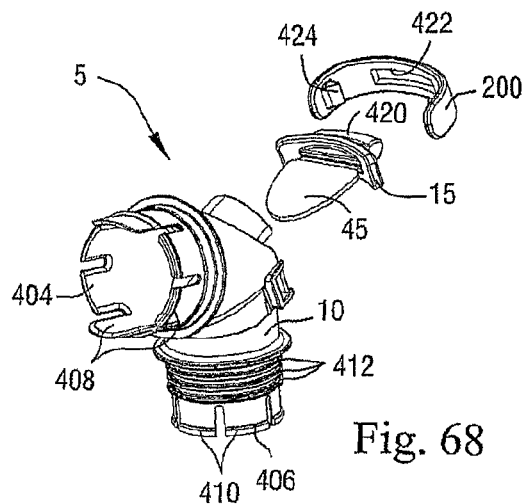
FIGS. 68-89 show various views of an elbow assembly according to another embodiment of the present invention.
Figure 69:
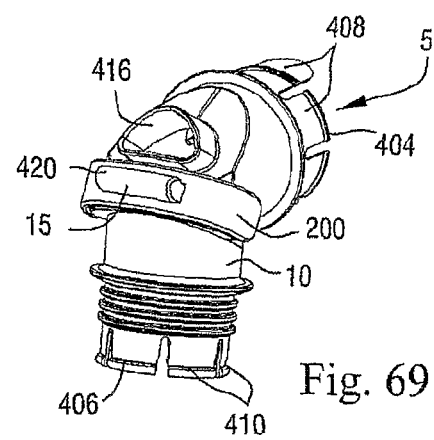
Figure 70:
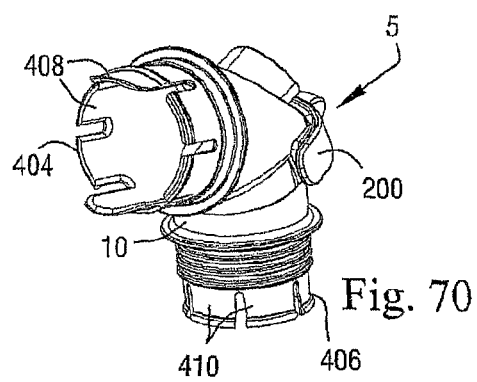
Figure 71:
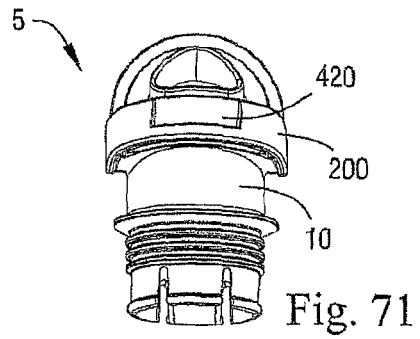
Figure 72:
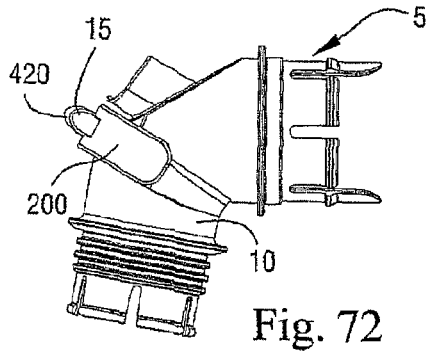
Figure 73:
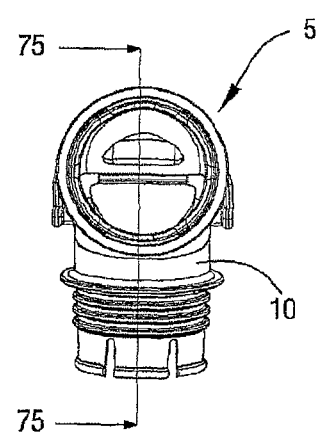
Figure 74:
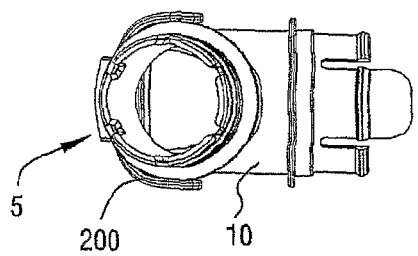
Figure 75:
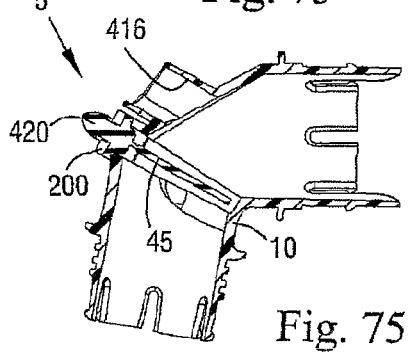
Figure 76:
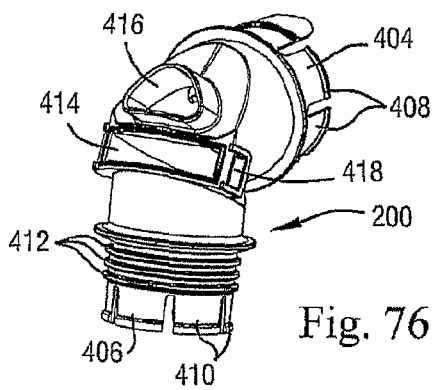
Figure 77:
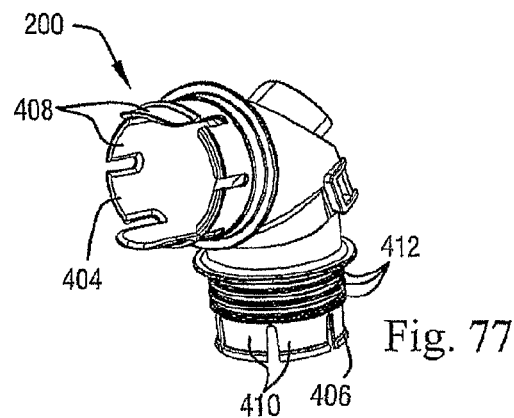
Figure 78:
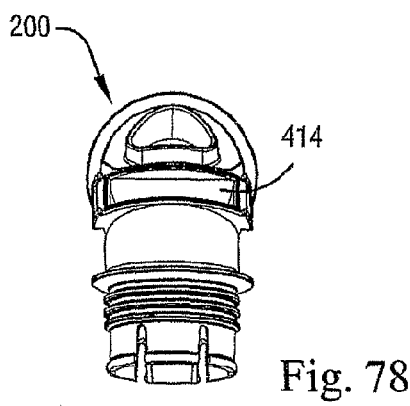
Figure 79:
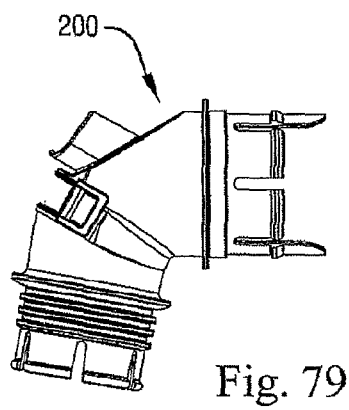
Figure 80:
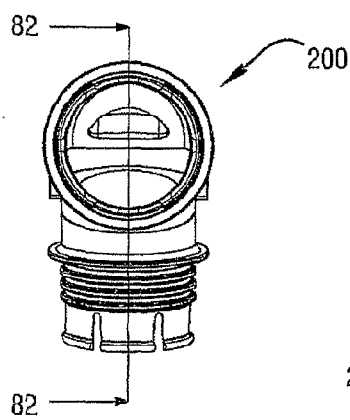
Figure 81:
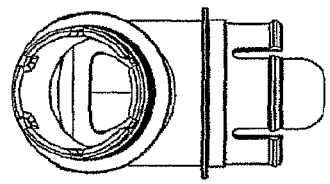
Figure 82:
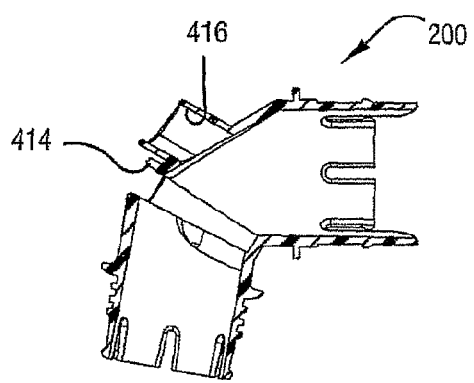
Figure 83:
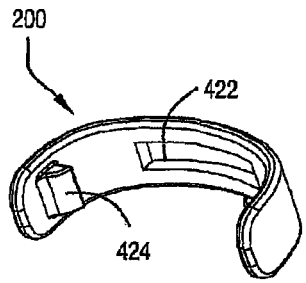
Figure 84:
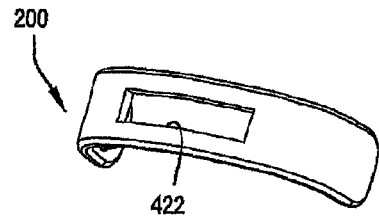
Figure 85:
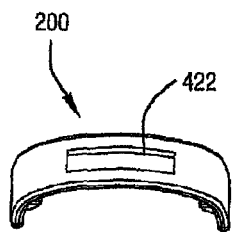
Figure 86:
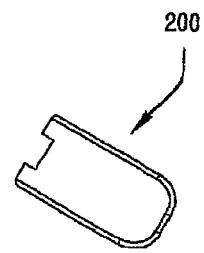
Figure 87:
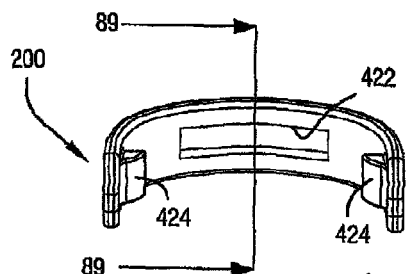
Figure 88:
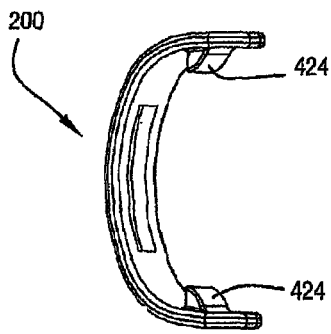
Figure 89:
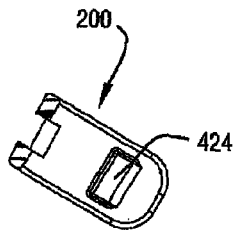

FIG. 68 is an exploded view of the elbow assembly 5, FIGS. 69-75 are assembled views of the elbow assembly 5, FIGS. 76-82 are isolated views of the elbow 10, and FIGS. 83-89 are isolated views of the clip member 200.

2.9 Ninth Embodiment

FIGS. 90-111 illustrate an elbow assembly 5 according to another embodiment of the present invention. As illustrated, the elbow assembly 5 includes an elbow 10, an AAV assembly 15, and a clip member 200 to secure the AAV assembly 15 to the elbow 10.

This embodiment is similar to the elbow assembly 5 shown in FIGS. 68-89. In contrast, the elbow assembly 5 of FIGS. 90-111 includes two rigid tabs 430 integrally molded with the elbow 10 to prevent over-extension of the elongated snap-fit tabs 408 during disassembly and thereby prevent their breakage. Also, the clip member 200 has a shroud-like configuration with a hole 43' that aligns with the port 416.

Figure 90:
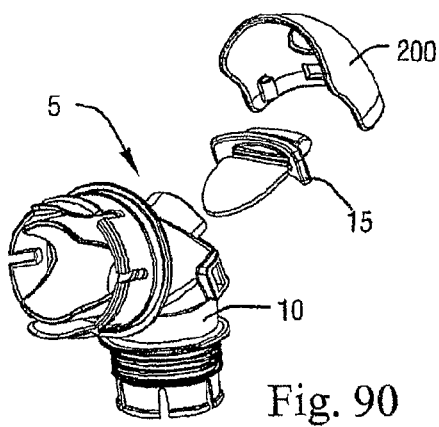
Figure 91:
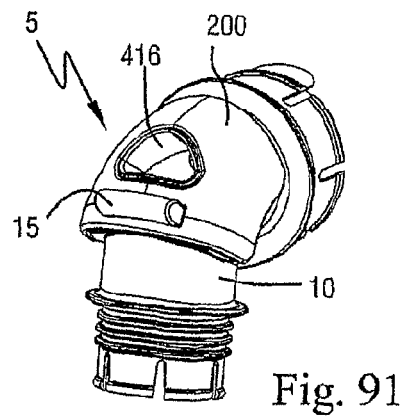
Figure 92:
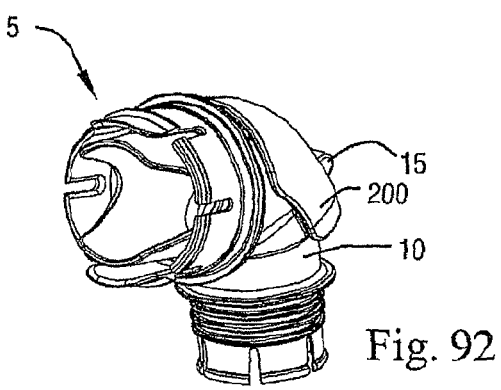
Figure 93:
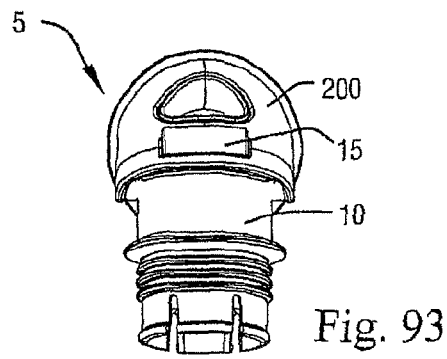
Figure 94:
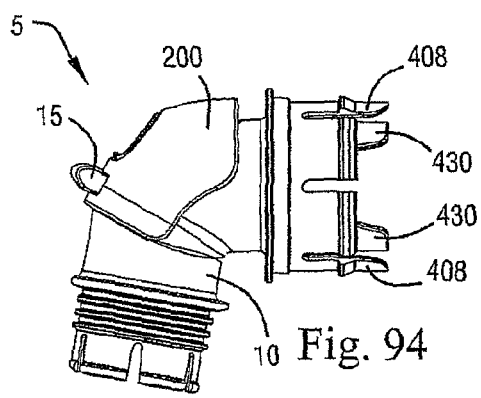
Figure 95:
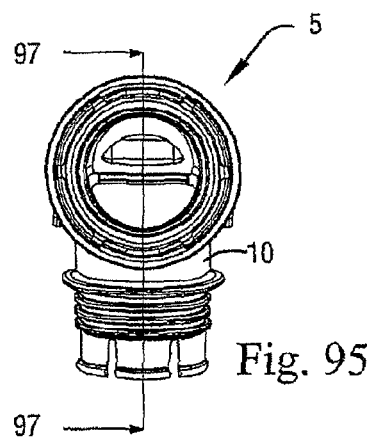
Figure 96:
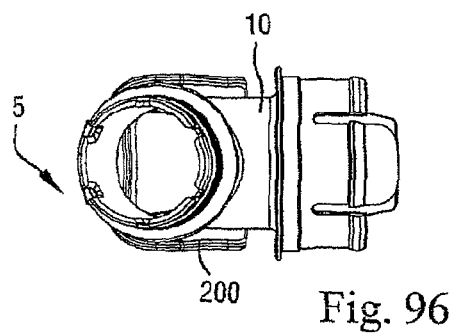
Figure 97:
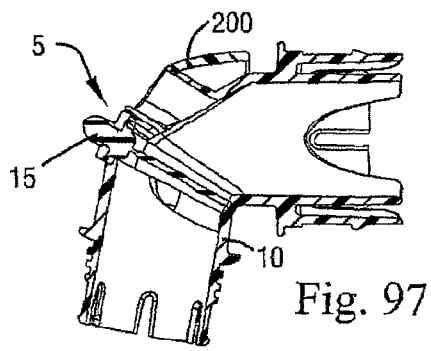
Figure 98:
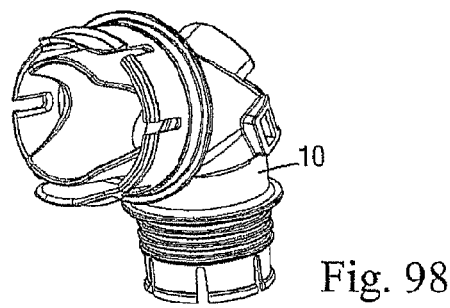
Figure 99:
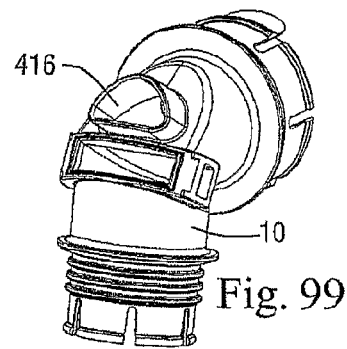
Figure 100:
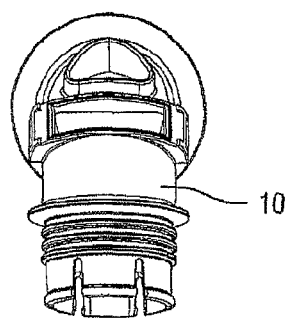
Figure 101:
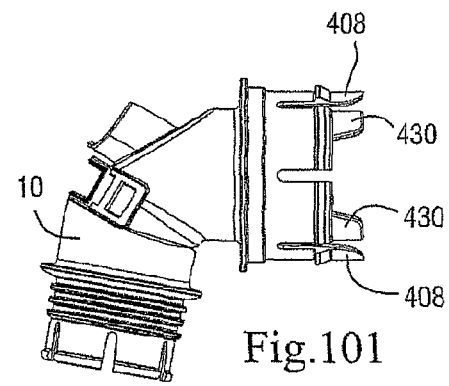
Figure 103:
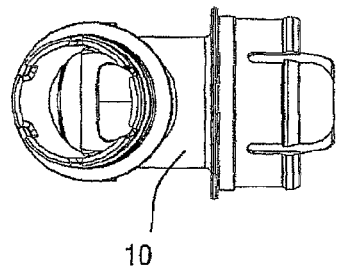
Figure 102:
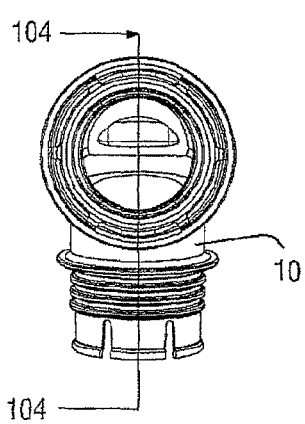
Figure 104:
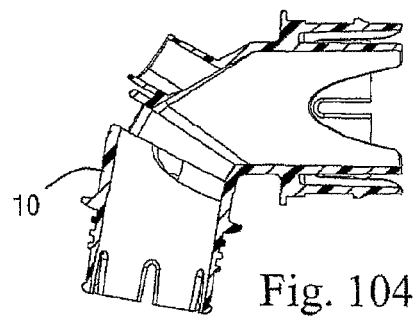

FIG. 90 is an exploded view of the elbow assembly 5, FIGS. 91-97 are assembled views of the elbow assembly 5, FIGS. 98-104 are isolated views of the elbow 10, and FIGS. 105-111 are isolated views of the clip member 200.

2.10 Tenth Embodiment

FIGS. 112-133 illustrate an elbow assembly 5 according to another embodiment of the present invention. As illustrated, the elbow assembly 5 includes an elbow 10, an AAV assembly 15, and a clip member 200 to secure the AAV assembly 15 to the elbow 10.

This embodiment is similar to the elbow assembly 5 shown in FIGS. 90-111. Annular rings 413 and 412 are provided on first and second end portions 404, 406, respectively, for an improved seal with the frame and swivel joint, respectively, and improved manufacturability. In contrast, the clip member 200 of FIGS. 112-133 includes a more elongated shroud-like configuration. Also, the first portion 404 does not include elongated tabs 408 aligned with rigid tabs 430. In addition, the elbow of FIGS. 112-133 includes protrusions 415 rather than a recess which interact with protrusions on the clip member 200. The elongated shroud-like configuration of the clip member 200 provides a visual indicator to aid correct assembly of the clip member to the elbow 10.

Figure 112:
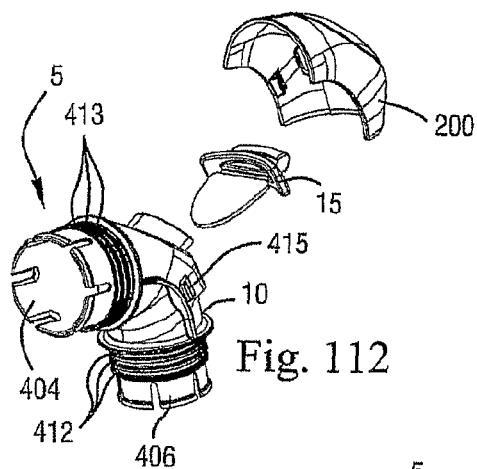
FIGS. 112-133 show various views of an elbow assembly according to another embodiment of the present invention.
Figure 113:
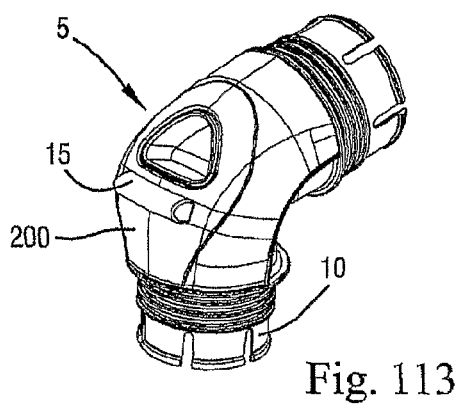
Figure 114:
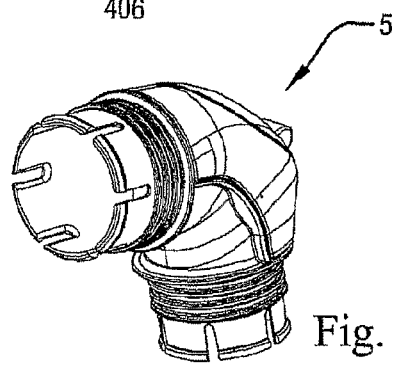
Figure 115:
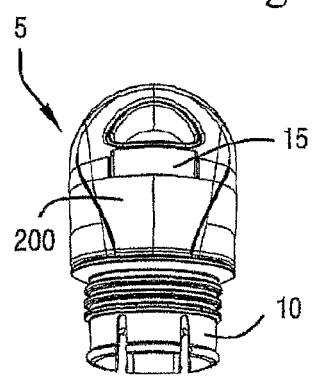
Figure 116:
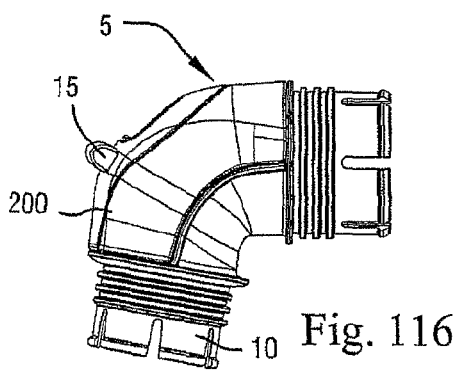
Figure 117:
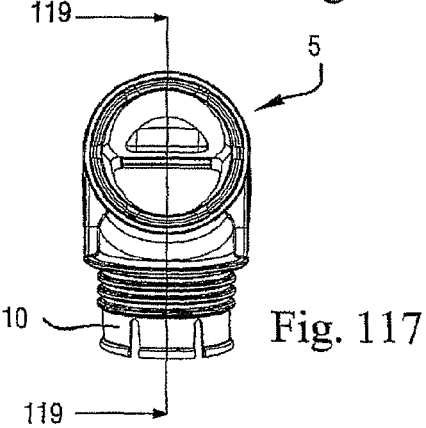
Figure 118:
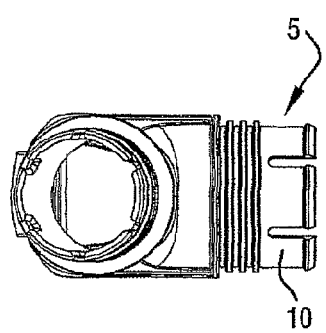
Figure 119:
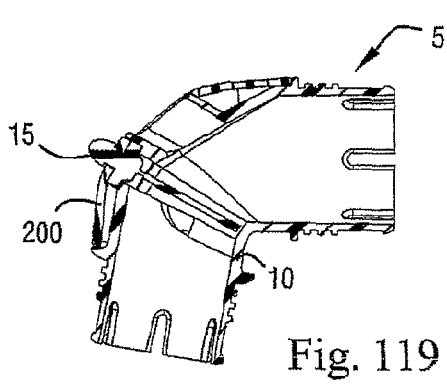
Figure 120:
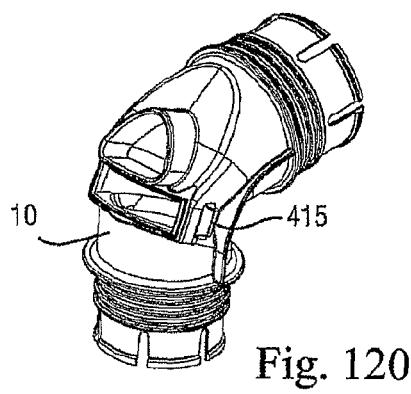
Figure 121:
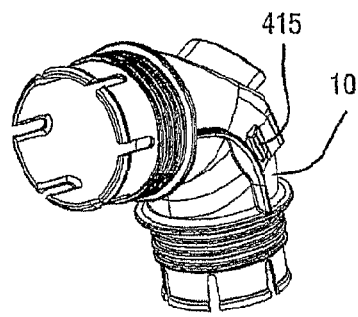
Figure 122:
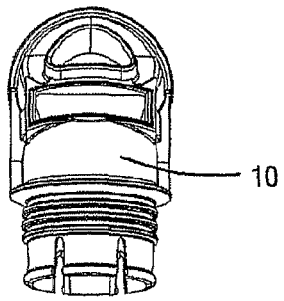
Figure 123:
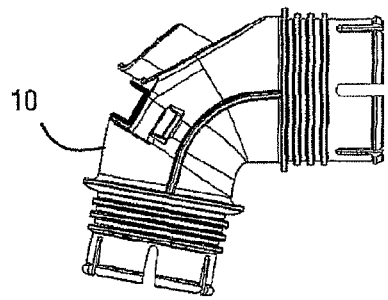
Figure 124:
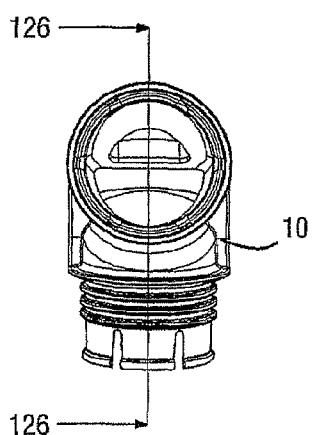
Figure 125:
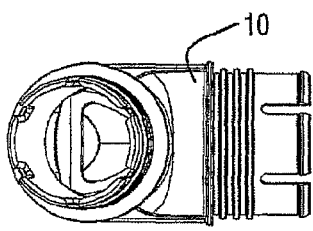
Figure 126:
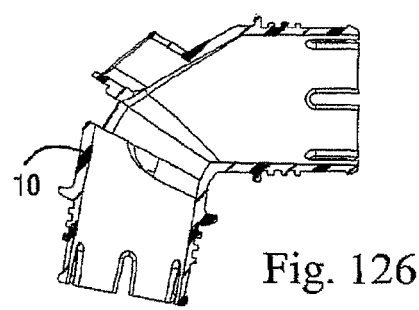
Figure 127:
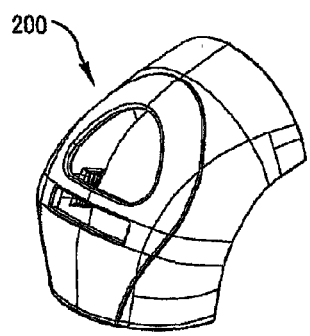
Figure 128:
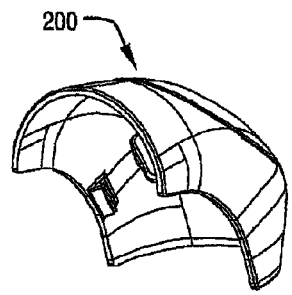
Figure 129:
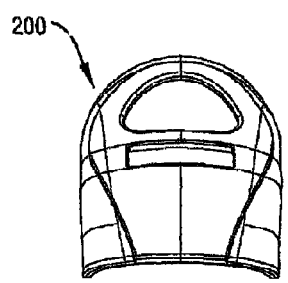
Figure 130:
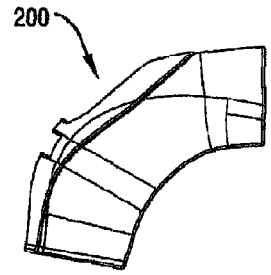
Figure 131:
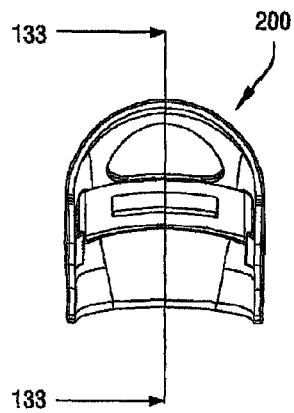
Figure 132:
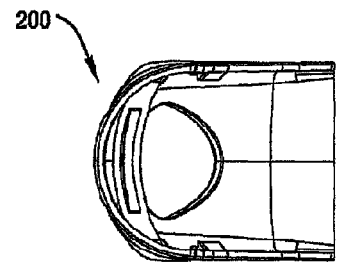
Figure 133:
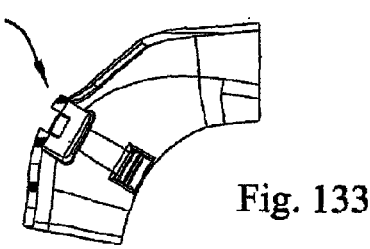

FIG. 112 is an exploded view of the elbow assembly 5, FIGS. 113-119 are assembled views of the elbow assembly 5, FIGS. 120-126 are isolated views of the elbow 10, and FIGS. 127-133 are isolated views of the clip member 200. The clip member 200 is relatively large and is easier for patients with low dexterity to manipulate. Further, if dropped, it is easier to locate, particularly in the dark.

2.11 Eleventh Embodiment

FIGS. 134-154 illustrate an elbow assembly 5 according to another embodiment of the present invention. As illustrated, the elbow assembly 5 includes an elbow 10, an AAV assembly 15, and a clip member 200 to secure the AAV assembly 15 to the elbow 10.

This embodiment is similar to the elbow assembly 5 shown in FIGS. 68-89. In contrast, the elbow assembly 5 of FIGS. 134-154 is structured such that the clip member 200 is substantially flush with a surface 435 surrounding the port 416. Also, the first portion 404 does not include elongated tabs 408. The port 416 also has a central rib 436 to prevent small objects from falling in or being placed in the port 416 and thereby affecting AAV function.

Figure 134:
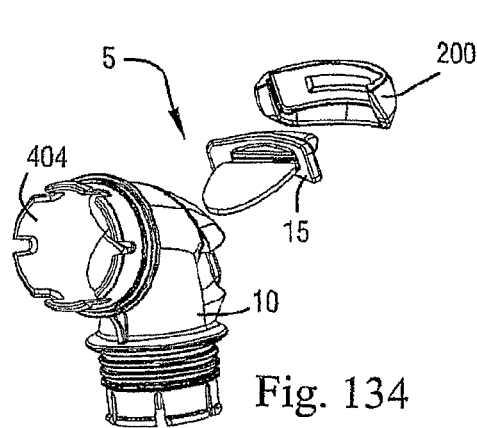
FIGS. 134-154 show various views of an elbow assembly according to another embodiment of the present invention.
Figure 135:
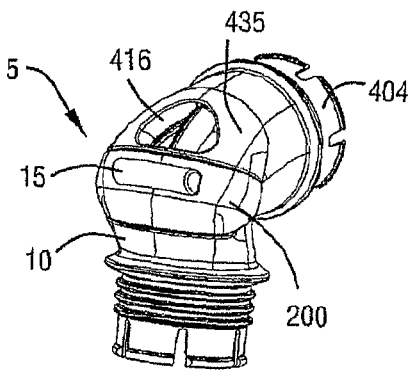
Figure 136:
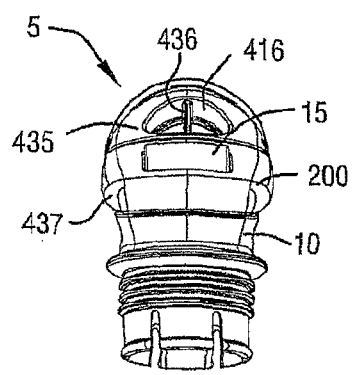
Figure 137:
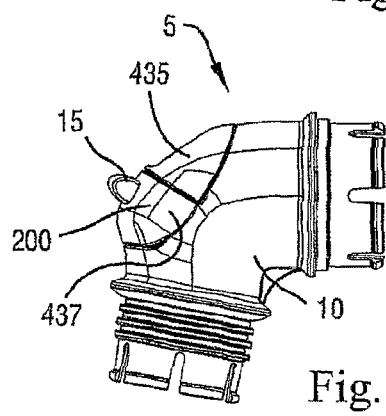
Figure 138:
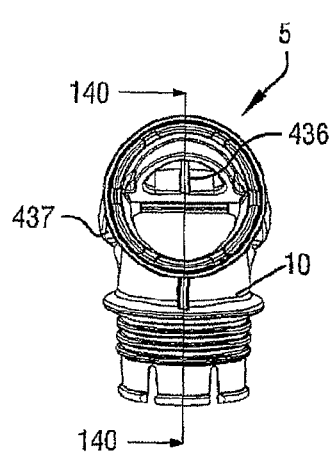
Figure 139:
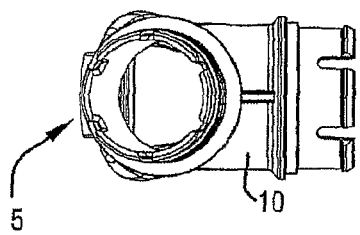
Figure 140:
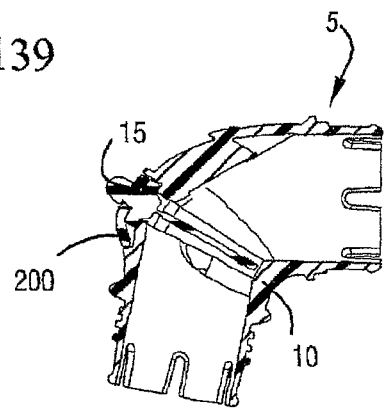
Figure 141:
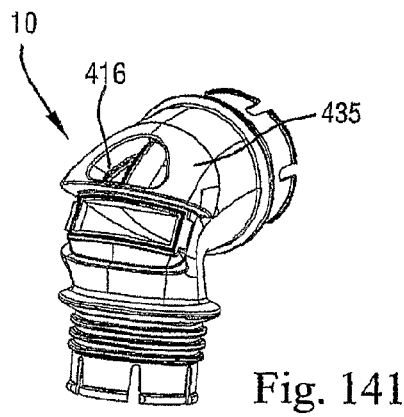
Figure 142:
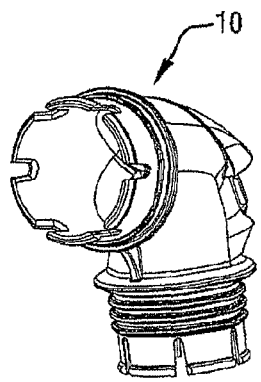
Figure 143:
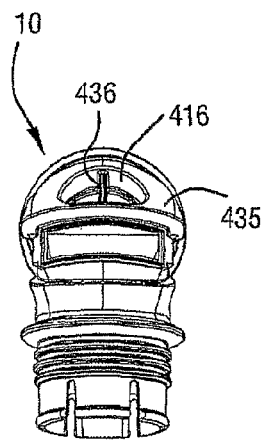
Figure 144:
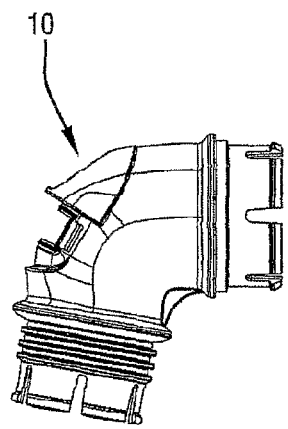
Figure 145:
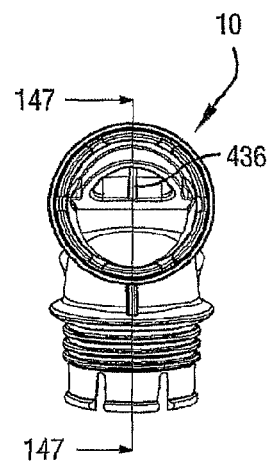
Figure 146:
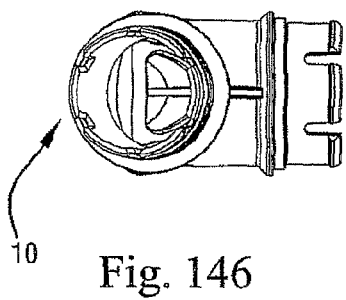
Figure 147:
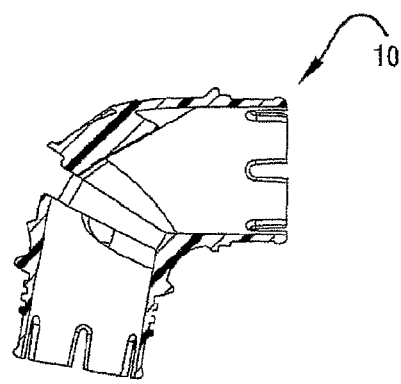
Figure 148:
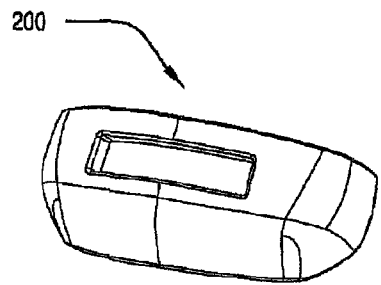
Figure 149:
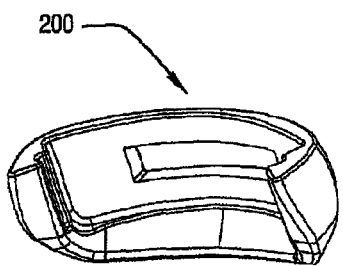
Figure 150:
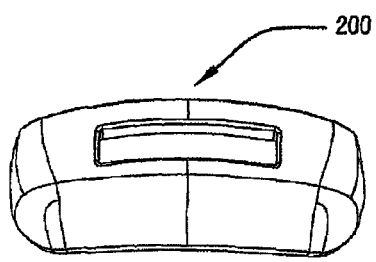
Figure 151:
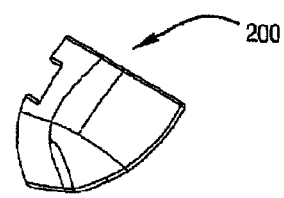
Figure 152:
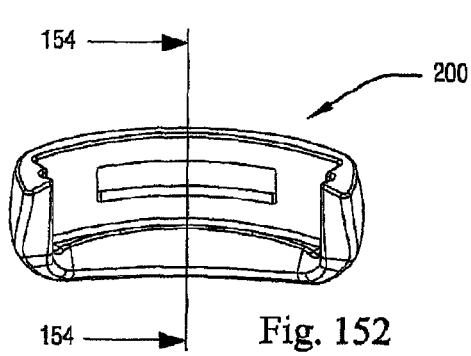
Figure 153:
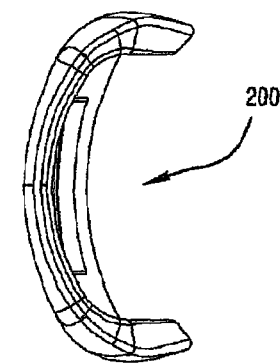
Figure 154:
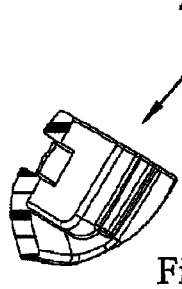

FIG. 134 is an exploded view of the elbow assembly 5, FIGS. 135-140 are assembled views of the elbow assembly 5, FIGS. 141-147 are isolated views of the elbow 10, and FIGS. 148-154 are isolated views of the clip member 200.

Figure 155:
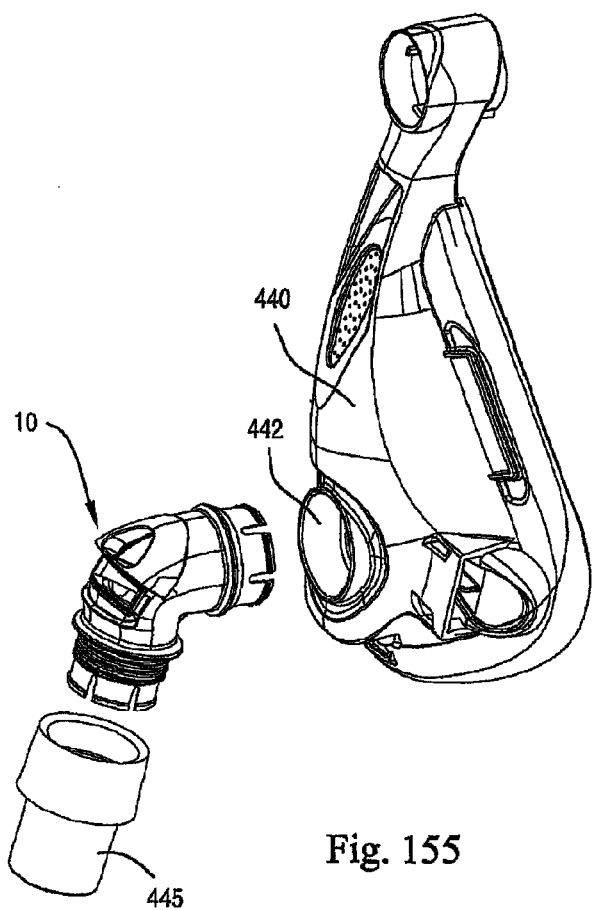
FIGS. 155-156 are exploded views illustrating the elbow of FIGS. 134-154 being assembled between a mask frame and a swivel joint.
Figure 156:
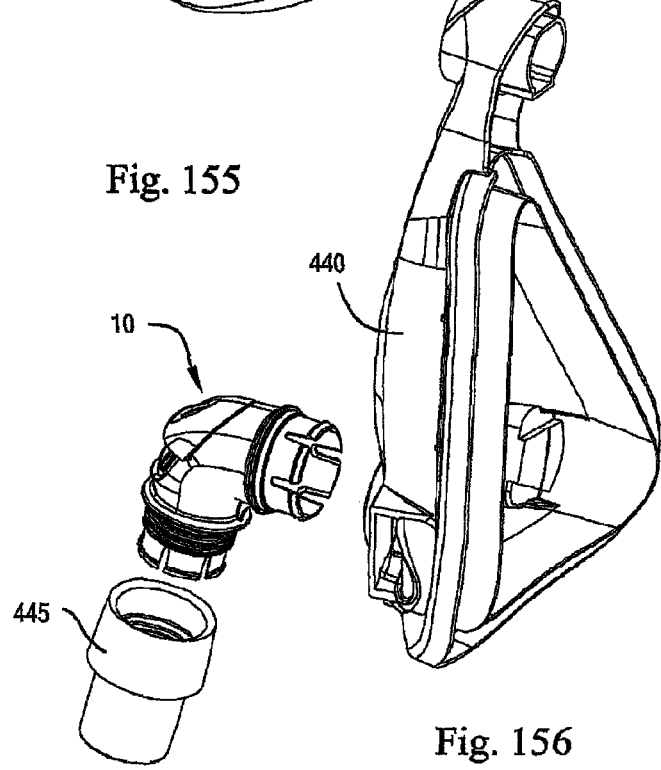
Figures 157, 158:
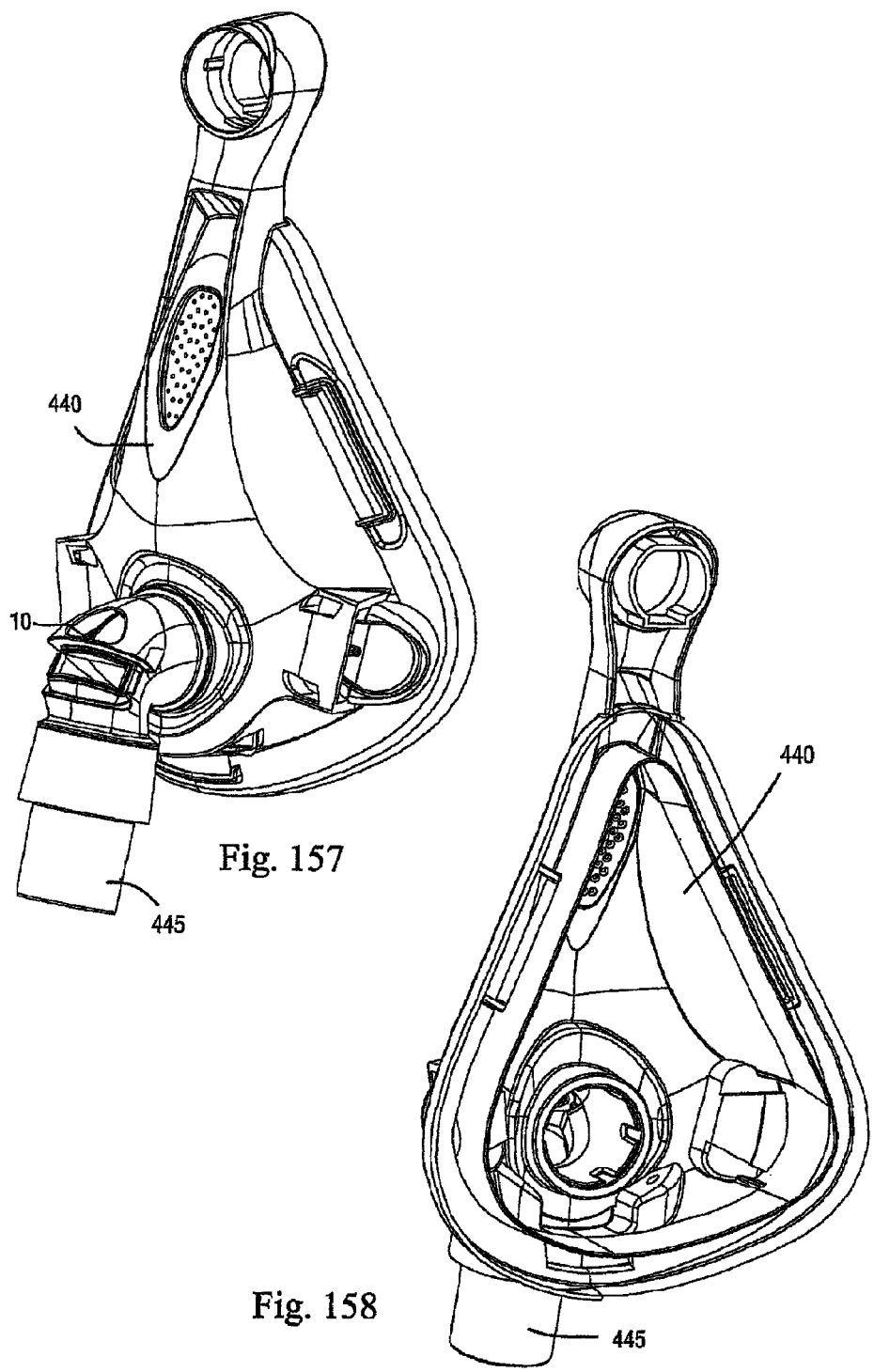
FIGS. 157-161 show various views of the elbow of FIGS. 134-154 connected between the mask frame and the swivel joint of FIGS. 155-156.
Figures 159, 160:
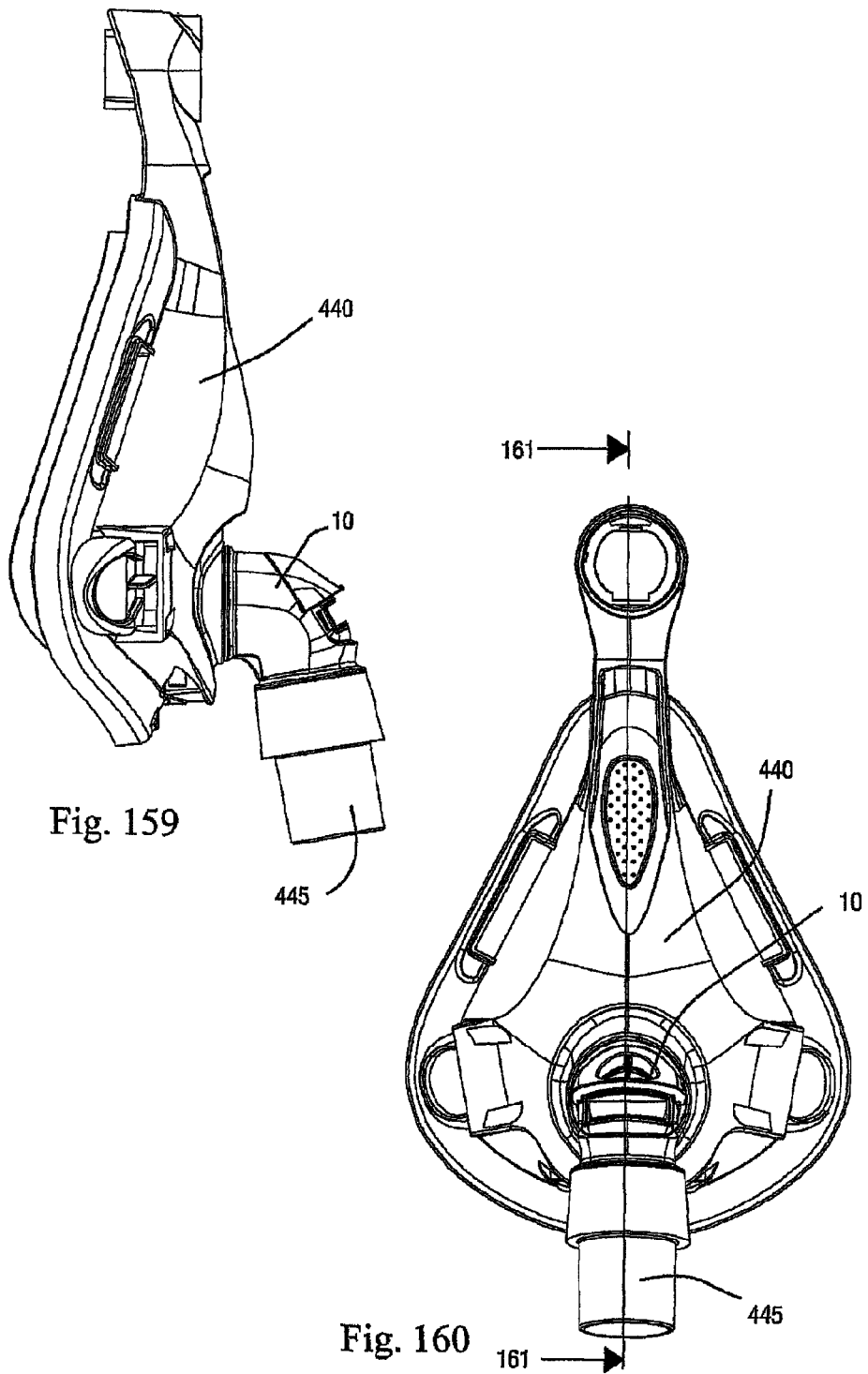
Figure 161:
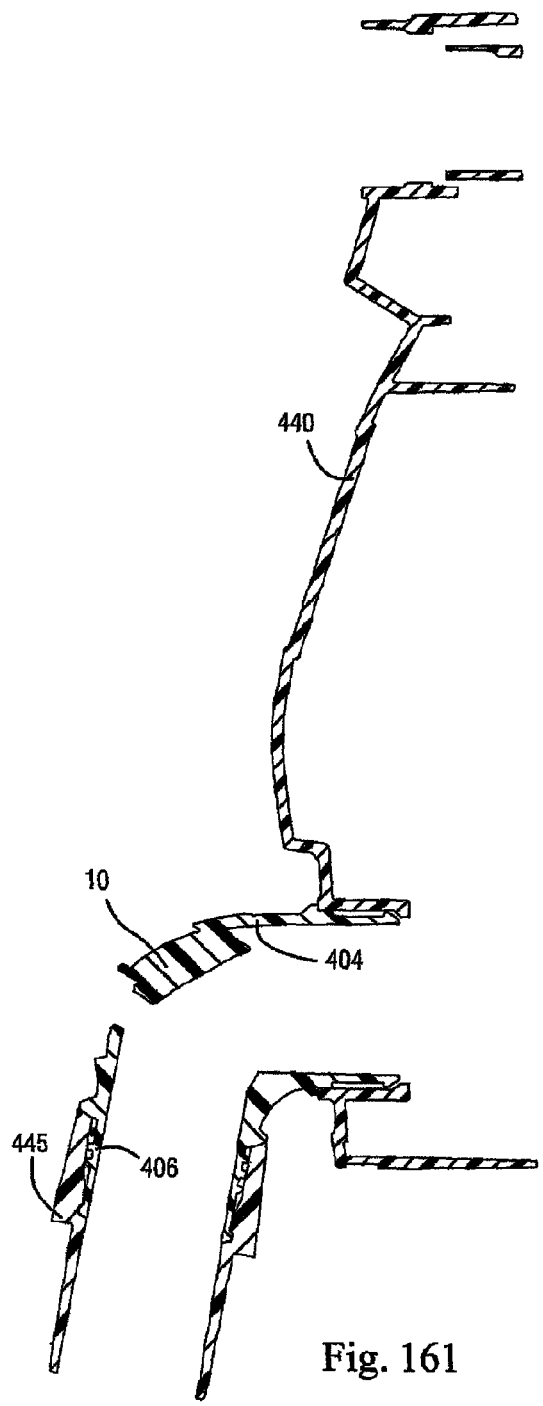

FIGS. 155-156 are exploded views illustrating the elbow 10 of FIGS. 134-154 being assembled between a mask frame 440 (via throughhole 442) and a swivel joint 445. FIGS. 157-161 are various views illustrating the elbow 10 of FIGS. 134-154 connected between the mask frame 440 and the swivel joint 445. As illustrated, the first portion 404 of the elbow 10 snap-fits to the mask frame 440, and the elbow 10 may be removed from the mask frame 440 by pulling outwards. The swivel joint 445 snap-fits to the second portion 406 of the elbow 10, and the swivel joint 445 may be removed from the elbow 10 by pulling downwards or levering off. The clip member of FIGS. 134-154 no longer has lugs to connect it to the elbow, rather the clip member has a recess. The clip member also has an overhang portion 437 to make disassembly easier, i.e., the overhang portion 437 provides an edge or finger grip/catch.

3.0 Drop-In AAV Assembly

3.1 First Embodiment

Figure 162:
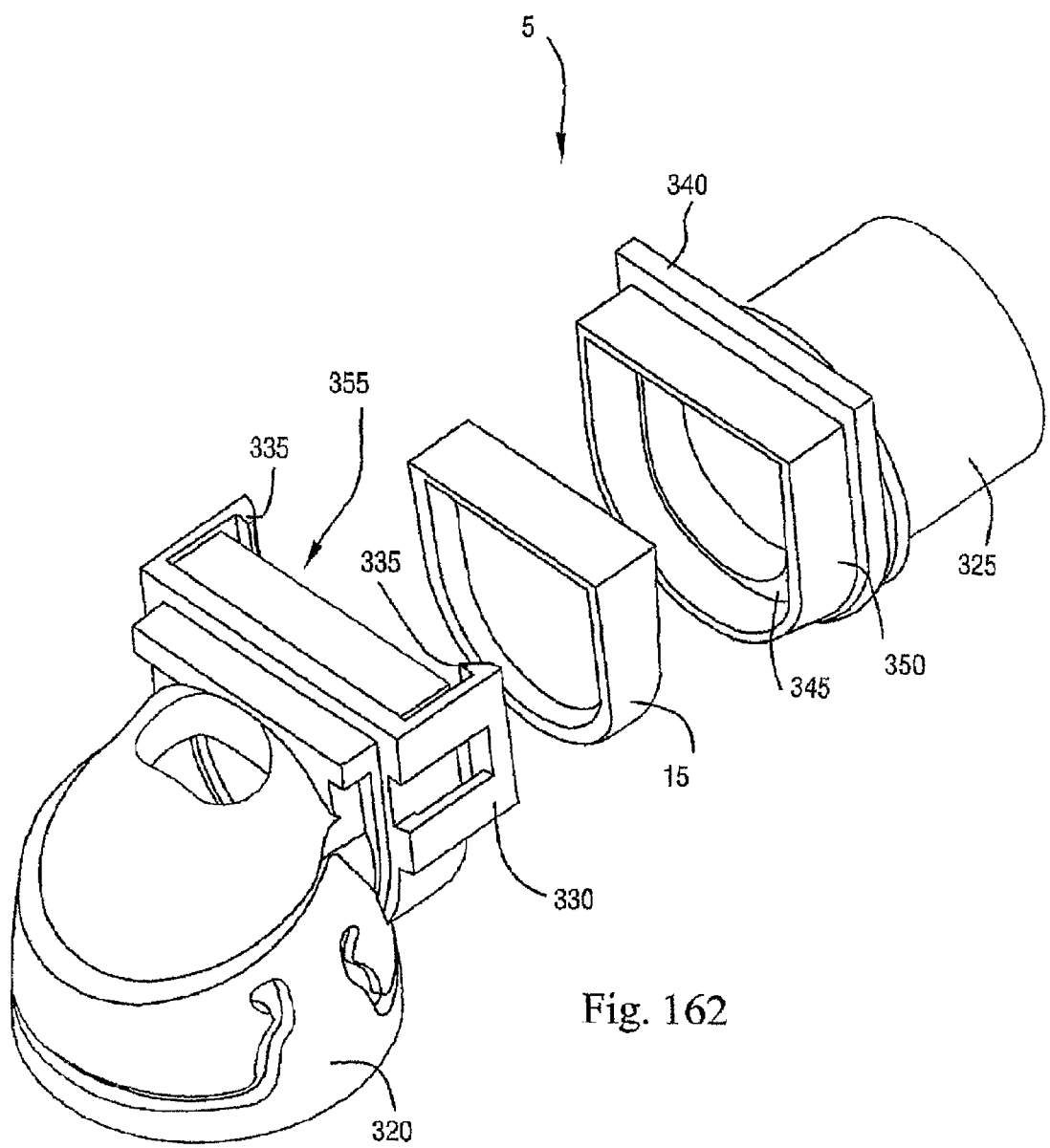
FIG. 162 is an exploded perspective view of an elbow assembly according to an embodiment of the present invention.
Figure 163:
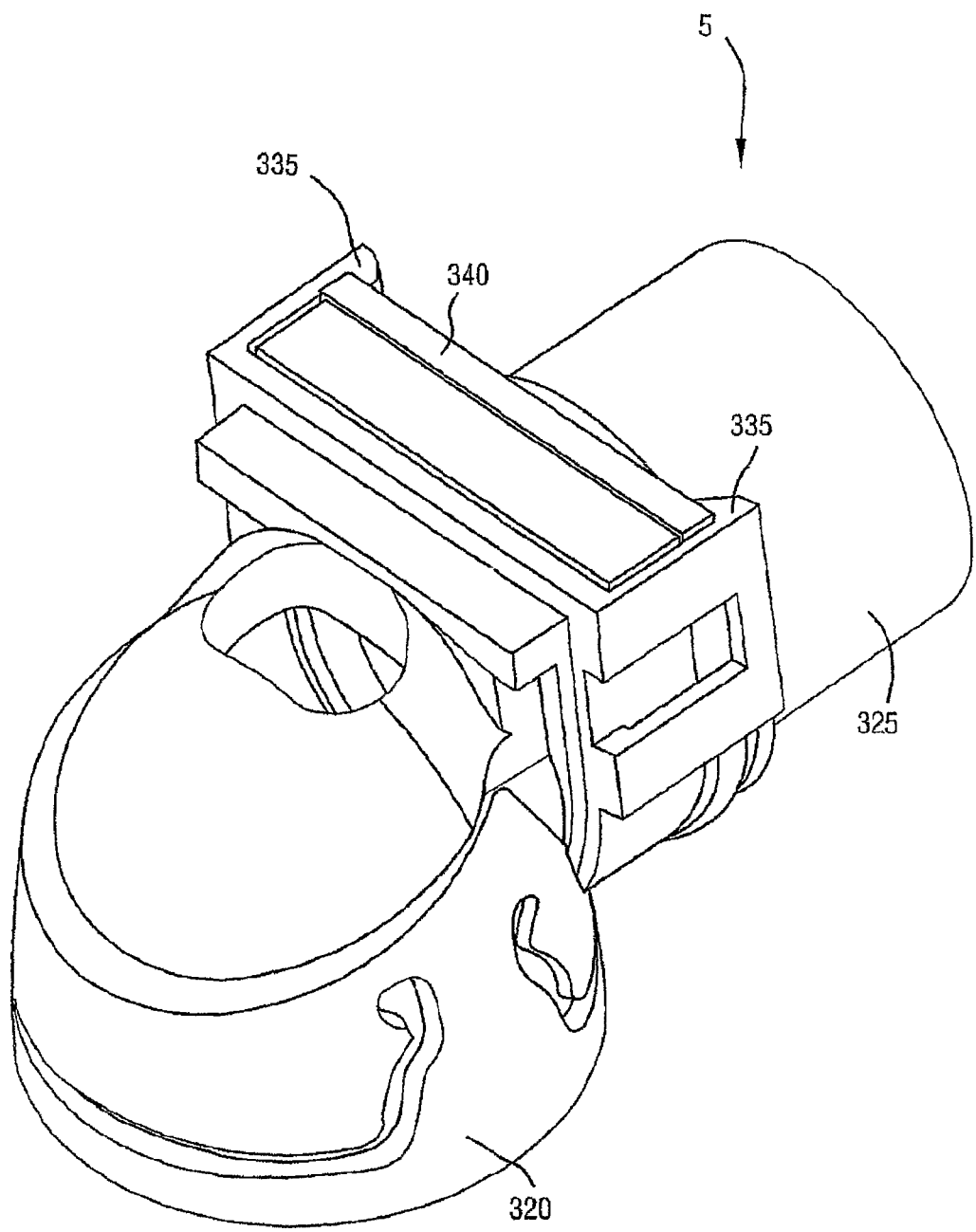
FIG. 163 is an assembled view thereof.
Figure 164:
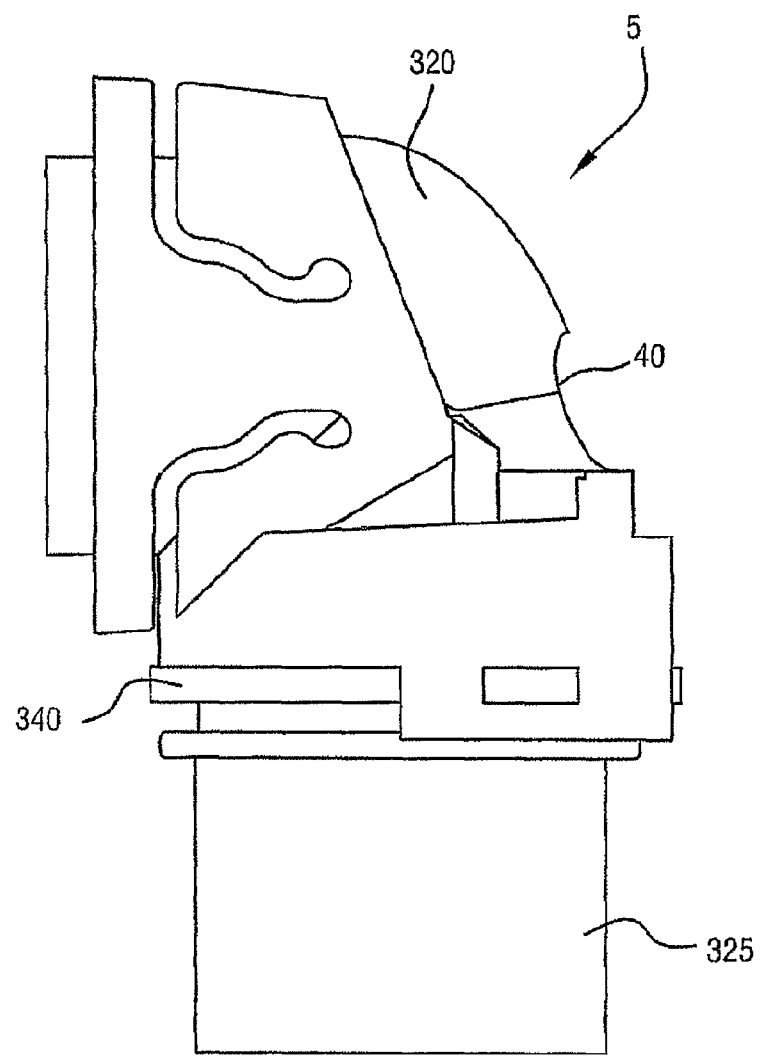
FIG. 164 is as side elevation view thereof.
Figure 165:
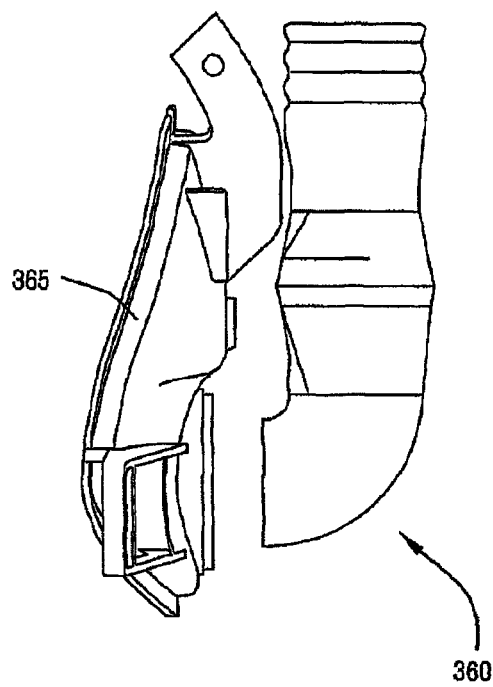
FIG. 165 is an exploded view of a mask assembly according to an embodiment of the present invention.
Figure 166:
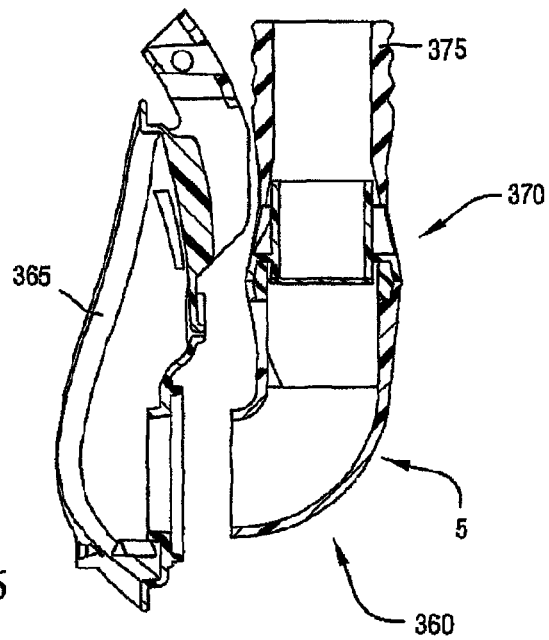
FIG. 166 is cross-sectional depiction thereof.

FIGS. 162-164 illustrate an elbow assembly 5 according to yet another embodiment of the present invention. The elbow assembly includes a first elbow portion 320, a second elbow portion 325 and an AAV assembly 15. The AAV assembly may be similar to the AAV assembly described above.

First elbow portion 320 and second elbow portion 325 are connected by a locking assembly. The locking assembly may include a one or more arms 330 having a locking claw 335 that engage with a flange 340. The position of the arms and flange may be interchanged, although FIG. 162 shows the arms/claws on the first (or upper) elbow portion, and the flange on the second (or lower) elbow portion.

The AAV assembly 15 is supported on the second elbow portion 325. The second elbow portion includes a ledge 345 to support the bottom of the AAV assembly and a wall 350 to laterally support the AAV assembly. The wall and the AAV assembly have a generally D-shaped profile to facilitate alignment. The upper elbow portion includes a D-shaped recess 355 so that the lower elbow portion can only be inserted in one orientation. While the AAV assembly is shown to have a D-shape, it need not have a wedge shape as in the prior embodiments.

3.2 Second Embodiment

FIGS. 165-168 show a mask assembly 360 according to another embodiment of the present invention. The mask assembly 360 includes a full face mask frame 365, an elbow assembly 5, and a swivel joint 370. A portion of an air delivery conduit 375 which is in communication with a flow generator is also shown.

Figure 167:
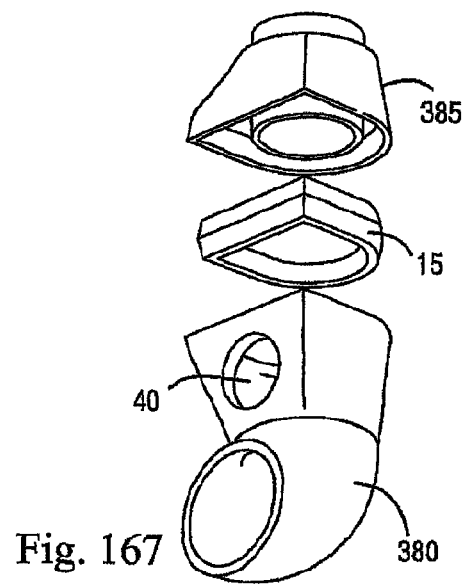
FIG. 167 is an exploded view of the elbow assembly thereof.
Figure 168:
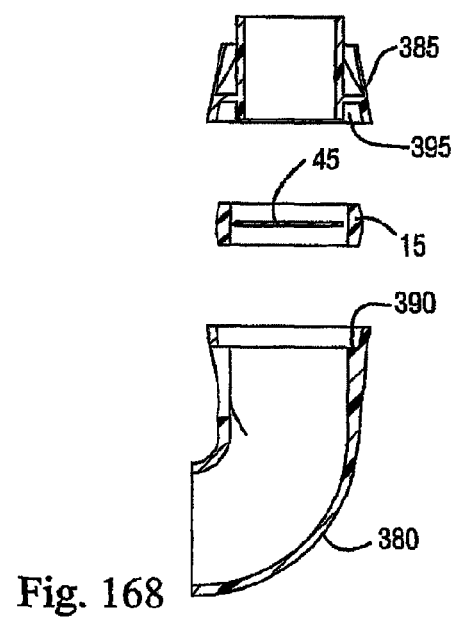
FIG. 168 is a cross-sectional view thereof.

The elbow assembly 5 as shown in FIGS. 167-168 includes a first elbow portion 380, a second elbow portion 385 and an AAV assembly 15 positioned therebetween. The first elbow portion 380 includes a shoulder 390 to support the AAV assembly, while the second elbow portion includes a channel 395 to receive the AAV assembly. The AAV assembly and the interfacing portions of the first and second elbow portions have a unique shape that allows for the correct orientation of the hinge portion of the flap portion relative to the port in the elbow. In one example, these portions are generally D-shaped. The D-shape of the AAV assembly allows it to be assembled in one of two correct positions (right side up or upside down), as described above. The side walls of the AAV assembly may be generally curved as well, as shown in FIG. 168.

As seen in FIG. 167, the first elbow portion 380 includes a port 40 that can be selectively opened when the flap portion of the AAV assembly has been closed. The port 40 in this example is oriented towards the mask frame, or on the inside curve of the elbow. The AAV assembly is oriented to accommodate for the changed location of the port as well.

3.3 Third Embodiment

Figure 169:
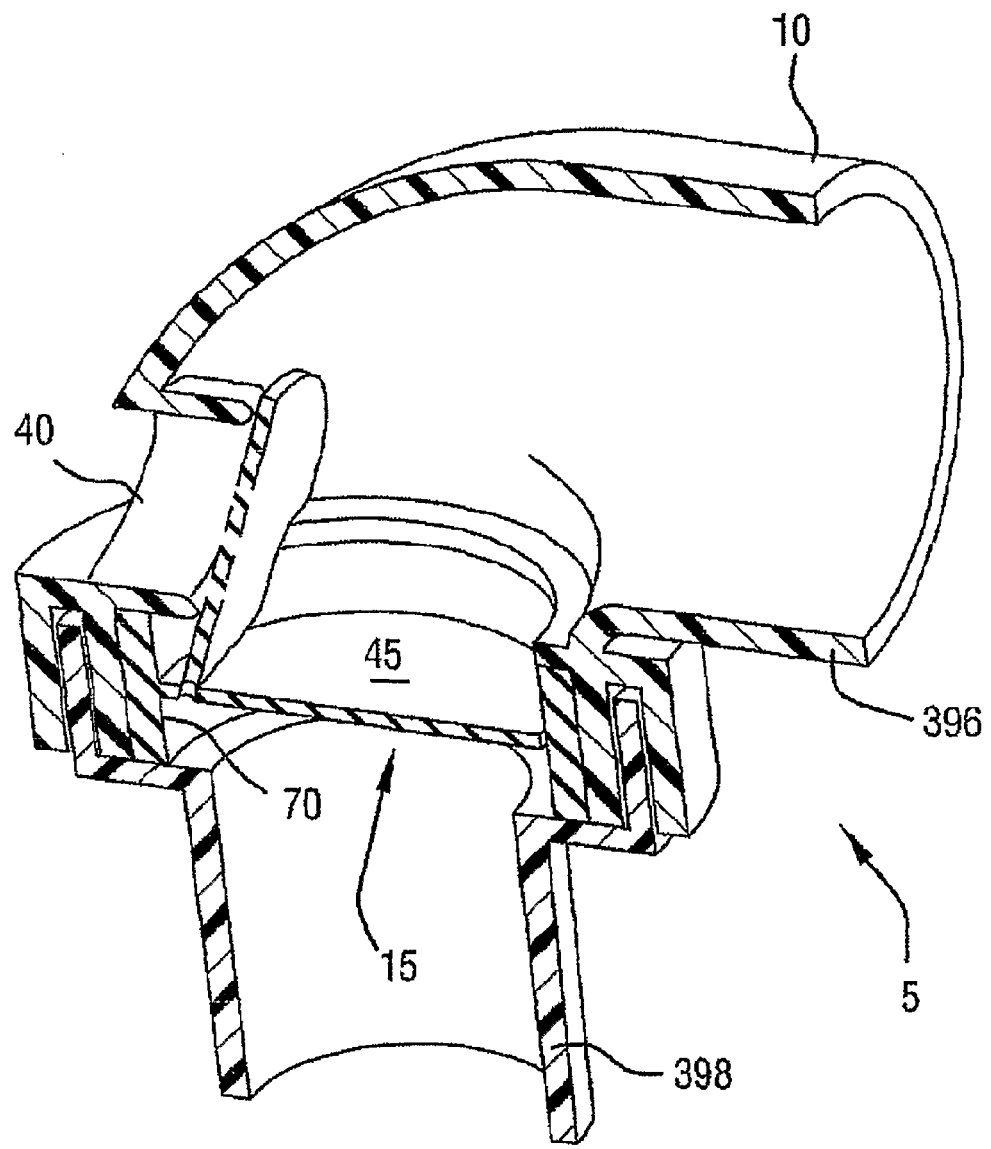
FIG. 169 is a cross-sectional view of an elbow assembly according to an embodiment of the present invention.
Figure 170:
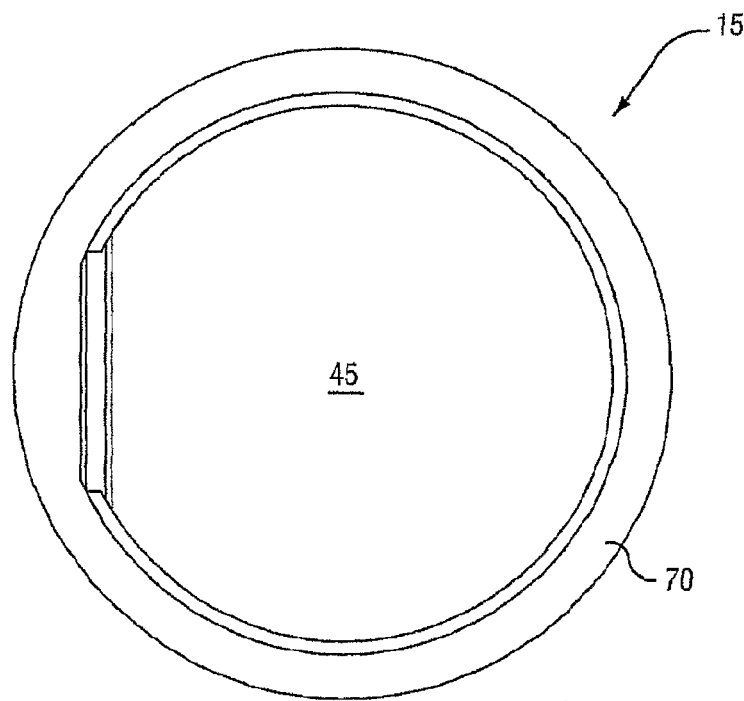
FIG. 170 is a top view of an AAV assembly for use in the assembly of FIG. 169.
Figure 171:
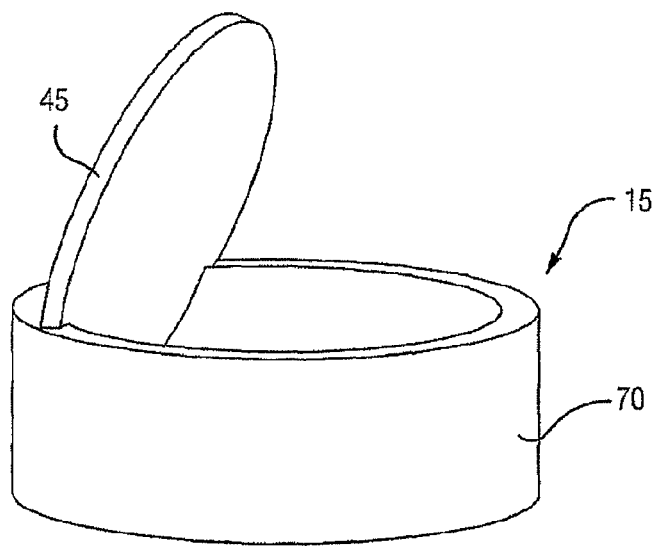
FIG. 171 is a perspective view thereof with the AAV assembly with the flap portion in an upright position.

FIGS. 169-171 illustrate an elbow assembly 5 according to yet another embodiment of the present invention. Elbow assembly 5 includes a first elbow portion 396, a second elbow portion 398 and an AAV assembly 15 sandwiched between the first and second portions of the elbow. The AAV assembly in this example has a generally cylindrical base member 70 and a flap portion 45 hinged to an inside surface of the base member.

The first elbow portion 396 includes a port 40 that can be engaged by the flap portion 45 of the AAV assembly. The first and second portions of the elbow are connected via a tongue and groove arrangement.

3.4 Fourth Embodiment

Figure 172:
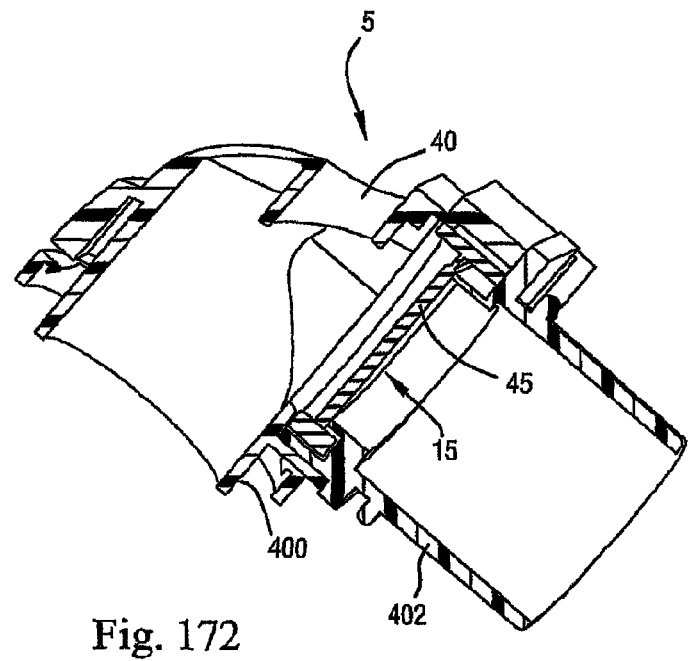
FIGS. 172-173 illustrate an elbow assembly with a drop-in AAV assembly according to another embodiment of the present invention.
Figure 173:
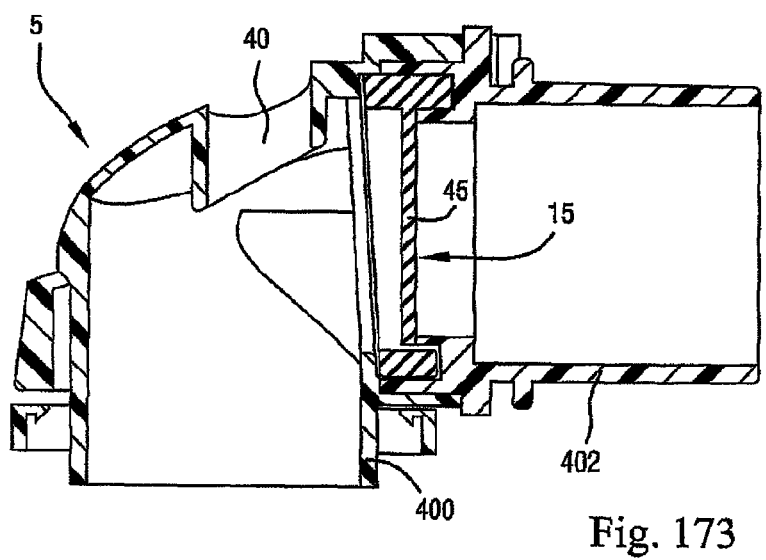
Figure 186:
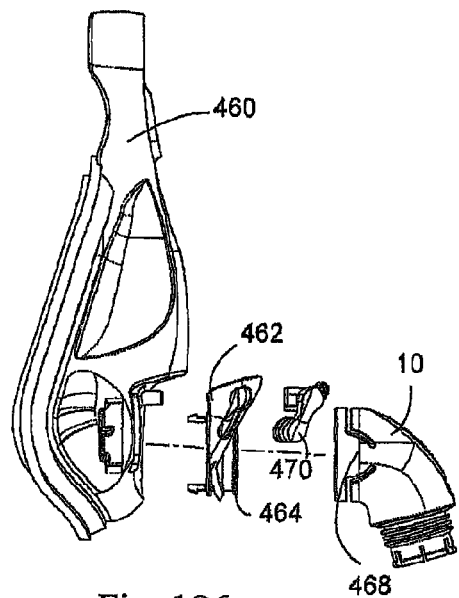
Figure 187:
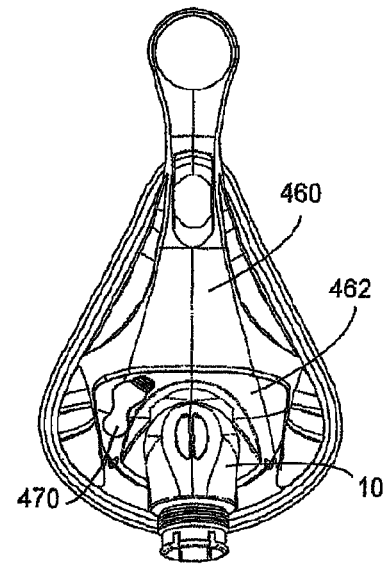
Figure 188:
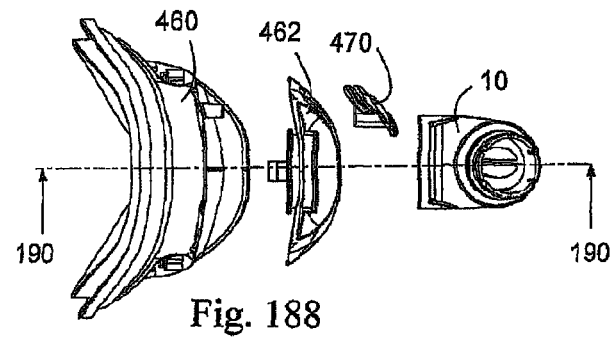
Figure 189:
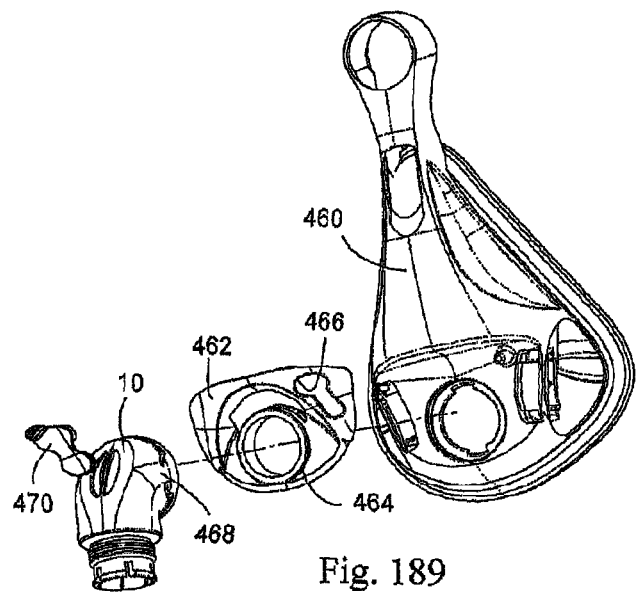
Figure 190:
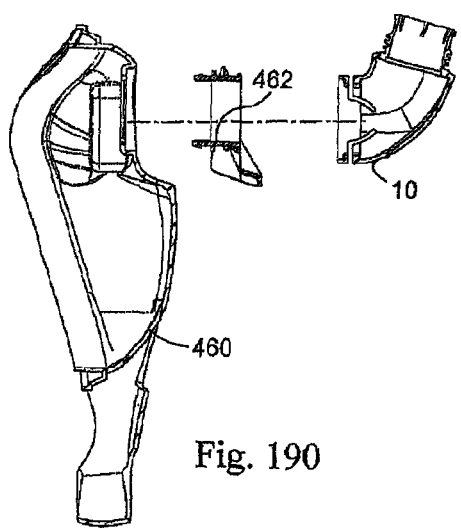
Figure 191:
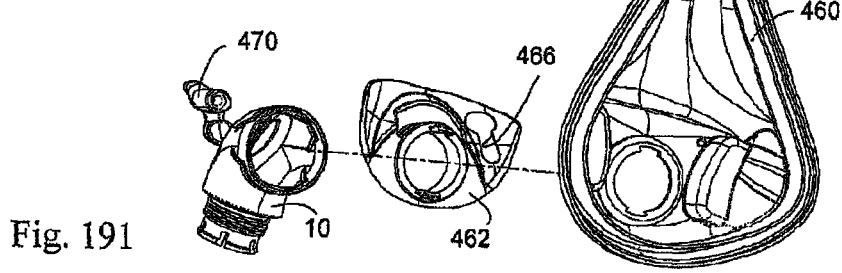
Figure 192:
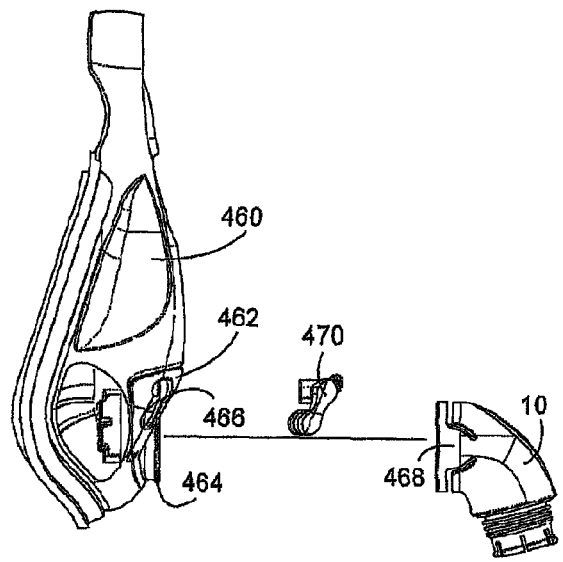
Figure 193:
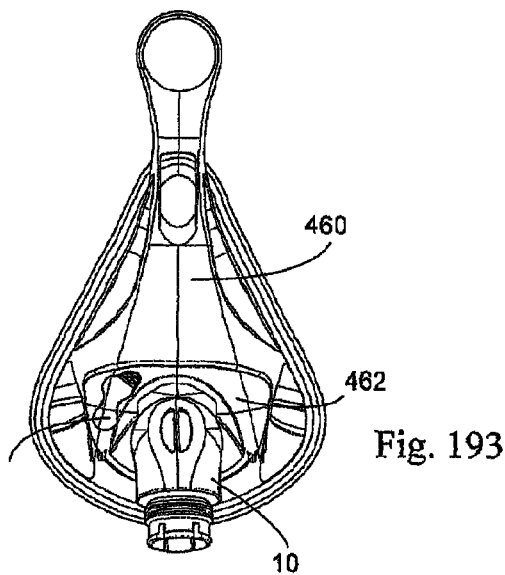
Figure 194:
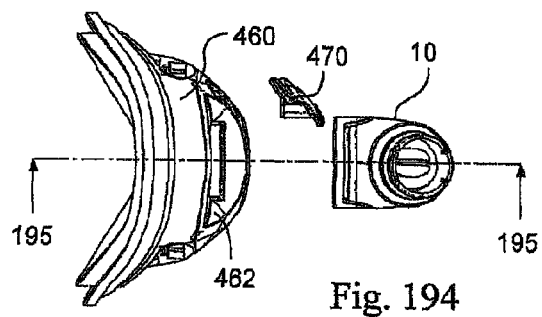
Figure 195:
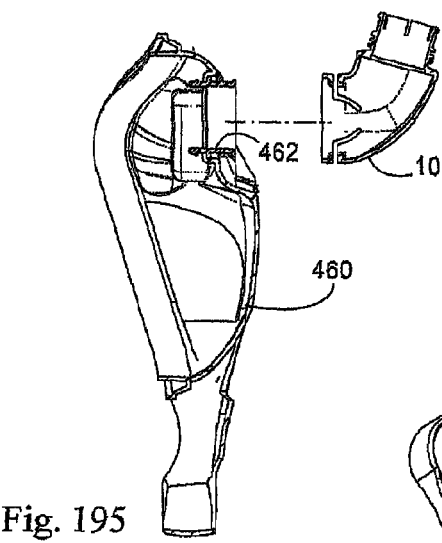
Figure 196:
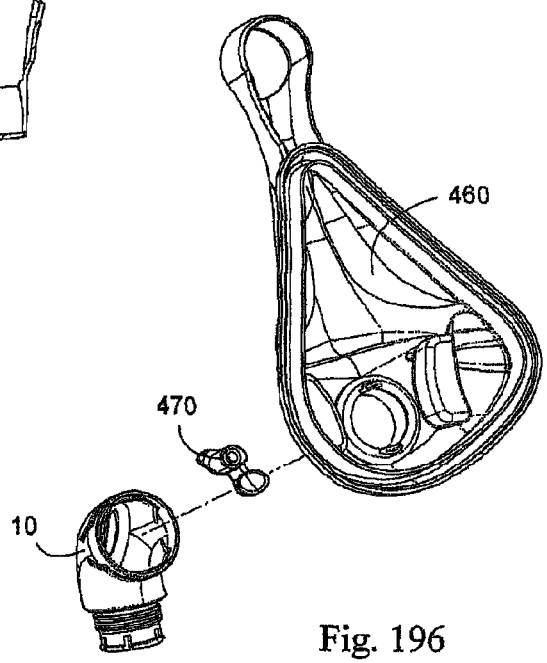
Figure 197:
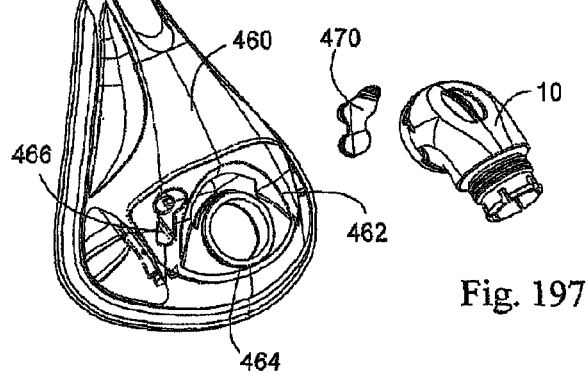
Figure 198:
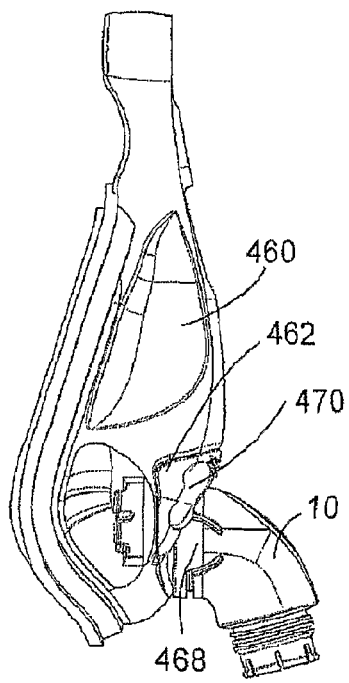
Figure 199:
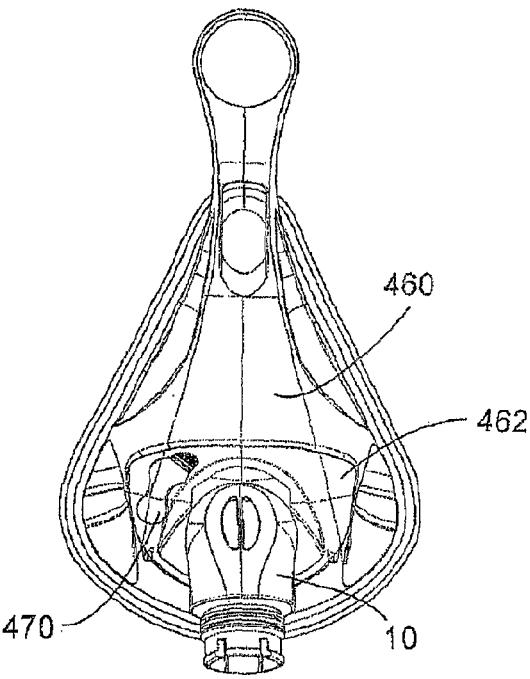
Figure 200:
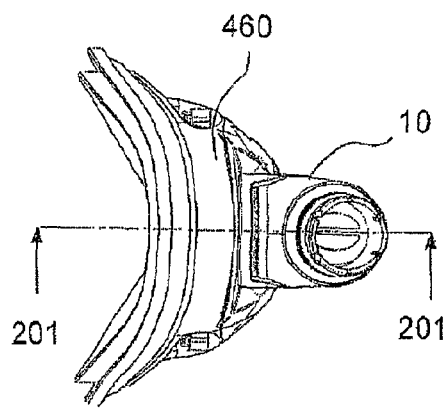
Figure 204:
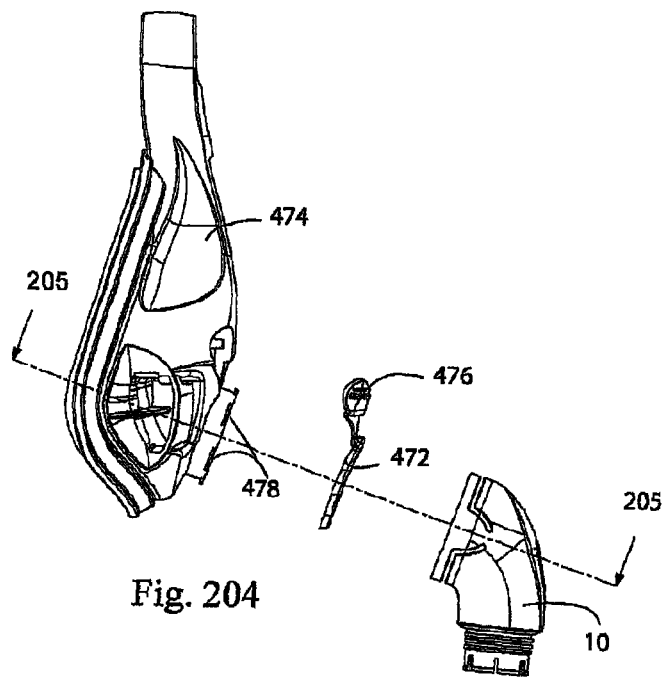
Figure 205:
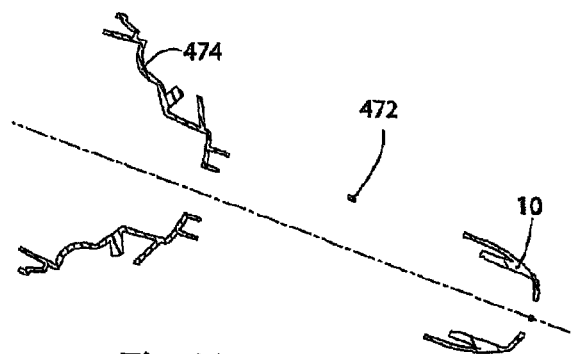
Figure 206:
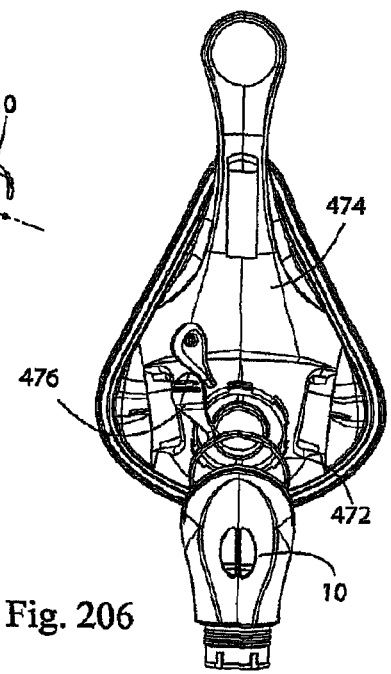
Figure 207:
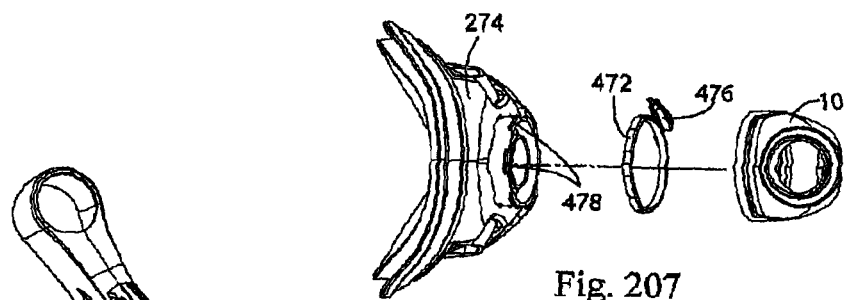
Figure 208:
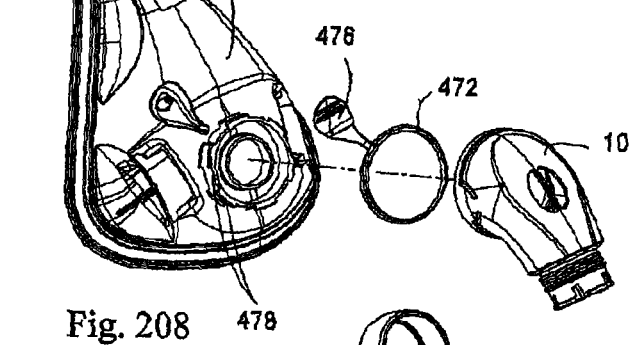

FIGS. 172 and 173 illustrate another embodiment of an elbow assembly 5 including an AAV assembly 15 sandwiched between first and second portions 400, 402 of the elbow. In the illustrated embodiment, the port 40 protrudes into the elbow. However, the port 40 may have a flat face as illustrated in above described embodiments.

This embodiment has the additional advantage that the AAV assembly 15 forms an oxygen diverter valve with the lower portion of the elbow.

4.0 Elbow-to-Frame Interface

The following includes descriptions of mask assemblies including elbow to frame interfaces or assembly mechanisms according to several illustrated embodiments of the present invention. In each of the illustrated embodiments, the mask assembly includes an elbow that is adapted to be removably connected to a frame via an elbow to frame assembly mechanism.

The elbow to frame assembly mechanism provides an interface between the elbow and frame to facilitate assembly and disassembly. In addition, the elbow to frame assembly mechanism may be structured to facilitate molding of the elbow and/or frame.

In the illustrated embodiment, the elbow and frame form a part of a full-face mask. However, aspects of the present invention may be applicable to other breathing arrangements, e.g., a nasal mask, a mouth mask, etc. Also, each illustrated embodiment includes features that may be used with and/or in the other illustrated embodiments, as would be apparent to those of ordinary skill in the art.

4.1 First Embodiment

FIGS. 174-185 illustrate an elbow to frame assembly mechanism according to an embodiment of the present invention. As illustrated, the elbow 10 includes two snap-fit tabs 450 to connect the elbow 10 to the mask frame 455 with a snap-fit. Specifically, each snap-fit tab 450 includes a hook portion 452 that interlocks with an elbow retaining feature, e.g., annular ring 456, provided to the mask frame 455. Each snap-fit tab 450 includes external finger grips 454 to facilitate release of the elbow 10 from the mask frame 455 by pressing inwards on the external finger grips 454. The elbow retaining feature may be molded in a line of draw, i.e., easy to mold.

FIGS. 174-179 are exploded views illustrating the elbow 10 being assembled to the mask frame 455, and FIGS. 180-185 are various views illustrating the elbow 10 connected to the mask frame 455. This type of mechanism may be used in conjunction with embodiments 2.8, 2.9, 2.10, and 2.11, for example.

4.2 Second Embodiment

FIGS. 186-203 illustrate an elbow to frame assembly mechanism according to another embodiment of the present invention. As illustrated, the mask frame 460 includes an elbow-to-frame adaptor 462 to connect the elbow 10 to the mask frame 460 with a snap-fit. Specifically, the elbow-to-frame adaptor 462, e.g., constructed of rigid plastic, is attached to the mask frame 460 with a snap-fit. The elbow-to-frame adaptor 462 may be removable or permanently assembled, e.g., ultrasonic welding. The elbow-to-frame adaptor 462 is formed separately from the mask frame 460, e.g., molded as a separate part, to simplify molding of the mask frame 460. The elbow-to-frame adaptor 462 may be formed or molded in a different material from the mask frame 460 for aesthetic purposes and/or in a different material from the elbow to reduce the chance of squeak between like materials.

The elbow-to-frame adaptor 462 includes a flanged collar member 464 onto which the elbow 10 can be releasably connected. The elbow 10 is connected to the elbow-to-frame adaptor 462 in a snap-fit manner as is known from U.S. patent application publication no. 2003/0196656 incorporated herein by reference. The elbow 10 may be release from the elbow-to-frame adaptor 462 by pressing inwards on two external finger grips 468 provided to the elbow 10.

The elbow-to-frame adaptor 462 also includes a opening 466 that accommodates a port cap 470, e.g., formed of flexible silicone, releasably connected to a port provided to the mask frame 460. The port cap 470 may be permanently attached to the adaptor 462 via co-molding, etc., or remain separate.

FIGS. 186-191 are exploded views illustrating the elbow 10, mask frame 460, elbow-to-frame adaptor 462, and port cap 470, FIGS. 192-197 are partial assembled views illustrating the elbow-to-frame adaptor 462 connected to the mask frame 460, and FIGS. 198-203 are various assembled views illustrating the elbow 10 and port cap 470 connected to the mask frame 460.

4.3 Third Embodiment

FIGS. 204-221 illustrate an elbow to frame assembly mechanism according to another embodiment of the present invention. As illustrated, an elbow seal 472 is provided to the mask frame 474 to provide a seal between the elbow 10 and the mask frame 474. Specifically, the elbow seal 472, e.g., constructed of flexible silicone, is attached to the collar member of the mask frame 474. The elbow seal 472 covers air gaps and/or incorporates protrusions to interlock with gaps 480 in the mask frame 474 and also acts to reduce any sloppy fit between the mask frame 474 and the elbow 10, thereby reducing noise or squeak. A port cap 476, e.g., formed of flexible silicone, is integrated with the elbow seal 472. The port cap 476 is releasably connected to a port provided to the mask frame 474. The elbow seal 472 may be co-molded to the elbow or molded and vibration welded to the elbow if a TPE plastic, for example.

The collar member of the mask frame 474 includes a castellated rim that provides flange segments 478 that engage or interface with the elbow 10. The elbow 10 is connected to the flange segments 478 in a snap-fit manner as is known from U.S. patent application publication no. 2003/0196656 incorporated herein by reference.

Figure 209:
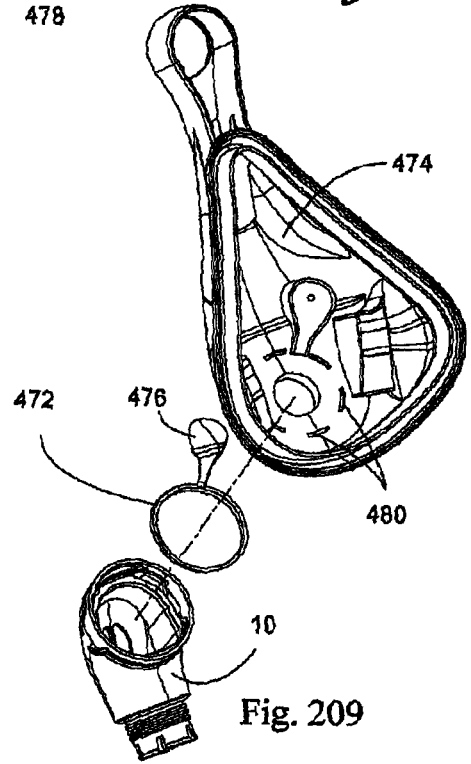
Figure 213:
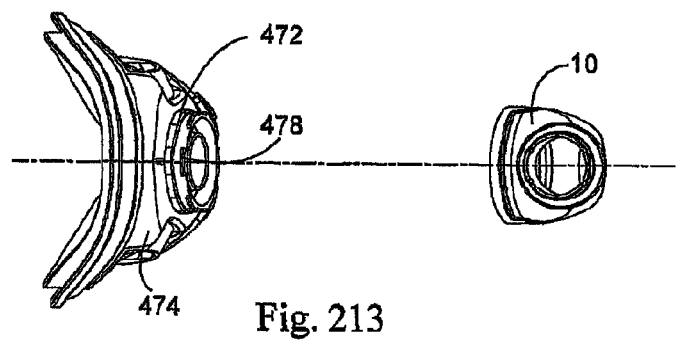
Figure 214:
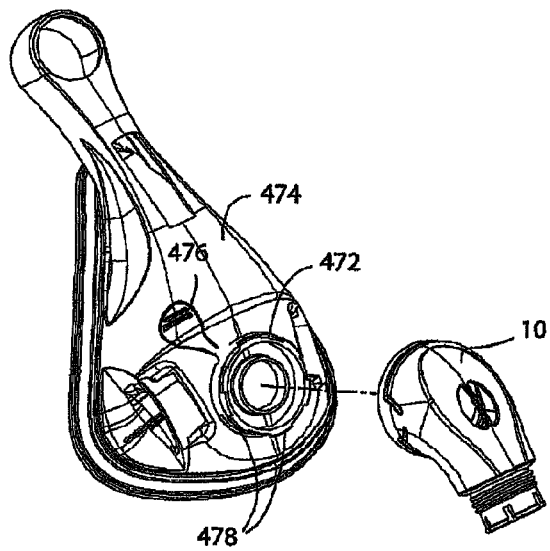
Figure 215:
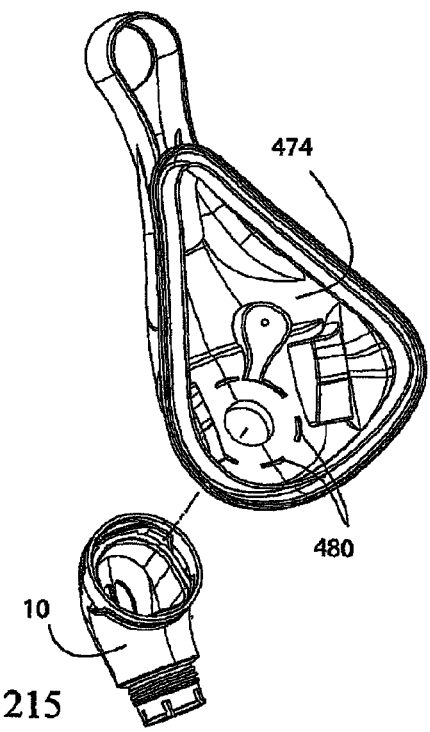
Figure 222:
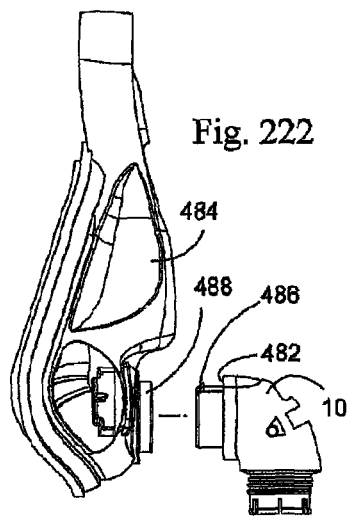
FIGS. 222-233 illustrate an elbow to frame assembly mechanism according to another embodiment of the present invention.
Figure 223:
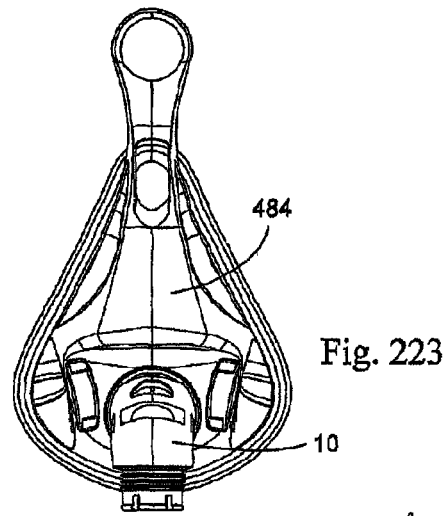
Figure 224:
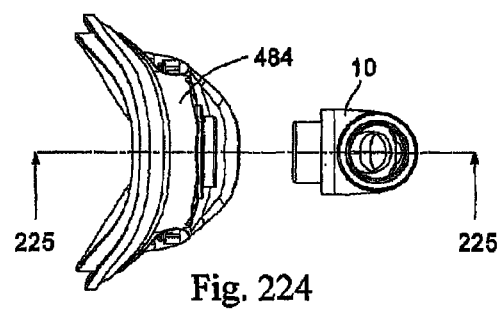
Figure 225:
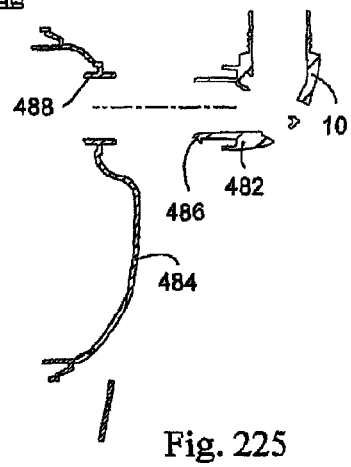
Figure 226:
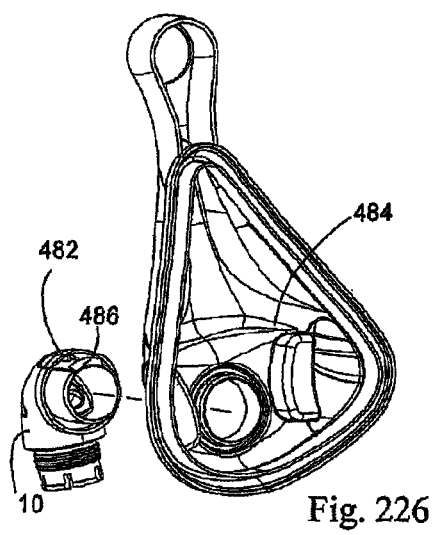
Figure 227:
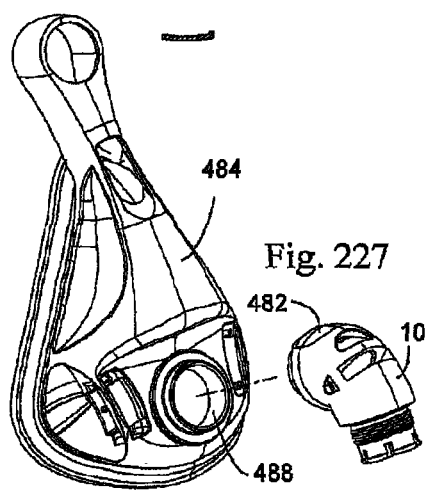
Figure 228:
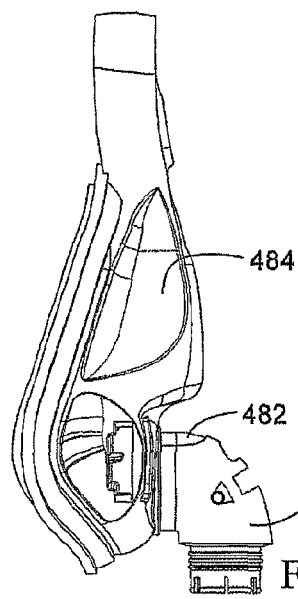
Figure 229:
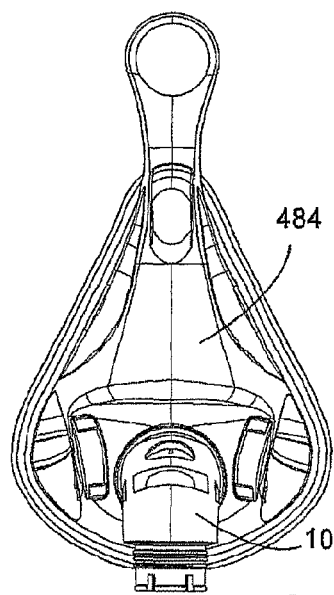
Figure 230:
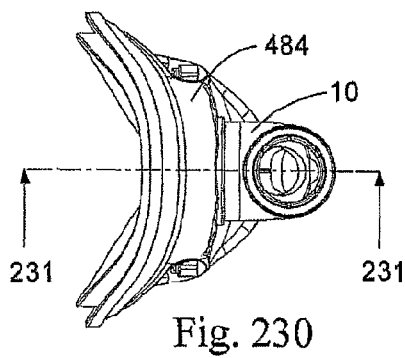
Figure 231:
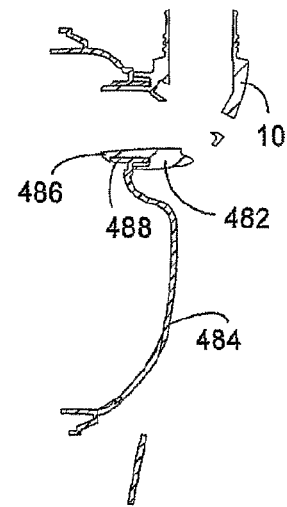
Figure 232:
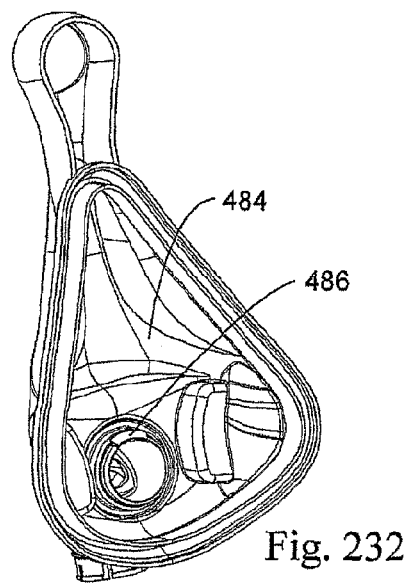
Figure 233:
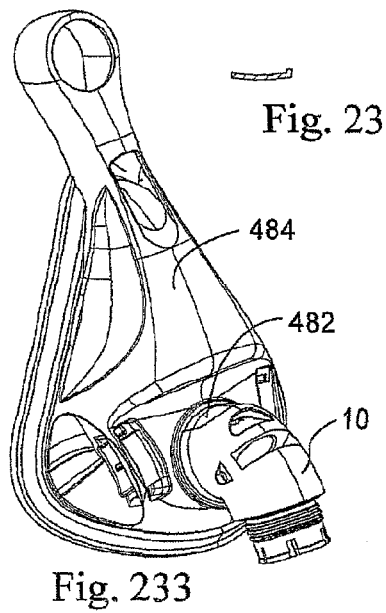
Figure 234:
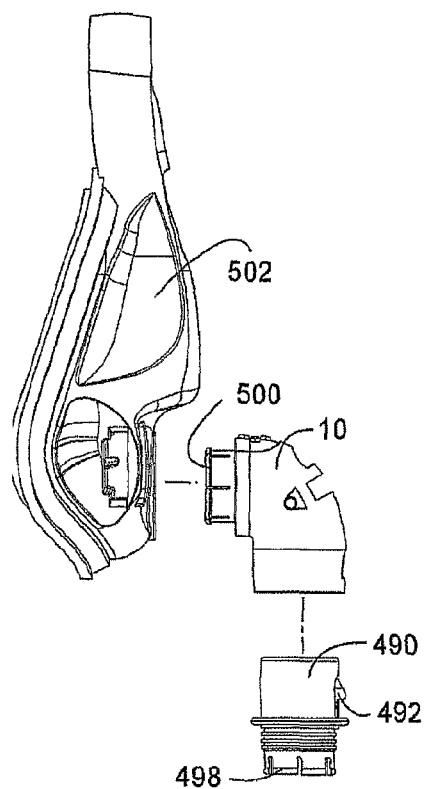
Figure 235:
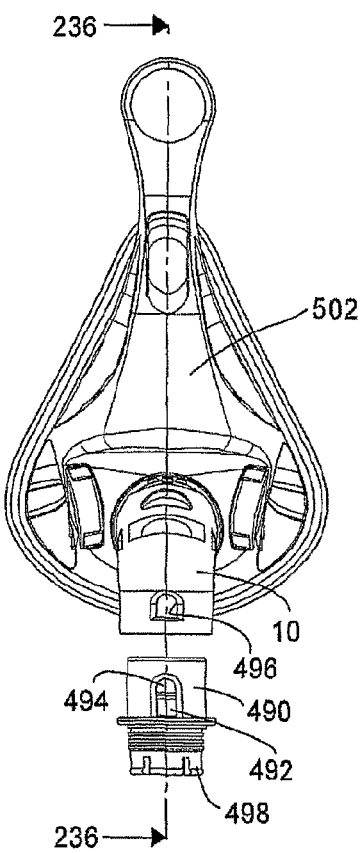
Figure 236:
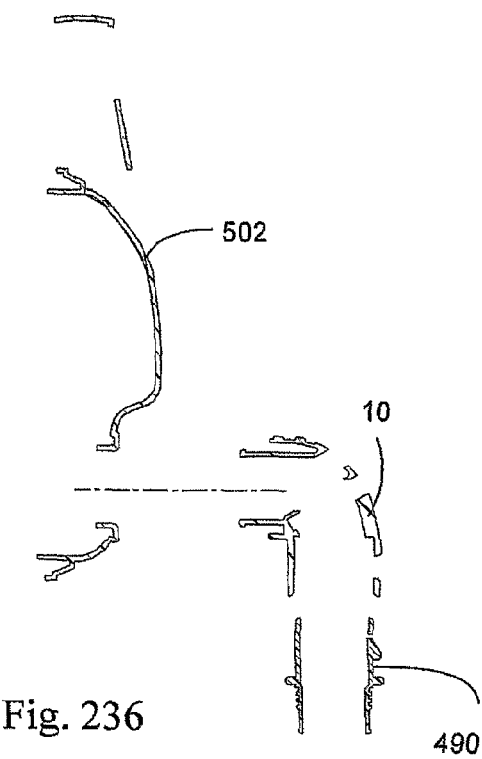
Figure 237:
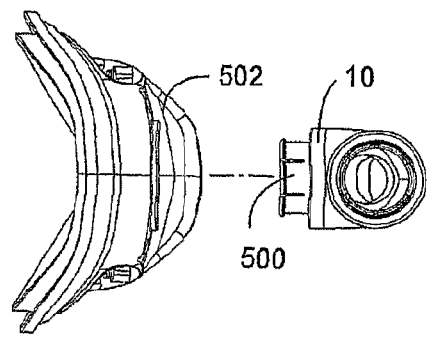
Figure 238:
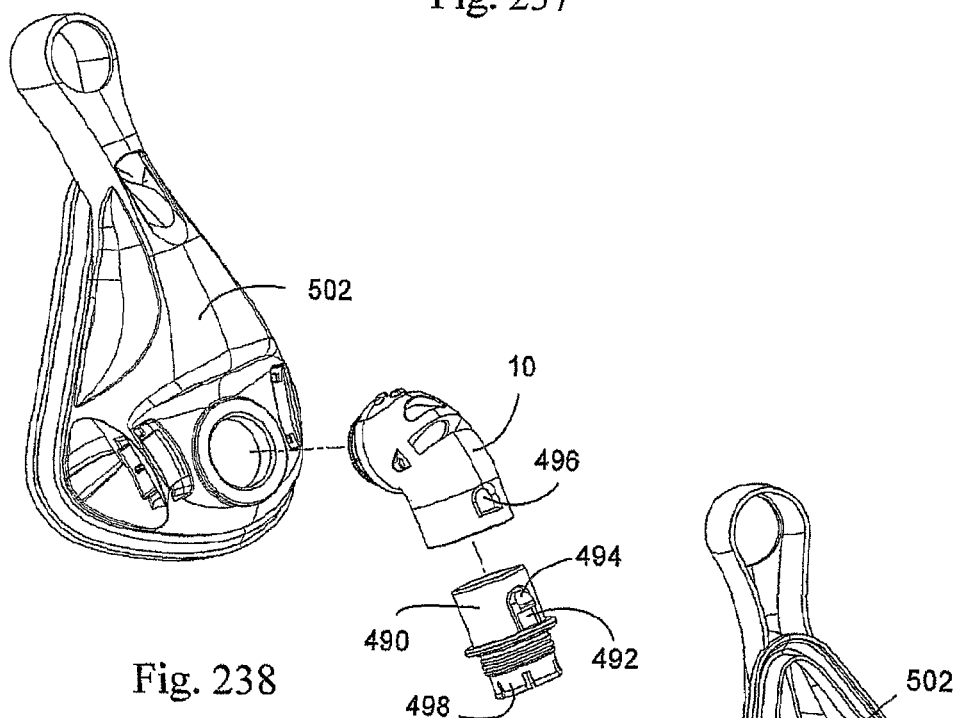
Figure 239:
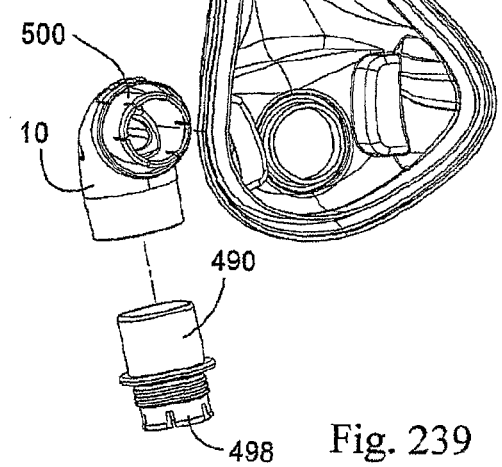
Figure 243:
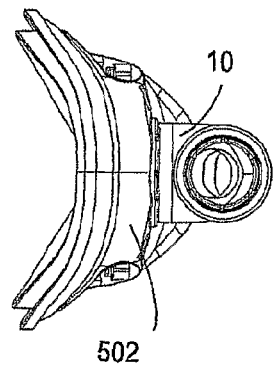
Figure 244:
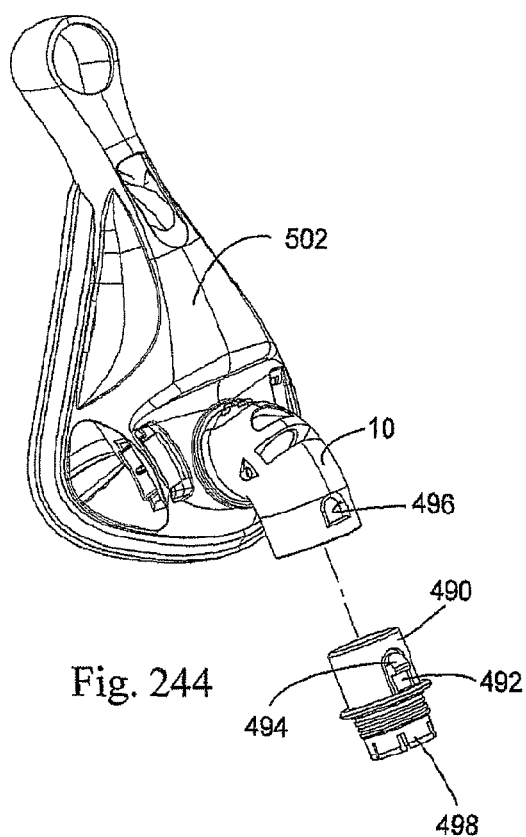
Figure 245:
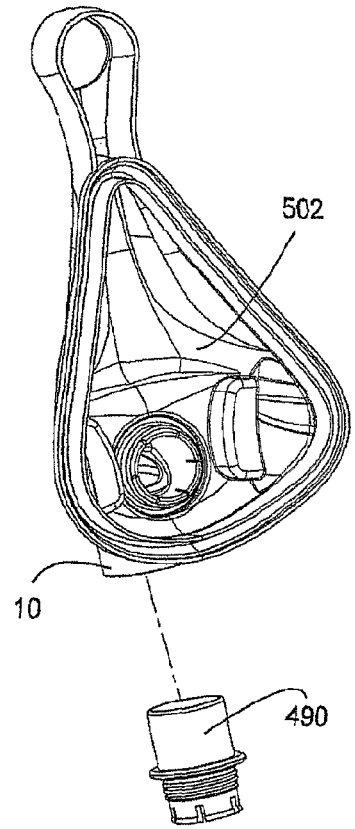
Figure 252:
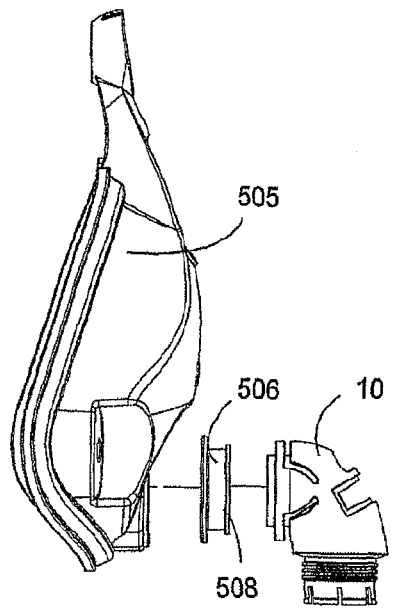
FIGS. 252-269 illustrate an elbow to frame assembly mechanism according to another embodiment of the present invention.
Figure 253:
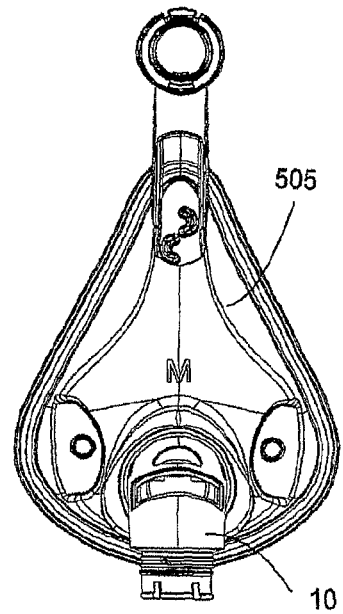
Figure 254:
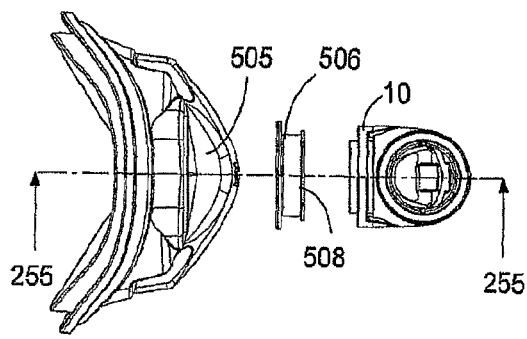
Figure 255:
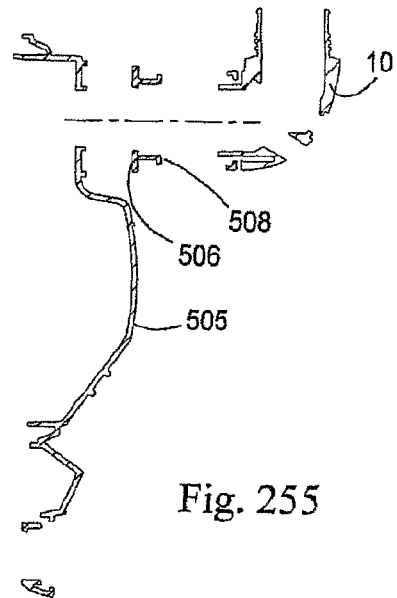
Figure 256:
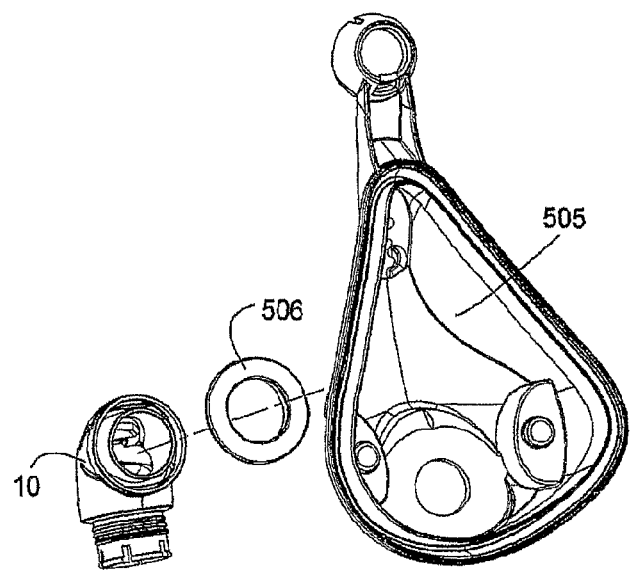
Figure 257:
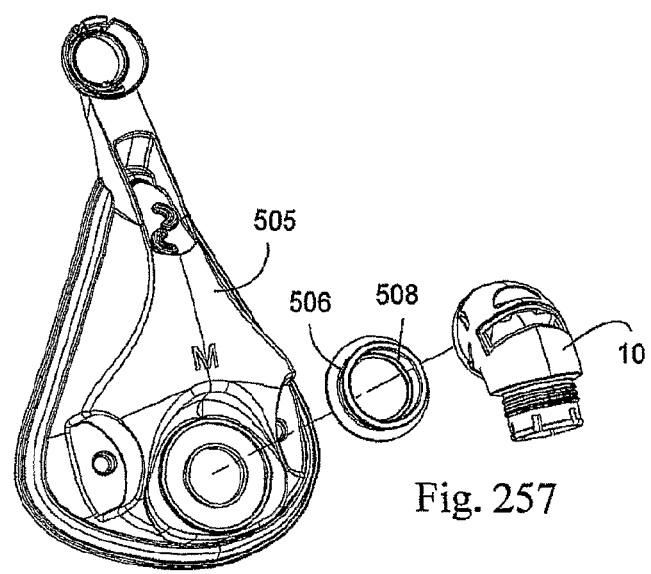
Figure 258:
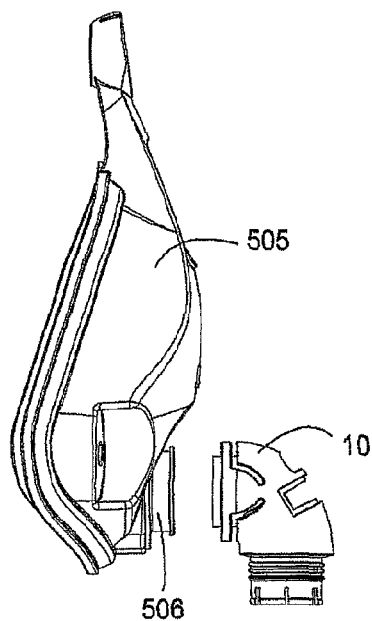
Figure 259:
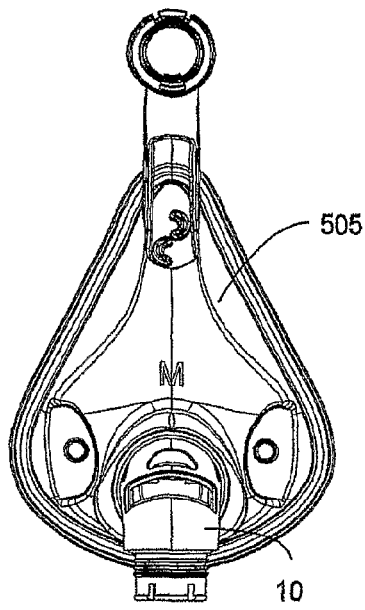
Figure 260:
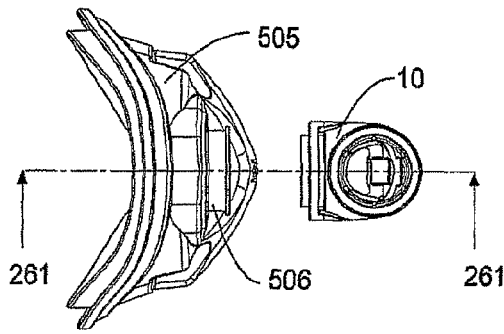
Figure 261:
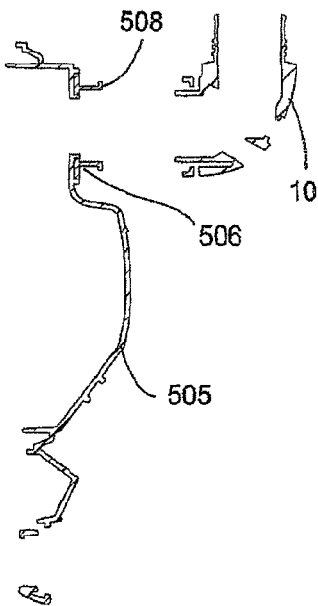
Figure 262:
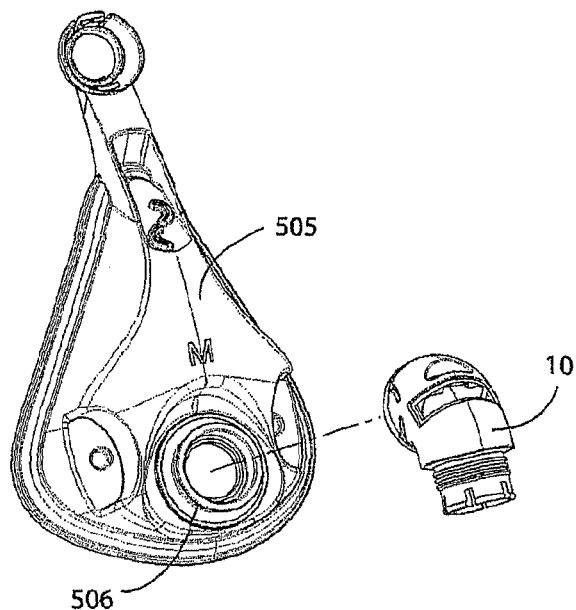
Figure 263:
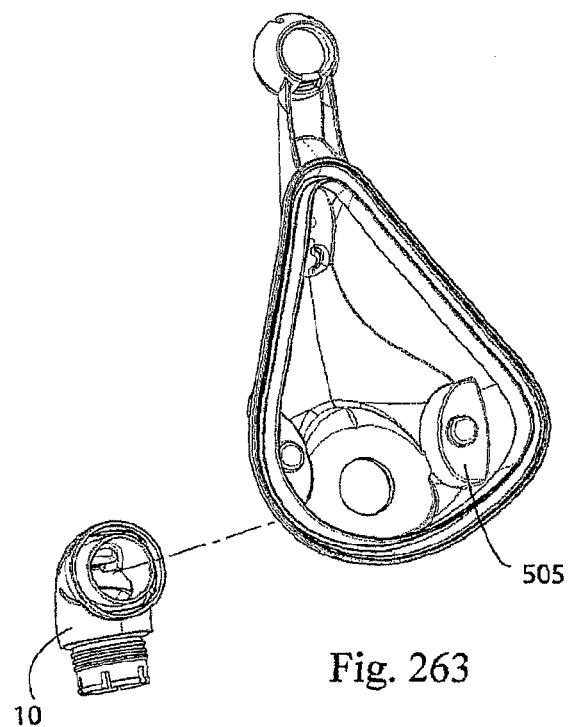
Figure 264:
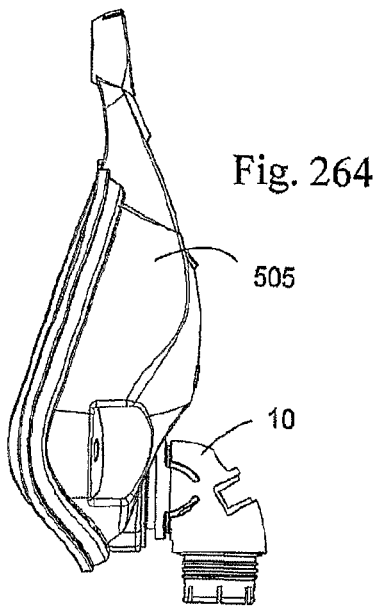
Figure 265:
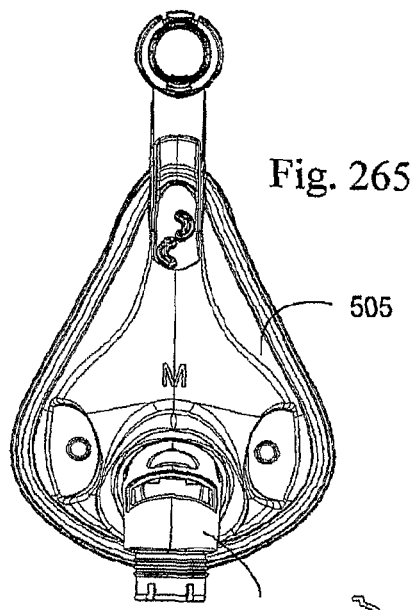
Figure 266:
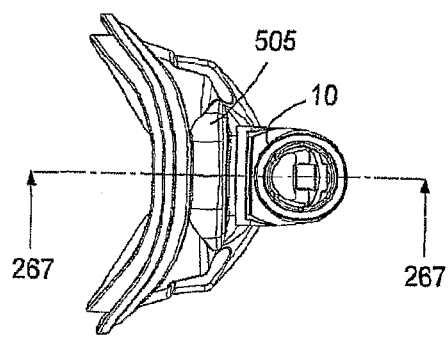
Figure 267:
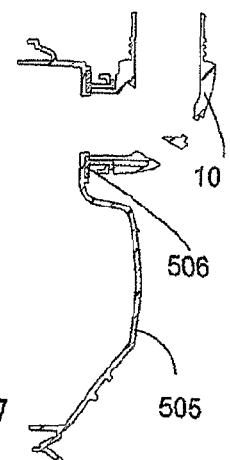
Figure 268:
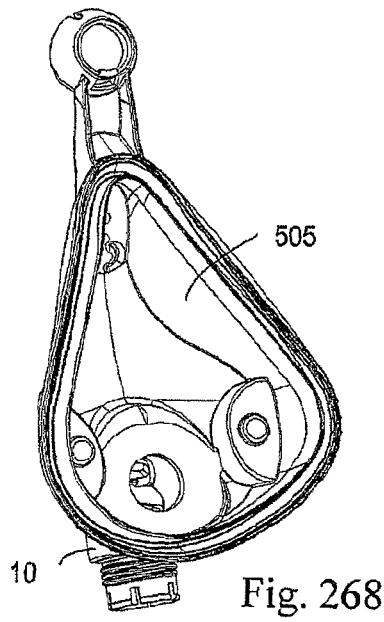
Figure 269:
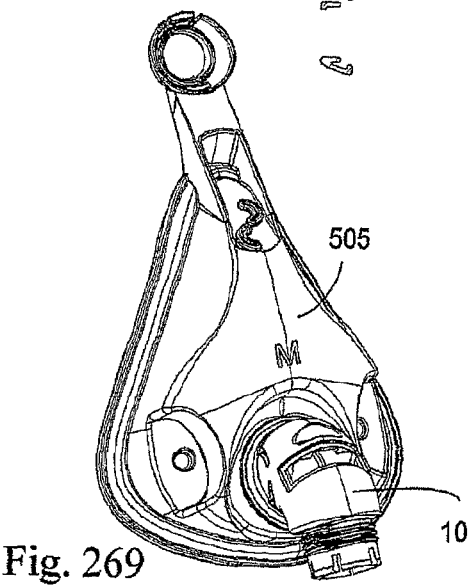
Figure 270:
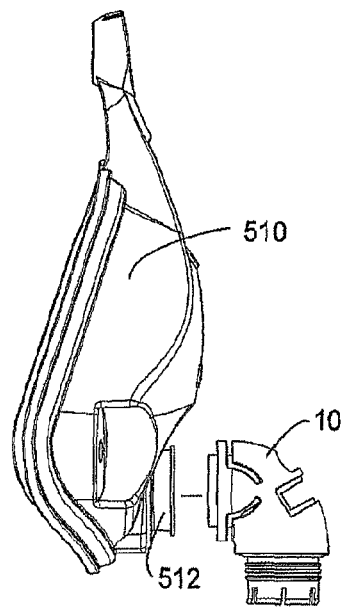
FIGS. 270-281 illustrate an elbow to frame assembly mechanism according to another embodiment of the present invention.
Figure 271:
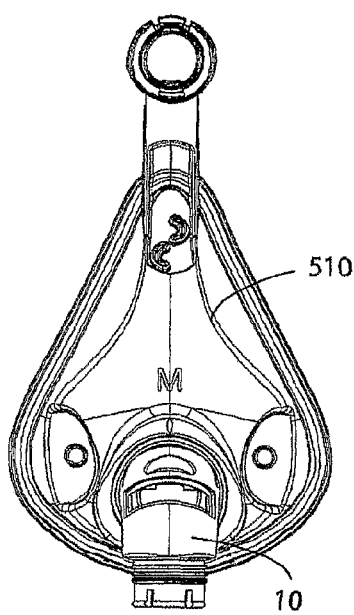
Figure 273:
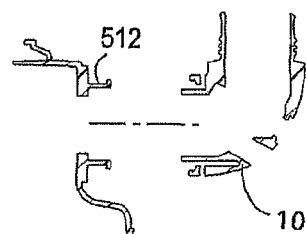
Figure 272:
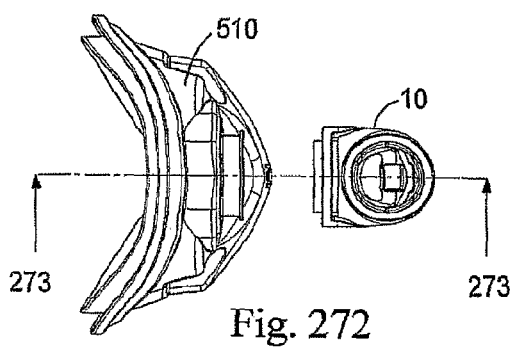
Figure 274:
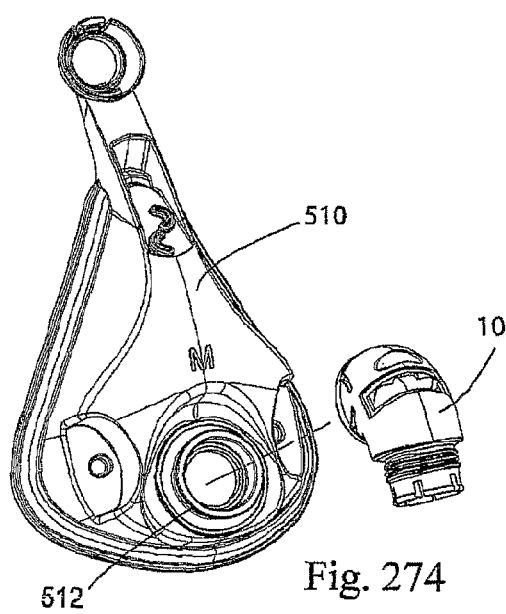
Figure 275:
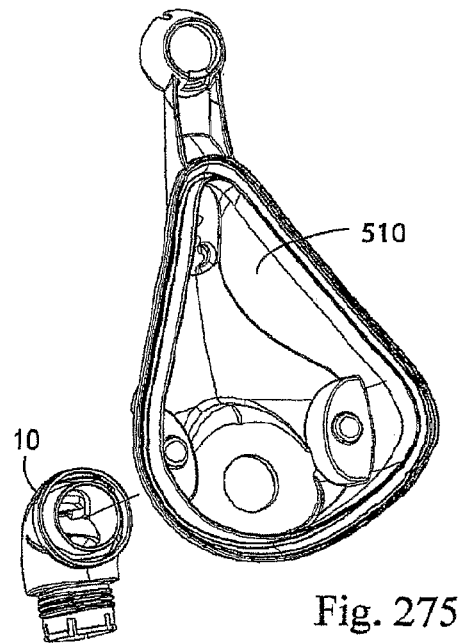
Figure 276:
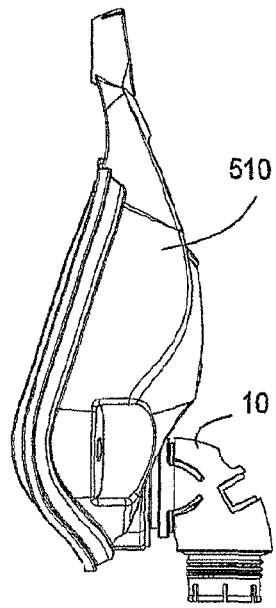
Figure 277:
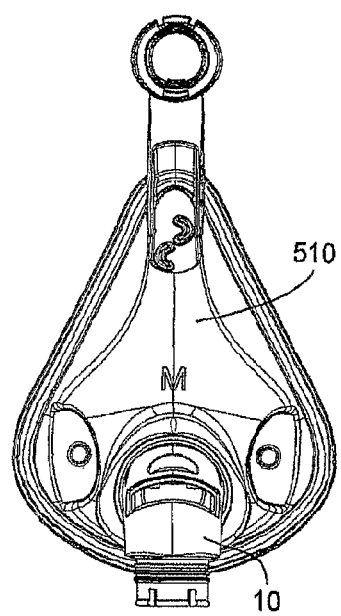
Figure 279:
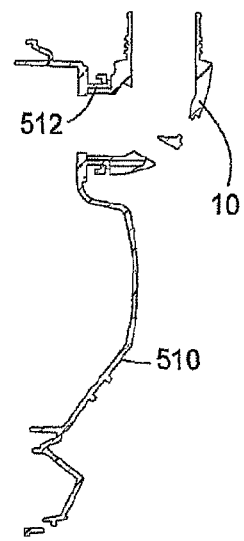
Figure 278:
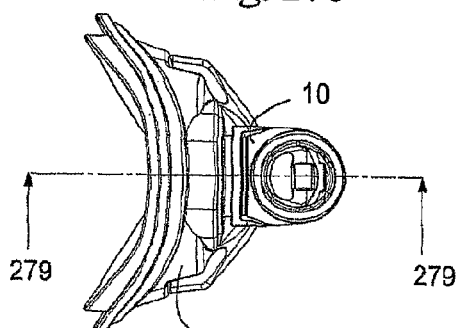
Figure 280:
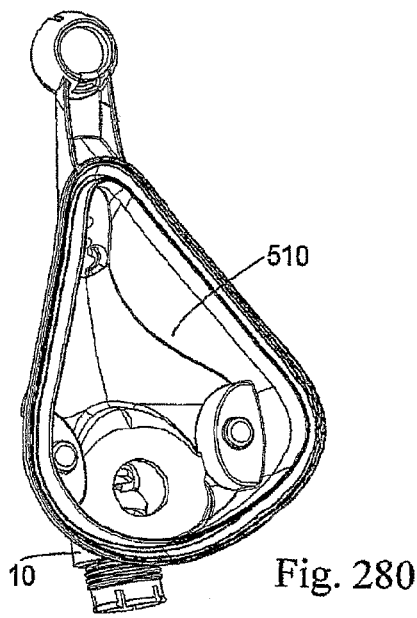
Figure 281:
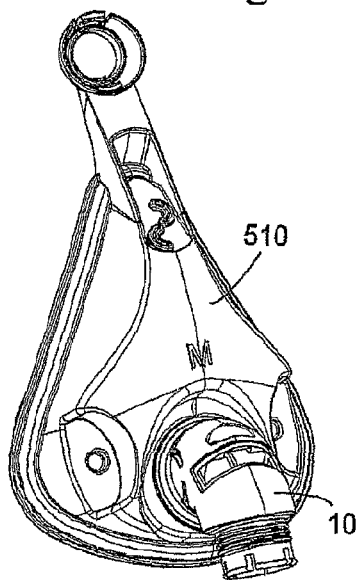
Figure 282:
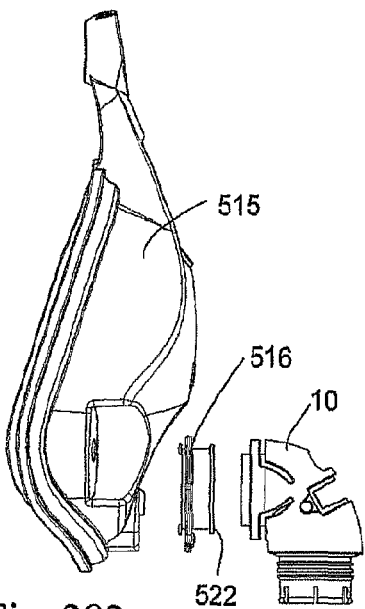
FIGS. 282-299 illustrate an elbow to frame assembly mechanism according to still another embodiment of the present invention.
Figure 283:
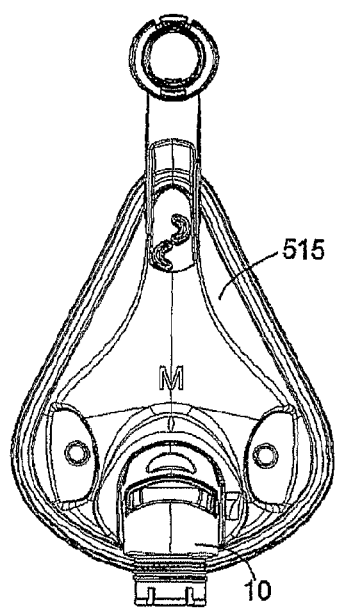
Figure 284:
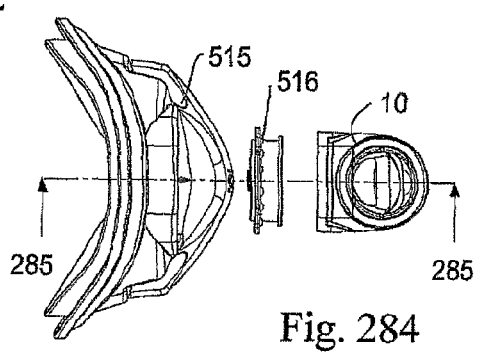
Figure 285:
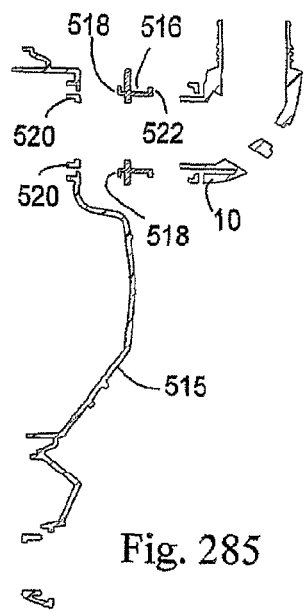
Figure 286:
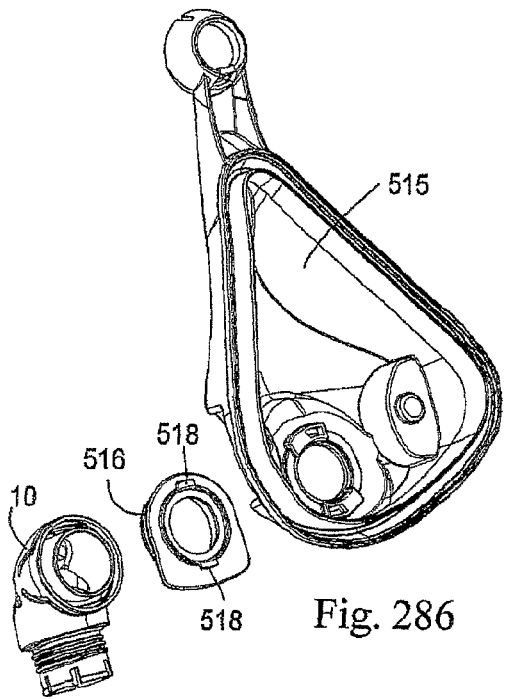
Figure 287:
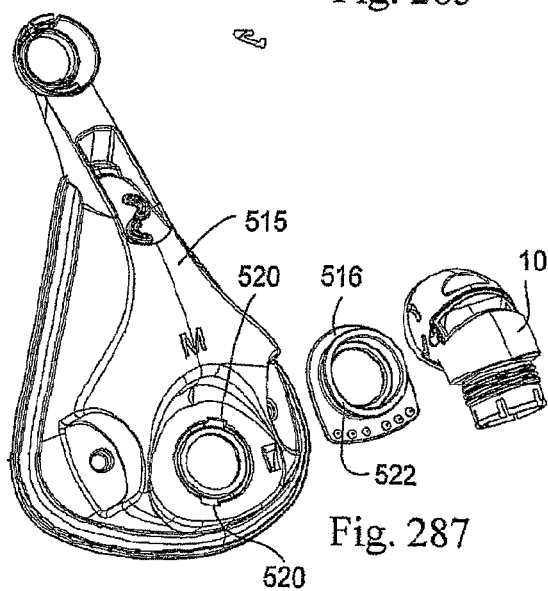
Figure 288:
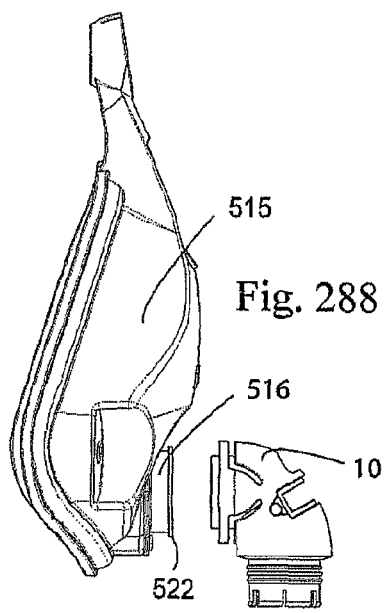
Figure 289:
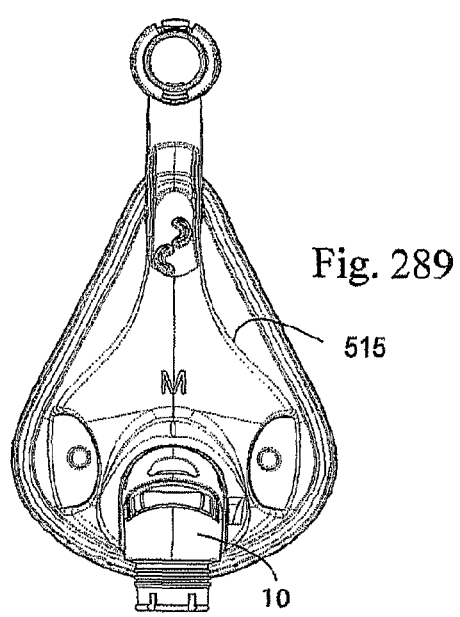
Figure 290:
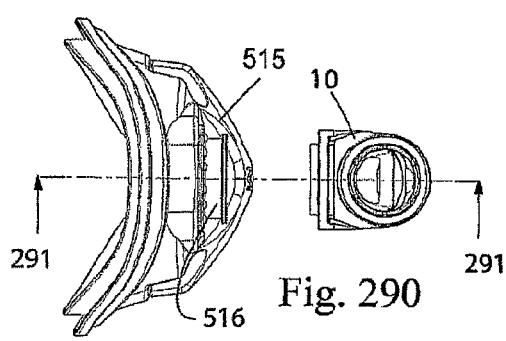
Figure 291:
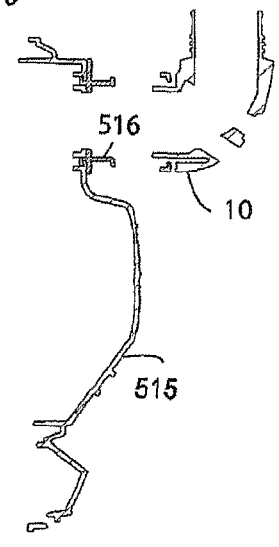
Figure 292:
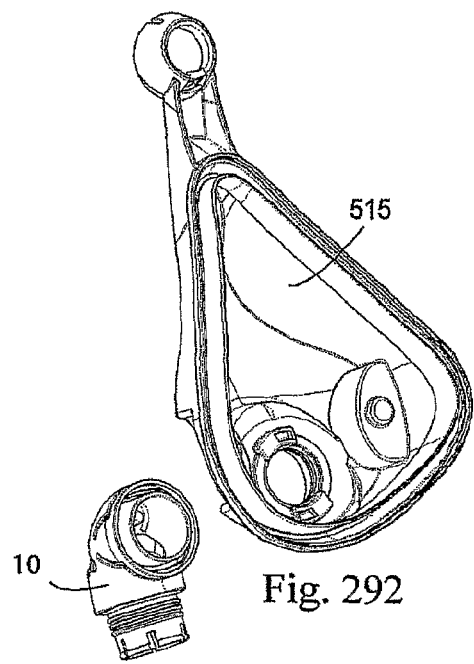
Figure 293:
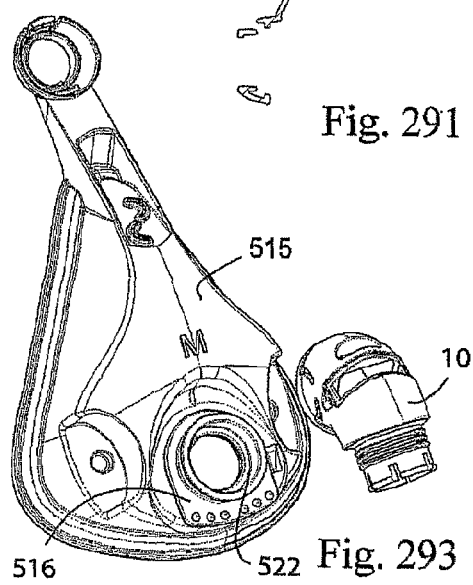
Figure 294:
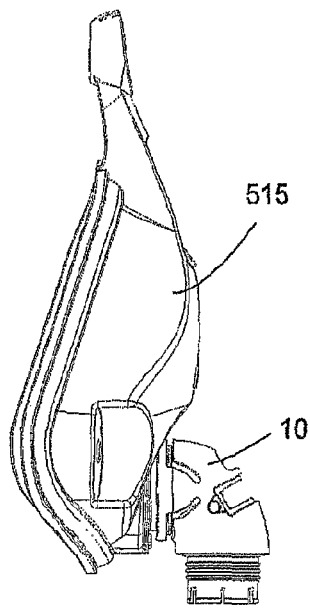
Figure 295:
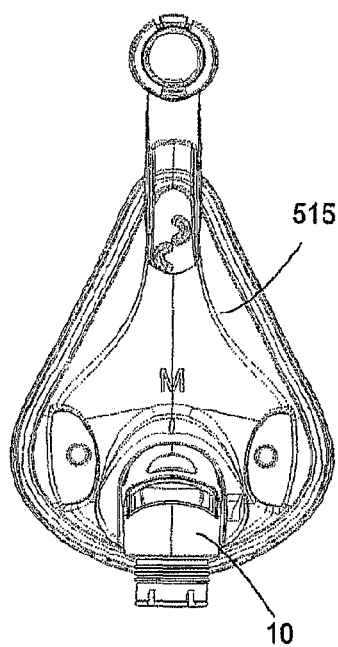
Figure 296:
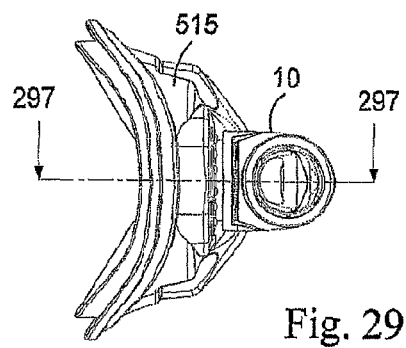
Figure 297:
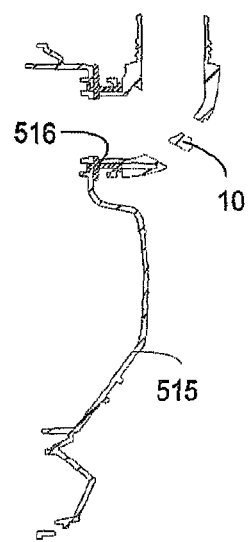
Figure 298:
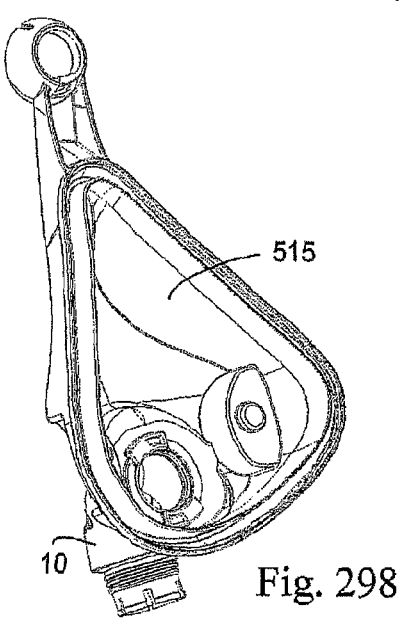
Figure 299:
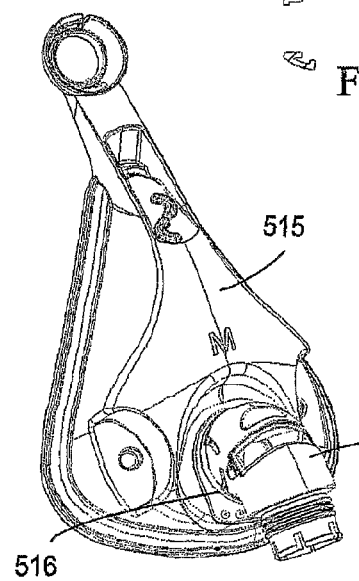

As best shown in FIGS. 209, 215, and 221, localized gaps 480 are formed in the mask frame 474 as a result of the molding process. The localized gaps 480 enable the castellated feature on the collar member of the mask frame 474 to be molded more easily.

FIGS. 204-209 are exploded views illustrating the elbow 10, mask frame 474, and elbow seal and integrated port cap 472, 476, FIGS. 210-215 are partial assembled views illustrating the elbow seal and integrated port cap 472, 476 connected to the mask frame 474, and FIGS. 216-221 are various assembled views illustrating the elbow 10 connected to the mask frame 474.

In the illustrated embodiment, the elbow seal is provided between the elbow and the frame. In an alternative embodiment, an over seal may be provided that seals with an exterior surface of the elbow and an exterior rib provided to the frame. Thus, the over seal seals over the elbow and frame. The seal may be integrated, co-molded, or over-molded to the elbow, for example.

4.4 Fourth Embodiment

FIGS. 222-233 illustrate an elbow to frame assembly mechanism according to another embodiment of the present invention. As illustrated, the elbow 10 includes a snap-fit tab 482 on a top portion thereof to connect the elbow 10 to the mask frame 484 with a snap-fit. Specifically, the snap-fit tab 482 includes a hook portion 486 that interlocks with a collar 488 provided to the mask frame 484. The elbow 10 is pulled outwardly while depressing tab 482 to release the elbow 10 from the mask frame 484. The elbow-to-frame interface detail or collar 488 may be molded in a line of draw and with side cores, i.e., relatively easy to mold. The tab 482 may be used in conjunction with snap-fit tabs described previously (e.g., see FIGS. 68-89 and 234-251), of which there may be any suitable number of previously described snap-fit tabs, e.g., 2-10 tabs.

FIGS. 222-227 are exploded views illustrating the elbow 10 being assembled to the mask frame 484, and FIGS. 228-233 are various views illustrating the elbow 10 connected to the mask frame 484.

4.5 Fifth Embodiment

FIGS. 234-251 illustrate an elbow to frame assembly mechanism according to another embodiment of the present invention. As illustrated, the mask frame elbow 10 includes an elbow-to-swivel adaptor 490 to connect the elbow 10 to a swivel (not shown) with a snap-fit. Specifically, the elbow-to-swivel adaptor 490, e.g., constructed of rigid plastic, includes a snap-fit tab 492 to connect the adaptor 490 to the elbow 10 with a snap-fit. Specifically, the snap-fit tab 492 includes a hook portion 494 that interlocks with an opening 496 provided to the elbow 10. The snap-fit tab 494 is pushed inwardly to release the adaptor 490 from the elbow 10. The end of the adaptor includes multiple snap-fit tabs 498 to connect the adaptor 490 to a swivel. The elbow 10 also includes multiple snap-fit tabs 500 to connect the elbow 10 to the mask frame 502 with a snap-fit. In this embodiment, the snap-fit tabs 500 are a semi-permanent connection and the quick release connection is via tab 492.

FIGS. 234-239 are exploded views illustrating the elbow 10, mask frame 502, and elbow-to-swivel adaptor 490, FIGS. 240-245 are partial assembled views illustrating the elbow 10 connected to the mask frame 502, and FIGS. 246-251 are various assembled views illustrating the elbow 10 connected to the mask frame 502 and elbow-to-swivel adaptor 490.

4.6 Sixth Embodiment

FIGS. 252-269 illustrate an elbow to frame assembly mechanism according to another embodiment of the present invention. As illustrated, the mask frame 505 includes an elbow-to-frame adaptor 506 to connect the elbow 10 to the mask frame 505 with a snap-fit. Specifically, the elbow-to-frame adaptor 506, e.g., constructed of rigid plastic, is attached to the mask frame 505. The elbow-to-frame adaptor 506 may be removably attached (e.g., snap-fit assembly, bayonet connection), glued, or ultrasonically welded in place to the mask frame 505. The elbow-to-frame adaptor 506 is formed separately from the mask frame 505, e.g., molded as a separate part, to simplify molding of the mask frame 505.

The elbow-to-frame adaptor 506 includes a flanged collar member 508 onto which the elbow 10 can be releasably connected. The elbow 10 is connected to the elbow-to-frame adaptor 506 in a snap-fit manner as is known from U.S. patent application publication no. 2003/0196656 incorporated herein by reference.

FIGS. 252-257 are exploded views illustrating the elbow 10, mask frame 505, and elbow-to-frame adaptor 506, FIGS. 258-263 are partial assembled views illustrating the elbow-to-frame adaptor 506 connected to the mask frame 505, and FIGS. 264-269 are various assembled views illustrating the elbow 10 connected to the mask frame 505.

4.7 Seventh Embodiment

FIGS. 270-281 illustrate an elbow to frame assembly mechanism according to another embodiment of the present invention. As illustrated, the mask frame 510 includes a flanged collar member 512 onto which the elbow 10 can be releasably connected. The elbow 10 is connected to the flanged collar member 512 in a snap-fit manner as is known from U.S. patent application publication Ser. No. 10/390,682 incorporated herein by reference. In an embodiment, the flanged collar member 512 or interface rim is integrally molded with the mask frame 510 using a 3-part split collar in the mold.

FIGS. 270-275 are exploded views illustrating the elbow 10 being assembled to the mask frame 510, and FIGS. 276-281 are various views illustrating the elbow 10 connected to the mask frame 510.

4.8 Eighth Embodiment

FIGS. 282-299 illustrate an elbow to frame assembly mechanism according to another embodiment of the present invention. As illustrated, the mask frame 515 includes an elbow-to-frame adaptor 516 to connect the elbow 10 to the mask frame 515 with a snap-fit. Specifically, the elbow-to-frame adaptor 516, e.g., constructed of rigid plastic, is attached to the mask frame 515. In the illustrated embodiment, the elbow-to-frame adaptor 516 is removably attached to the mask frame 515 via a bayonet-style fitting. That is, the adaptor 516 includes tabs 518 that interlock with respective recesses 520 provided to the mask frame 515. The elbow-to-frame adaptor 516 is formed separately from the mask frame 515, e.g., molded as a separate part, to simplify molding of the mask frame 515.

The elbow-to-frame adaptor 516 includes a flanged collar member 522 onto which the elbow 10 can be releasably connected. The elbow 10 is connected to the elbow-to-frame adaptor 516 in a snap-fit manner as is known from U.S. patent application publication no. 2003/0196656 incorporated herein by reference.

FIGS. 282-287 are exploded views illustrating the elbow 10, mask frame 515, and elbow-to-frame adaptor 516, FIGS. 288-293 are partial assembled views illustrating the elbow-to-frame adaptor 516 connected to the mask frame 515, and FIGS. 294-299 are various assembled views illustrating the elbow 10 connected to the mask frame 515.

An advantage of the above-described embodiments is that they may be suitable for multi-patient multi-use (MPMU). That is, the entire elbow assembly may be sterilized or disinfected as appropriate for use between different patients. The above-described embodiments have the advantage of MPMU due to their increased size over known AAV assemblies and the fact that the elbow, AAV assembly, and clip member may be pulled apart for cleaning. This is different to other known designs that are permanently assembly, e.g., Respironics Comfort Full.

The AAV assemblies 15 are not limited to the shapes and/or sizes described above. For example, the AAV assemblies 15 may have oval, rectangular, or other suitable shapes. Also, the elbow slot for receiving the AAV assembly may have an angle in the range of 20-40° with respect to horizontal, e.g., 30°. Further, the AAV assemblies may be constructed of LSR as well as other suitable materials, e.g., TPU, TPE.

It will be understood that, in each of the above-described embodiments, reference to an AAV assembly 15 may include an integral one-piece structure, or multiple parts that are formed separately from one another and then interconnected.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. An elbow assembly comprising:
   an elbow with an opening in a sidewall of the elbow, the sidewall defining an air flow passage; the airflow passage extending between a first end of the elbow configured to receive pressurized gas and a second end of the elbow configured to be secured to a mask;
   an anti-asphyxia valve (AAV) assembly provided to the elbow, the sidewall opening of the elbow being configured to receive at least a portion of the AAV assembly so that at least a portion of the AAV assembly is positioned within the air flow passage; and
   a support member with an opening to atmosphere in an outer surface of the support member, the support member being configured to be secured to a portion of the elbow and cover the sidewall opening of the elbow, the AAV assembly being secured to the elbow by the support member and adapted to selectively close the opening to atmosphere,
   wherein the support member is configured so that the outer surface of the support member is substantially flush with an outer surface of the elbow when the support member is secured to the portion of the elbow.

2. The elbow assembly of claim 1, wherein the sidewall opening of the elbow comprises a slot.

3. The elbow assembly of claim 2, wherein the slot is structured to receive the AAV assembly, and the support member is secured to the outer surface of the elbow.

4. The elbow assembly of claim 2, wherein the support member is formed as part of a main wall member of the AAV assembly.

5. The elbow assembly of claim 4, wherein the main wall member and elbow are secured via a tongue and groove arrangement.

6. The elbow assembly of claim 4, wherein the main wall member includes a circumferential groove that receives a tongue of the elbow.

7. The elbow assembly of claim 4, wherein the main wall member is substantially flush with the outer surface of the elbow.

8. The elbow assembly of claim 1, wherein the AAV assembly includes a main wall member secured to a cylindrical portion of the elbow.

9. The elbow assembly of claim 8, wherein the main wall member is generally planar.

10. The elbow assembly of claim 8, wherein the cylindrical portion of the elbow includes an extension presenting a substantially planar surface for securing of the AAV assembly.

11. The elbow assembly of claim 1, wherein the AAV assembly is positioned adjacent to the opening to atmosphere.

12. The elbow assembly of claim 11, wherein the opening to atmosphere includes a cylindrical wall member configured to be selectively engaged by a portion of the AAV assembly.

13. The elbow assembly of claim 1, wherein the support member comprises an overclip member.

14. The elbow assembly of claim 1, wherein the support member comprises a push-fit clip member.

15. The elbow assembly of claim 1, wherein the support member comprises a shroud-type clip member.

16. The elbow assembly of claim 1, wherein the support member and the AAV assembly are formed as an integral unit.

17. The elbow assembly of claim 1, wherein the support member and the AAV assembly are secured together by over-molding, gluing and/or a mechanical lock.

18. The elbow assembly of claim 1, wherein the support member includes an aperture and the AAV assembly includes a lug which is received within the aperture.

19. The elbow assembly of claim 1, wherein the AAV assembly is generally D-shaped in plan view.

20. The elbow assembly of claim 1, wherein the AAV assembly is generally trapezoidal in profile.

21. The elbow assembly of claim 1, wherein the AAV assembly includes a base portion and a flap portion hingedly provided to the base portion.

22. The elbow assembly of claim 21, wherein the hinge is in the form of a living hinge.

23. The elbow assembly of claim 21, wherein the hinge is formed along only a portion between the base portion and the flap portion.

24. The elbow assembly of claim 21, wherein the AAV assembly includes a rim surrounding the base portion.

25. The elbow assembly of claim 1, wherein the AAV assembly includes a main wall member having at least one dimension that is larger than the opening provided in the elbow, the main wall member being substantially perpendicular to the AAV assembly insertion direction.

26. The elbow assembly of claim 1, wherein the support member is generally U-shaped and includes a central wall and side arms, each of the side arms including a retaining mechanism secured to the elbow.

27. The elbow assembly of claim 26, wherein the retaining mechanism includes a lug provided to each arm that is received within a slot provided on each side of the elbow.

28. The elbow assembly of claim 1, wherein the elbow includes a first portion adapted to be secured to a frame of a mask assembly and a second portion structured to receive pressurized gas, and a first gas path is defined between the first and second portions.

29. The elbow assembly of claim 28, wherein the opening to atmosphere is provided between the first and second portions.

30. The elbow assembly of claim 29, further comprising a second gas path defined between the first portion and the opening to atmosphere.

31. The elbow assembly of claim 28, wherein the AAV assembly includes a flap portion to selectively allow either pressurized gas or ambient air to be directed to the first portion of the elbow.

32. The elbow assembly of claim 31, wherein the flap portion is made of silicone or TPE.

33. The elbow assembly of claim 31, wherein the flap portion comprises liquid silicone rubber.

34. A mask assembly comprising: a frame; and an elbow assembly according to claim 1.

35. The mask assembly of claim 34, wherein the frame includes a baffle portion that engages with a seal lip of the AAV assembly upon assembly of the elbow assembly with the mask frame.

36. The elbow assembly of claim 1, wherein the support member comprises an overhang portion that provides a finger grip or catch for removal of the support member from the elbow.

37. The elbow assembly of claim 1, wherein the support member is adapted to contact the AAV assembly when securing the AAV assembly to the elbow.

38. The elbow assembly of claim 1, wherein the support member is securable to the elbow in only one orientation.

39. The elbow assembly of claim 1, wherein the outer surface of the support member is substantially flush with the outer surface of the elbow only when the support member is oriented in a predetermined direction relative to the elbow.

40. The elbow assembly of claim 1, wherein an entirety of the outer surface of the support member is substantially flush with an outer surface of the elbow when the support member is secured to the elbow.

41. The elbow assembly of claim 1, wherein the support member is generally U-shaped.

* * * * *